US008546451B2

(12) United States Patent
Dalton et al.

(10) Patent No.: US 8,546,451 B2
(45) Date of Patent: *Oct. 1, 2013

(54) ESTROGEN RECEPTOR LIGANDS AND METHODS OF USE THEREOF

(75) Inventors: James T. Dalton, Lakeland, TN (US); Mitchell S. Steiner, Germantown, TN (US); Jeetendra Eswaraka, Carlsbad, CA (US)

(73) Assignee: GTx, Inc., Memphis, TN (US)

( * ) Notice: Subject to any disclaimer, the term of this patent is extended or adjusted under 35 U.S.C. 154(b) by 393 days.

This patent is subject to a terminal disclaimer.

(21) Appl. No.: 12/710,693

(22) Filed: Feb. 23, 2010

(65) Prior Publication Data

US 2010/0267773 A1    Oct. 21, 2010

Related U.S. Application Data

(63) Continuation-in-part of application No. 11/785,251, filed on Apr. 16, 2007, now Pat. No. 8,158,828, and a continuation-in-part of application No. 11/604,884, filed on Nov. 28, 2006.

(60) Provisional application No. 60/739,898, filed on Nov. 28, 2005, provisional application No. 61/261,669, filed on Nov. 16, 2009, provisional application No. 61/168,983, filed on Apr. 14, 2009, provisional application No. 61/154,707, filed on Feb. 23, 2009.

(51) Int. Cl.
*A61K 31/165* (2006.01)

(52) U.S. Cl.
USPC ........... 514/620; 514/563; 514/617; 514/618; 514/619

(58) Field of Classification Search
USPC ...................... 514/563, 617, 618, 619, 620
See application file for complete search history.

(56) References Cited

U.S. PATENT DOCUMENTS

| | | | |
|---|---|---|---|
| 3,413,339 A | 11/1968 | Scherrer | |
| 3,625,972 A | 12/1971 | Schulenberg | |
| 3,838,131 A | 9/1974 | Gauthier et al. | |
| 3,838,134 A | 9/1974 | Gauthier et al. | |
| 3,960,886 A | 6/1976 | Schulenberg | |
| 4,373,017 A | 2/1983 | Masukawa et al. | |
| 5,480,656 A | 1/1996 | Okada et al. | |
| 5,491,173 A | 2/1996 | Toivola et al. | |
| 5,575,987 A | 11/1996 | Kamei et al. | |
| 5,631,020 A | 5/1997 | Okada et al. | |
| 5,643,607 A | 7/1997 | Okada et al. | |
| 5,716,640 A | 2/1998 | Kamei et al. | |
| 5,814,342 A | 9/1998 | Okada et al. | |
| 6,036,976 A | 3/2000 | Takechi et al. | |
| 6,166,013 A | 12/2000 | Coghlan et al. | |
| 6,518,301 B1 | 2/2003 | Barlaam et al. | |
| 6,632,447 B1 | 10/2003 | Steiner et al. | |
| 6,762,205 B1 * | 7/2004 | Koizumi et al. | 514/602 |
| 7,001,911 B2 | 2/2006 | Salvati et al. | |
| 7,118,552 B2 | 10/2006 | Shaw et al. | |
| 7,220,247 B2 | 5/2007 | Shaw et al. | |
| 7,500,964 B2 | 3/2009 | Shaw et al. | |
| 8,158,828 B2 * | 4/2012 | Dalton et al. | 564/179 |
| 2002/0119953 A1 | 8/2002 | Brugnara | |
| 2002/0156301 A1 | 10/2002 | Kaneko | |
| 2002/0192310 A1 | 12/2002 | Bland et al. | |
| 2003/0153625 A1 | 8/2003 | Steiner | |
| 2004/0082813 A1 | 4/2004 | Iwakuma | |
| 2005/0182143 A1 | 8/2005 | Anttila | |
| 2006/0287282 A1 | 12/2006 | Steiner et al. | |
| 2006/0287359 A1 | 12/2006 | Danso-Danquah et al. | |
| 2007/0265296 A1 | 11/2007 | Dalton et al. | |
| 2009/0062341 A1 | 3/2009 | Dalton et al. | |
| 2009/0156614 A1 | 6/2009 | Dalton et al. | |

FOREIGN PATENT DOCUMENTS

| | | |
|---|---|---|
| DE | 269 213 | 1/1914 |
| DE | 269213 | 1/1914 |
| DE | 2228351 | 12/1972 |
| EP | 0501656 | 9/1992 |
| EP | 1 193 250 | 4/2002 |
| EP | 1193250 | 4/2002 |
| EP | 1 593 665 | 11/2005 |
| FR | 4333 | 9/1966 |
| FR | 1536400 | 7/1967 |
| FR | 1.557.928 | 2/1969 |
| FR | 7699 | 2/1970 |
| FR | 2.098.587 | 4/1972 |
| GB | 2126576 | 3/1984 |
| GB | 2305173 | 2/1997 |
| GB | 2305177 | 2/1997 |
| JP | 49127938 A | 12/1974 |
| JP | 2002322162 | 11/2002 |
| JP | 2004307380 | 11/2004 |
| JP | 2005-255981 | 9/2005 |

(Continued)

OTHER PUBLICATIONS

West, Anthony R., Solid State Chemistry and its Applications, Wiley, New York, 1988, pp. 358 & 365.*
Bernard Testa "Predicting drug metabolism: Concepts and challenges" Pure and Applied Chemistry 2004, vol. 76, No. 5, pp. 907-914.*
Alibhai, et al (2006) "Prevention and Management of Osteoporosis in Men Receiving Androgen Deprivation Therapy: A Survey of Urologists and Radiation Oncologists." Urology, vol. 68, pp. 126-131.
Angelo, et al (1968) Nouvelles solutions ioniques radiclaires et leur emplol., Bull de la Soc. Chim. De France, No. 9, 3855-3856.
Berthelot, et al (1985) Stereochimie des complexes du chlorure d'iode avec les bases carbonylees, Can. J. Chem, vol. 63, 1985, pp. 958-962.

(Continued)

*Primary Examiner* — Shailendra Kumar
(74) *Attorney, Agent, or Firm* — Pearl Cohen Zedek Latzer Baratz, LLP; Mark S. Cohen

(57) ABSTRACT

The present invention relates to methods of treating androgen deprivation therapy (ADT) induced hot flashes and severe hot flashes in a subject.

24 Claims, 23 Drawing Sheets

(56) References Cited

FOREIGN PATENT DOCUMENTS

| WO | WO 96/07402 | 3/1996 |
|---|---|---|
| WO | WO 97/30047 | 8/1997 |
| WO | WO 01/44161 | 6/2001 |
| WO | WO 02/28853 | 4/2002 |
| WO | WO 2004/009552 | 1/2004 |
| WO | WO 2004/026823 | 4/2004 |

OTHER PUBLICATIONS

Chadwick, et al (2005) "Identification of pathway-selective estrogen receptor ligands that inhibit NF-κB transcriptional activity." PNAS, vol. 102, No. 7, pp. 2543-2548.
Fotsis, et al (1993) "Genistein, a Dietary-Derived Inhibitor of in vitro Angiogensis." PNAS, vol. 90, pp. 2690-2694.
Grease, et al (2001) Photochemical Synthesis of N-Arylbenzophenanthridine Selective Estrogen Receptor Modulators (SERMS). J. Med. Chem. 44, 2857-2860.
Gustafson (2006) "ERβ scientific visions translate to clinical uses." Climacteric, vol. 9, pp. 156-160.
Harris (2006) "The unexpected science of estrogen receptor-β selective agonists: a new class of anti-inflammatory agents?" Nuclear Receptor Signaling, vol. 4, 012-016.
Harris (2006) "Estrogen Receptor-β: Recent Lessons from in Vivo Studies." Molecular Endocrinology, vol. 21, No. 1, pp. 1-13.
Harris, et al (2006) "Evaluation of an Estrogen Receptor-β Agonist in Animal Models of Human Disease." Endocrinology, vol. 144, No. 10, pp. 4241-4249.
Hayashi, et al (1997) "Genistein, a Protein Tyrosine Kinase Inhibitor, Ameliorates Retinal Degeneration After Ischemia-Reperfusion Injury in a Rat." Investigative Ophthalmology and Visual Science, vol. 38, No. 6, pp. 1193-1202.
Heim, et al (2006) "They Phytoestrogen Genistein Enhances Osteogenesis and Represses Adipogenic Differentiation of Human Primary Bone Marrow Stromal Cells." Endocrinology, vol. 145, No. 2, pp. 848-859.
Yu, et al (2006) "Salutary effects of estrogen receptor-β agonist on lung injury after trauma-hemorrhage." Am. J. Physiol. Lung Cell Mol. Physiol., vol. 290, pp. L1004-L1009.
Ho, et al (2004) "Estrogens and Anti-Estrogens: Key Mediators of Prostat Carcinogenesis and New Therapeutic Candidates." Journal of Cellular Biochemistry, vol. 91, pp. 491-503.
Kai, et al (2004) "Soybean Isoflavones Eliminate Nifedipine-Induced Flushing of Tail Skin in Ovariectomized Mice." J Pharmacol. Sci., vol. 95, pp. 476-478.
Lutty, et al (1999) "Changes in Choriocapillaris and Retinal Pigment Epithelium (RPE) in Age-Related Macular Degeneration." Molecular Vision, vol. 5, No. 35, pages.
Morani, et al (2006) "Lung dysfunction causes systematic hypoxia in estrogen receptor β knockout (ERβ$^{-/-}$) mice." PNAS. vol. 103, No. 18, pp. 7165-7169.
Norman, et al (2006) "Benzopyrans Are Selective Estrogen Receptor β Agonists with Novel Activity in Models of Benign Prostate Hyperplasia." J Med. Chem., vol. 49, pp. 6155-6157.
Nakajima, et al (2001) "Normalization of Retinal Vascular Permeability in Experimental Diabetes with Genistein." Investigative Ophthalmology and Visual Science, vol. 42, No. 9, pp. 2110-2114.
Rhodes, et al (2005) "ERβ-selective SERMs produce mnemonic-enhancing effects in the inhibitory avoidance and water maze tasks." Neurobiology of Learning and Memory, vol. 85, pp. 183-191.
Safe, et al (2006) "The role of xenoestrogenic compounds in the development of breast cancer." Trends in Pharmacological Sciences, vol. 27, No. 8.
Shen, et al (2006) "Expression of Estrogen Receptors-α and -β in Bladder Cancer Cell Lines and Human Bladder Tumor Tissue." American Cancer Society.
Trotter, et al (2006) "Design and Synthesis of Novel Isoquinoline-3-nitrilies as Orally Bioavailable Kv1.5 Antagonists for the Treatment of Atrial Fibrillation." American Chemical Society.
Vivacqua, et al (2006) "The G Protein-Coupled Receptor GPR30 Mediates the Proliferative Effects Induced by 17β-Estradiol and Hydroxytamoxifen in Endometrial Cancer Cells." Molecular Endocrinology, vol. 20, No. 3, pp. 631-646.
Walf, et al (2006) "Aggression, mood and affect." Frontiers in Neuroendocrinology, vol. 27.
Xu, et al (2006) "Effects of genistein on angiotensin-converting enzyme in rats." Life Sciences, vol. 79, pp. 828-837.
Grimshaw, et al "Intramolecular Cyclisation during the reduction of 2-chloro-NN-diphenylbenzamides" Electrochemical Reactions, Part 20, vol. 22, 1977, p. 2456.
Kenneth et al., "The kinetics of the thermal rearrangement of phenyl benzanilimino ethers", Journal of the American Chemical Society, 1955, 77, 2205-9.
Chapman et al., "New method for preparing substituted diphenylamines", Journal of the Chemical Society, 1929, pp. 569-572.
Schroeter et al., "Dimolecular Anhydrides of Anthranilic Acid", Justis Liebigs Annalen der Chemie, 1909, 367, pp. 101-168.
Clark et al., "Synthetic studies on 5-(3,4-dimethoxyphenyl)-5,6-dihydrophenanthridin-6-ol, an analog of perloline", Australian Journal of Chemistry, 1982, 35(8), pp. 1645-1653.
Hoeft Eugen et al., "Reactions of nitrogen-containing compounds with molecular oxygen II. Partially hydrogenated, benxocondensed isoquinolines", justus Liebids Annalen de Chemie, 1966, 697, pp. 181-187.
Migel et al., "Estimate of the energy characteristics of the electronic-vibrational interactions in N-methylphenanthridone molecules" Zhurnal Fizicheskoi Khimii, 1986 62(9), pp. 2533-2537.
Hellwinkel et al., "Heterocyclic synthese via carbanionically induced rearrangement reactions", Tetrahedron, 1983, 39(12), 2073-84.
Datta et al., "Studies on Enamides. Part 4. Photochemical Investigations of N-Aroyldiphenylamines", Tetrahedron, 1990, 46(19), 6821-30.
Joseph et al., "Rearrangement of nitrones to amides using chlorosulfonyl isocyanate", Tetrahedron, 1986, 42(21), 5979-83.
Fong et al., "The effect of side chain confirmation on the carbon-13 substituent chemical shifts of N-substituted benzamides", Australian Journal of Chemistry, 1981, 34(6), 1205-1214.
Scherowsky et al., "Reactions of heterocyclic onium salts with electron-rich multiple bond systems", Chemische Berichte, 1983, 116(1), pp. 186-196.
El-Taweel et al., "Studies with polyfunctionally substituted heteroarenes: New synthesis of benzo[c]quinolinones and pyrano[3,2,c]quinoline derivatives", Bollettino Chimico Farmaceutico, 1998, 137(8), pp. 325-333.
Mintas Mhaden et al., "Sterically hindered N-aryl-2 (1H)-quinolones and N-aryl-6-(5H)-phenanthridinones: separation of enantiomers and barriers to racemization", Journal of the Chemical Society, Perkin Transactions 2: Physical Organic Chemistry (1972-1999) (4), 1990, pp. 619-624.
Derneter et al., "Dual fluorescence and intramolecular charge transfer with N-Phenylphenanthridinones", Journal of Physical Chemistry a, 2001, 105 (19), 4611-4621.
Moynehan et al.,t, Proceedings of the Chemical Society, Lodon 209, 1957.
Hey et al., "Internuclear cyclization. XIII. Decomposition of diazonium salts prepared from N-(0-aminobenzoyl) diphenylamines. New molecular rearrangement", Journal of the Chemistry Society, 1959, pp. 1563-1572.
Wolff, "Burger's Medicial Chemistry 4$^{th}$ Ed. Part I", Wiley: New York, 1979, 336-337.
Wolff, "Burger's Medicinal Chemistry 5$^{th}$ Ed. Part I", Wiley: 1996, pp. 975-977.
Banker et al., "Modern Pharmaceutics, 3 Ed." 1996, pp. 451 and 596.
West, "Solid state chemistry and its applications" Wiley, 1988, pp. 358 and 365.
Ohnmacht et al., "N-Aryl-3,3,3-trifluoro-2-hydroxy-2-methylpropanamides: potassium Channel Openers. Modifications on the Western Region", J. Med. Chem., 1996, 39, 4592-4601.
International Search Report of Application No. PCT/US06/45451; Date of Mailing Feb. 29, 2008.
Eurasian Search Report of Application No. 200801461; Date of Mailing Oct. 29, 2008.

International Search Report of Application No. PCT/US10/25032; Date of Mailing Apr. 8, 2010.
International Search Report of Application No. PCT/US08/04908; Date of Mailing Sep. 26, 2008.
Datti et al., "Studies on Enamides. Part-4: Photochemical Investigations of N-Aroyldiphenylamines", Tetrahedron, vol. 46, No. 19, 1990, pp. 6821-6830.
Heine et al., "The reactions of an o-Quinone Monoimide with some phenols", Journal of Organic Chemistry, vol. 55, No. 13, 1990, pp. 4039-4043.
Harris et al., "Sequential N-Arylation of primary amines as a route to alkyldiarylamines", Journal of Organic Chemistry, vol. 64, 1999, pp. 6019-6022.
Ohta et al., "Reaction of N,O-Diacylarylhydroxylamine with carbon nucleophiles", 1978, Tetrahedron Letters, pp. 1983-1986.
Piutti et al., "Azione dell'anidride ftalica sulla p- e m-ossidiffenilammina", Gazzetta Chimica Italiana, vol. 28, 1898, pp. 370-382.
Hellwinkel et al., "Ein bequemes Eintopfverfahren zur Synthese von 1,2-Benzisothiazol-1, 1-dioxiden", No. 5, 1989, pp. 394-395.
Lam et al., "Copper-promoted C-N bond cross-coupling with phenylstannane", Tetrahedron Letters 43, 2002, 3091-3094.
Smith (2008) *Current Prostate Reports*. 6:149-154.
Suzuki et al., (2008) *Int. J. Clin. Oncol.* 13: 401-410.
Sharifi, N. et al., (2005) *JAMA*. 294(2): 238-244.
Presti, J.C. Jr. (1996) JAMA. 275(15): 1153-6.
Tsourdi et al., 2008, *Fertility and Sterility* doi: 10.1016.
Supplementary European Search Report for European Patent Application No. EP 06 83 8432 dated Mar. 11, 2011.
European Search Report for European Patent Application No. 12 15 0818 dated Apr. 5, 2012.
Carter et al., John, Wiley & Sons, 2$^{nd}$ Edition, 361-365, 1981.
Australian Office Action for Australian Patent Application No. 2006318400 dated Oct. 25, 2011.
Australian Office Action dated Oct. 25, 2011 cited reference in AU Patent Application No. 2006318400, D19 CAS RN-79777-72-1, Benzamide, 2, 4-dichloro-N, N-bis (2-chlorophenyl), Chemical Library, Dec. 15, 2004.
Gilman et al., Synthesis of some 5, 10-dihydrophenazasiline derivatives, Journal of Organic Chemistry, 1961, vol. 26, pp. 2013-2017.
Australian Office Action cited dated Oct. 25, 2011 reference in AU Patent Application No. 2006318400, D21 RN 663217-19-14, Benzamide, N-[3, 5-bis (1,1-dimethylethyl)-4-hydroxyphenyl]-2-chloro-N-(4-methylphenyl), Chemical Library Supplier, Mar. 15, 2004.
Australian Office Action dated Oct. 25, 2011cited reference in AU Patent Application No. 2006318400, D22 CAS RN 409111-68-8, Benzeneacetic acid, 2, 2'-[4-chlorobenzoyll)iminio]bis-, dimethylester.
Grimshaw et al., Electrochemical Reactions, Part 20, Intramolecular Cyclization During the Reduction of 2-chloro-NN-Diphenylbenzamides, Journal of the Chemical Society, Perkin Transactions 1: Organic and Bio-Organic Chemistry (1972-1999) (1977), (22), 2456.
Birchall et al., Rearrangements of Diphenylamine Derivatives, II, Rearrangement o Some N-aroyldiphenylamines and the Intermolecular Character of the Reaction, Journal of the Chemical Society [Section] C: Organic 1968, vol. 23, pp. 2900-2904.
Jamison et al., Some Derivatives of Diphenylamine and a New Synthesis of N-arylanthranilic Acids and of Acridones, Journal of the Chemical Society, 1937, pp. 1954-1959.
Ivakhnenko et al., Synthesis and Transformations of Phenoxyl Biradicals, Zhurnal Organicheskoi Khimii, 1990, vol. 26(3), pp. 616-623.
Hey et al. Internuclear Cyclization, XIII, Decomposition of Diazonium Salts Rearrangement from N-(omicron-aminobenzoyl) Diphenylamines. New Molecular Rearrangement, Journal of the Chemical Society, 1959, pp. 1563-1572.
Tozer et al., Rearrangement of the o-Carbamyl Derivaties of Diphenly ether, Journal of the Chemical Society, 1938, pp. 2052-2056.
Chapman et al., Beckmann Change, I, The Spontaneous Rearrangement of oxime picryl ethers, Journal of the Chemical Society, 1933, pp. 806-811.
Australian Office Action dated Oct. 25, 2011 cited reference in AU Patent Application No. 2006318400, D31 CAS RN 300668-84-4, Benzamide, N-(3-bromophenyl_-N-(4-bromophenyl)-2-nitro, Chemical Library Supplier, Nov. 1, 2000.
Heine et al., The Reactions of an o-Quinone Monoimide with some phenols, Journal of Organic Chemistry, 1990, vol. 55(13), pp. 4039-4043.
Carter et al., Arylation with 1, 3-dinitroarnes and copper (I) tert-butoxide Scope and Limitations, Journal of Chemical Research, Synopses, 1985, vol. 5, pp. 136-137.
Froehlich et al., Process for Preparation of Anthranilamides, Ger (East), 1989, p. 7.
Australian Office Action for Australian Patent Application No. 2011226856 dated Dec. 23, 2011.
Hellwinkle et al., Carbanionically induced [1,3]-migrations of π-and Corrdinatively Unsaturated Groups, Chemische Berichte, 1983, vol. 116, No. 10, pp. 3375-3405.
Boltze et al., The Chemistry of Etofenamate, a Novel Anti-inflammatory Agent from the Series N-arylanthranilic Acid Derivatives, Arzneimittel-Forschung, 1977 vol. 27, No. 6B, pp. 1300-1312.
Grigorovskii et al., The Formation of 9-Chloroacridines from Diphenylamine-2-Carboxylic Acids and Phosphorus Oxychlorid, Zhurnal Prikladnoi Khimii, 1950, vol. 23, pp. 197-204.
Steigman et al., The Anhydrides of N-aryl Anthranilic Acids II, Journal of Organic Chemistry, 1937, vol. 2, pp. 211-212.

* cited by examiner

* p<0.0001  **p<0.0001

* p<0.0001  **p<0.0001

ESTROGEN RECEPTOR LIGANDS AND METHODS OF USE THEREOF

CROSS-REFERENCE TO RELATED APPLICATIONS

This Application is a Continuation-In-Part Application of U.S. patent application Ser. No. 11/785,251, filed Apr. 16, 2007, now U.S. Pat. No. 8,158,828, and is a Continuation-In-Part of U.S. patent application Ser. No. 11/604,884, filed Nov. 28, 2006, which claim priority from U.S. Provisional Application Ser. No. 60/739.898, filed Nov. 28, 2005 and this Application claims priority from U.S. Provisional Application Ser. No. 61/261.669, filed Nov. 16, 2009; and from U.S. Provisional Application Ser. No. 61/168,983, filed Apr. 14, 2009; and from U.S. Provisional Application Ser. No. 61/154,707, filed Feb. 23, 2009; all of which are hereby incorporated by reference in their entirety.

FIELD OF THE INVENTION

The present invention relates to methods of treating androgen deprivation therapy (ADT) induced hot flashes and severe hot flashes in a subject.

BACKGROUND OF THE INVENTION

Estrogens refer to a group of endogenous and synthetic hormones that are important for and used for tissue and bone maintenance. Estrogens are endocrine regulators in the cellular processes involved in the development and maintenance of the reproductive system. The role of estrogens in reproductive biology, the prevention of postmenopausal hot flashes, and the prevention of postmenopausal osteoporosis are well established. Estradiol is the principal endogenous human estrogen, and is found in both women and men.

The biological actions of estrogens and antiestrogens are manifest through two distinct intracellular receptors, estrogen receptor alpha (ERα) and estrogen receptor beta (ERβ). Endogenous estrogens are typically potent activators of both receptor subtypes. For example estradiol acts as an ERα agonist in many tissues, including breast, bone, cardiovascular and central nervous system tissues. Selective estrogen receptor modulators commonly act differently in different tissues. For example, a SERM may be an ERα antagonist in the breast, but may be a partial ERα agonist in the uterus, bone and cardiovascular systems. Compounds that act as estrogen receptor ligands are, therefore, useful in treating a variety of conditions and disorders.

Prostate cancer is one of the most frequently diagnosed noncutaneous cancers among men in the US and is the second most common cause of cancer deaths with over 180,000 new cases and almost 29,000 deaths expected this year. Patients with advanced prostate cancer undergo androgen deprivation therapy (ADT), typically either by luteinizing hormone releasing hormone (LHRH) agonists or by bilateral orchiectomy. Androgen deprivation therapy not only reduces testosterone, but estrogen levels are also lower since estrogen is derived from the aromatization of testosterone, which levels are depleted by ADT. Androgen deprivation therapy-induced estrogen deficiency causes significant side effects which include hot flushes, gynecomastia and mastalgia, bone loss, decreases in bone quality and strength, osteoporosis and life-threatening fractures, adverse lipid changes and higher cardiovascular disease and myocardial infarction, and depression and other mood changes. It is believed that many of the estrogen deficiency side effects of ADT are mediated by ERα.

Leuprolide acetate (Lupron®) is a synthetic nonapeptide analog of naturally occurring gonadotropin-releasing hormone (GnRH or LH-RH). Leuprolide acetate is an LH-RH superagonist that eventually suppresses LH secretion by the pituitary. Leuprolide acetate acts as a potent inhibitor of gonadotropin secretion, resulting in suppression of ovarian and testicular steroidogenesis. In humans, administration of leuprolide acetate results in an initial increase in circulating levels of luteinizing hormone (LH) and follicle stimulating hormone (FSH), leading to a transient increase in levels of the gonadal steroids (testosterone and dihydrotestosterone in males, and estrone and estradiol in premenopausal females). However, continuous administration of leuprolide acetate results in decreased levels of LH and FSH. In males, testosterone is reduced to castrate levels (below 50 ng/dL). In premenopausal females, estrogens are reduced to postmenopausal levels. Testosterone is a known stimulus for cancerous cells of the prostate. Suppressing testosterone secretion or inhibiting the actions of testosterone is thus a necessary component of prostate cancer therapy. Leuprolide acetate can be used for LH suppression, which is the reduction and lowering of serum testosterone to castrate levels to treat prostate cancer.

Prior to the introduction of LHRH agonists, castrate testosterone levels were achieved by increasing estrogen activity in the pituitary via estrogens, primarily diethylstilbestrol (DES). DES was equally effective as LHRH agonists at suppressing testosterone to castrate levels. Patients treated with DES did not have hot flashes or bone loss, but did have gynecomastia at higher rates than ADT with LHRH agonists. Unfortunately, highly potent, pure estrogens, like DES and estradiol, are often associated with a high risk of severe cardiovascular and thromboembolic complications which have limited their clinical use.

The compounds of this invention suppress testosterone levels to castrate levels which may be used to treat prostate cancer, while preventing the increased risk of thrombotic events, and without causing bone loss, hot flashes and/or gynecomastia.

SUMMARY OF THE INVENTION

In another embodiment, the present invention provides a method of treating androgen deprivation therapy (ADT) induced hot flashes in subject, the method comprising the step of administering to said subject a therapeutically effective amount of a compound of formula I, or its isomer, pharmaceutical acceptable salt, N-oxide, pharmaceutical product, polymorph, hydrate or any combination thereof.

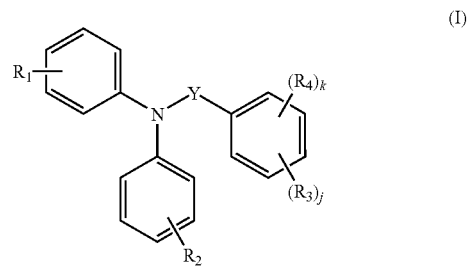

wherein
Y is C(O) or $CH_2$;
$R_1$, $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-NR$_5$R$_6$ or O-Alk-heterocycle in which the heterocycle is a 3-7 membered substituted or unsubstituted heterocyclic ring, optionally aromatic;

R$_3$, R$_4$ are independently hydrogen, halogen, hydroxyalkyl, hydroxyl, alkoxy, cyano, nitro, CF$_3$, NHCOR, N(R)$_2$, sulfonamide, SO$_2$R, alkyl, haloalkyl, aryl or protected hydroxyl;

R is alkyl, hydrogen, haloalkyl, dihaloalkyl, trihaloalkyl, CH$_2$F, CHF$_2$, CF$_3$, CF$_2$CF$_3$, aryl, phenyl, halogen, alkenyl, CN, NO$_2$, or OH;

R$_5$ and R$_6$ are independently hydrogen, phenyl, an alkyl group of 1 to 6 carbon atoms, a 3 to 7 membered cycloalkyl, a 3 to 7 membered heterocycle, a 5 to 7 membered aryl; or R$_5$ and R$_6$ form a 3 to 7 membered ring with the nitrogen atom;

j and k are independently 1-4;

Alk is linear alkyl of 1-7 carbons, branched alkyl of 1-7 carbons, or cyclic alkyl of 3-8 carbons.

In another embodiment, the present invention provides a method of reducing the incidence of, suppressing, or inhibiting androgen deprivation therapy (ADT) induced hot flashes in a subject, the method comprising the step of administering to said subject a therapeutically effective amount of a compound of formula I, or its isomer, pharmaceutical acceptable salt, N-oxide, pharmaceutical product, polymorph, hydrate or any combination thereof.

In another embodiment, the present invention provides a method of treating androgen deprivation therapy (ADT) induced severe hot flashes in subject, the method comprising the step of administering to said subject a therapeutically effective amount of a compound of formula I, or its isomer, pharmaceutical acceptable salt, N-oxide, pharmaceutical product, polymorph, hydrate or any combination thereof.

In another embodiment, the present invention provides a method of reducing the incidence of, suppressing or inhibiting androgen deprivation therapy (ADT) induced severe hot flashes in a subject, the method comprising the step of administering to said subject a therapeutically effective amount of a compound of formula I, or its isomer, pharmaceutical acceptable salt, N-oxide, pharmaceutical product, polymorph, hydrate or any combination thereof.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
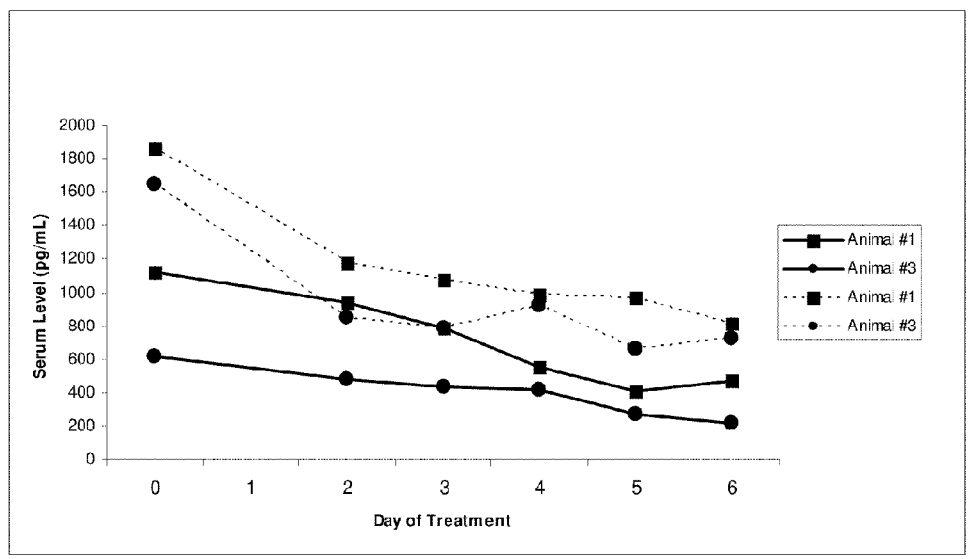
FIG. 1 depicts serum testosterone (solid line) and total androgen (dotted line) levels in intact male monkeys after daily 30 mg/kg oral administration of Compound IV (first dose on Day 0). (See Example 8.)

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, the compounds as described herein and/or compositions comprising the same may be used for treating androgen deprivation therapy (ADT) induced hot flashes or severe hot flashes in a male subject. In one embodiment the subject has prostate cancer. In another embodiment the subject has advanced prostate cancer.

In one embodiment, the compounds as described herein and/or compositions comprising the same may be used for reducing the incidence of, suppressing, reducing the severity or inhibiting androgen deprivation therapy (ADT) induced hot flashes or severe hot flashes in a male subject. In one embodiment the subject has prostate cancer. In another embodiment the subject has advanced prostate cancer.

In one embodiment, this invention provides a method of treating, reducing the incidence of, suppressing, reducing the severity or inhibiting androgen deprivation therapy (ADT) induced hot flashes or severe hot flashes in a male subject comprising administering a therapeutically effective amount of a compound or its isomer, pharmaceutical acceptable salt, pharmaceutical product, polymorph, hydrate or any combination thereof, represented by the structure of formula I:

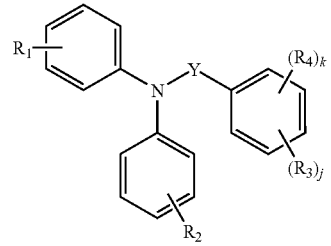

wherein

Y is C(O) or $CH_2$;

$R_1$, $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic;

$R_3$, $R_4$ are independently hydrogen, halogen, hydroxyalkyl, hydroxyl, alkoxy, cyano, nitro, $CF_3$, NHCOR, $N(R)_2$, sulfonamide, $SO_2R$, alkyl, haloalkyl, aryl or protected hydroxyl;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_5$ and $R_6$ are independently hydrogen, phenyl, an alkyl group of 1 to 6 carbon atoms, a 3 to 7 membered cycloalkyl, a 3 to 7 membered heterocycle, a 5 to 7 membered aryl; or $R_5$ and $R_6$ form a 3 to 7 membered ring with the nitrogen atom;

j and k are independently 1-4;

Alk is linear alkyl of 1-7 carbons, branched alkyl of 1-7 carbons, or cyclic alkyl of 3-8 carbons.

In another embodiment of the methods described herein, the compound of Formula I is represented by formula IA:

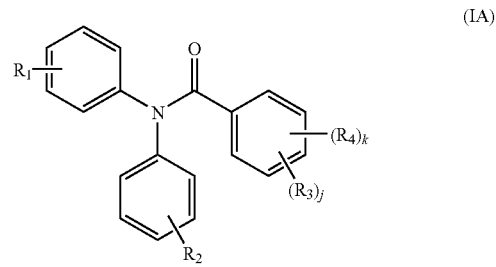

wherein $R_1$, $R_2$, $R_3$, $R_4$, j and k are as defined for Formula I.

In one embodiment, this invention provides a method of treating, reducing the incidence of, suppressing, reducing the severity or inhibiting androgen deprivation therapy induced hot flashes or severe hot flashes in a male subject comprising administering a therapeutically effective amount of a compound or its isomer, pharmaceutical acceptable salt, pharmaceutical product, polymorph, hydrate or any combination thereof, represented by a compound of formula II:

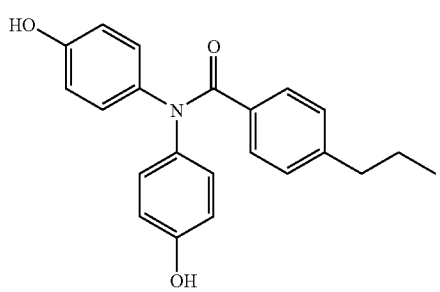

(II)

In one embodiment, this invention provides a method of treating, reducing the incidence of, suppressing, reducing the severity or inhibiting androgen deprivation therapy induced hot flashes or severe hot flashes in a male subject comprising administering a therapeutically effective amount of a compound or its isomer, pharmaceutical acceptable salt, pharmaceutical product, polymorph, hydrate or any combination thereof, represented by a compound of formula III:

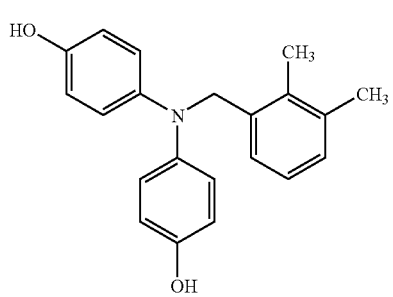

(III)

In one embodiment, this invention provides a method of treating, reducing the incidence of, suppressing, reducing the severity or inhibiting androgen deprivation therapy induced hot flashes or severe hot flashes in a male subject comprising administering a therapeutically effective amount of a compound or its isomer, pharmaceutical product, pharmaceutical acceptable salt, polymorph, hydrate or any combination thereof, represented by a compound of formula IV:

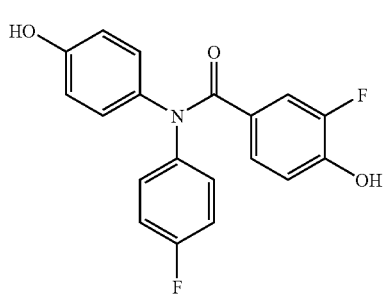

(IV)

In one embodiment, this invention provides a method of treating, reducing the incidence of, suppressing, reducing the severity or inhibiting androgen deprivation therapy induced hot flashes or severe hot flashes in a male subject comprising administering a therapeutically effective amount of a compound or its isomer, pharmaceutical acceptable salt, pharmaceutical product, polymorph, hydrate or any combination thereof, represented by a compound of formula V:

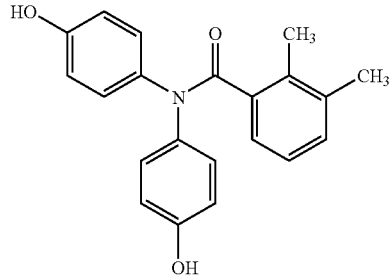

(V)

In one embodiment, this invention provides a method of treating, reducing the incidence of, suppressing, reducing the severity or inhibiting androgen deprivation therapy induced hot flashes or severe hot flashes in a male subject comprising administering a therapeutically effective amount of a compound or its isomer, pharmaceutical acceptable salt, pharmaceutical product, polymorph, hydrate or any combination thereof, represented by a compound of formula VI:

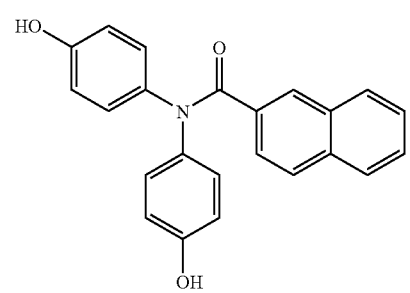

(VI)

In one embodiment, this invention provides a method of treating, reducing the incidence of, suppressing, reducing the severity or inhibiting androgen deprivation therapy induced hot flashes or severe hot flashes in a male subject comprising administering a therapeutically effective amount of a compound or its isomer, pharmaceutical acceptable salt, pharmaceutical product, polymorph, hydrate or any combination thereof, represented by a compound of formula VII:

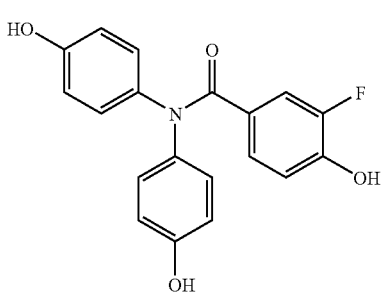

(VII)

In one embodiment, this invention provides a method of treating, reducing the incidence of, suppressing, reducing the severity or inhibiting androgen deprivation therapy induced hot flashes or severe hot flashes in a male subject comprising administering a therapeutically effective amount of a compound or its isomer, pharmaceutical acceptable salt, pharmaceutical product, polymorph, hydrate or any combination thereof, represented by a compound of formula VIII:

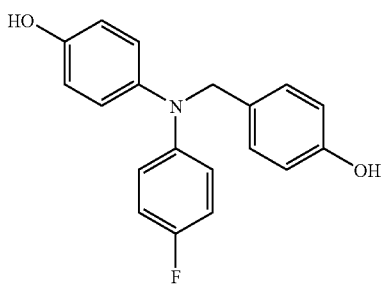

(VIII)

In one embodiment, this invention provides a method of treating, reducing the incidence of, suppressing, reducing the severity or inhibiting androgen deprivation therapy induced hot flashes or severe hot flashes in a male subject having prostate cancer, comprising administering a therapeutically effective amount of a compound or its isomer, pharmaceutical acceptable salt, pharmaceutical product, polymorph, hydrate or any combination thereof represented a compound of formula IX:

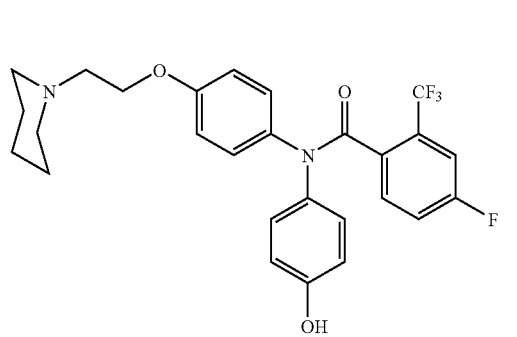

(IX)

In one embodiment, this invention provides a method treating, reducing the incidence of, suppressing, reducing the severity or inhibiting androgen deprivation therapy induced hot flashes or severe hot flashes in a male subject comprising administering a therapeutically effective amount of a compound or its isomer, pharmaceutical acceptable salt, pharmaceutical product, polymorph, hydrate or any combination thereof, represented by a compound of formula X:

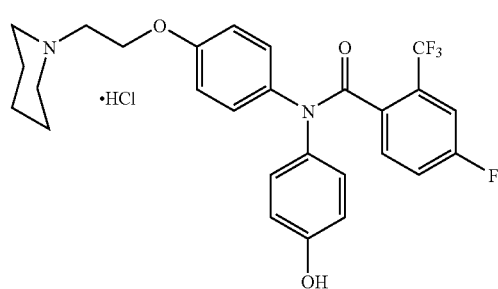

(X)

In one embodiment, this invention provides a method of treating, reducing the incidence of, suppressing, reducing the severity or inhibiting androgen deprivation therapy induced hot flashes or severe hot flashes in a male subject comprising administering a therapeutically effective amount of a compound or its isomer, pharmaceutical acceptable salt, pharmaceutical product, polymorph, hydrate or any combination thereof, represented by a compound of formula XI:

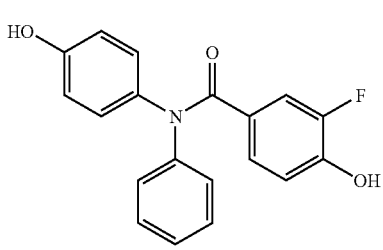

(XI)

In one embodiment, this invention provides a method of treating, reducing the incidence of, suppressing, reducing the severity or inhibiting androgen deprivation therapy induced hot flashes or severe hot flashes in a male subject comprising administering a therapeutically effective amount of a compound or its isomer, pharmaceutical acceptable salt, pharmaceutical product, polymorph, hydrate or any combination thereof, represented by a compound of formula XII:

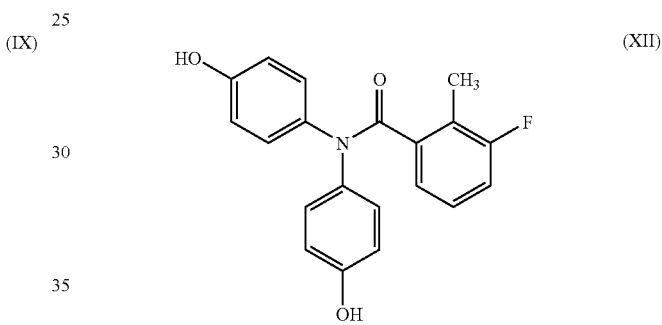

(XII)

In one embodiment, this invention provides a method of treating, reducing the incidence of, suppressing, reducing the severity or inhibiting androgen deprivation therapy induced hot flashes or severe hot flashes in a male subject comprising administering a therapeutically effective amount of a compound of formula IA, I-XII or its isomer, pharmaceutical acceptable salt, pharmaceutical product, polymorph, hydrate or any combination thereof. In another embodiment the male subject has prostate cancer. In another embodiment, the male subject has advanced prostate cancer. In another embodiment, the compound is Compound IV.

The term "advanced prostate cancer" refers to metastatic cancer having originated in the prostate, and having widely metastasized beyond the prostate such as the surrounding tissues to include the seminal vesicles, the pelvic lymph nodes, or bone, or to other parts of the body. Prostate cancer pathologies are graded with a Gleason grading from 1 to 5 in order of increasing malignancy. In another embodiment, patients with significant risk of progressive disease and/or death from prostate cancer should be included in the definition and that any patient with cancer outside the prostate capsule with disease stages as low as IIB clearly has "advanced" disease.

In one embodiment, this invention provides a method of treating, reducing the incidence of, suppressing, reducing the severity or inhibiting hot flashes or severe hot flashes in a male subject comprising administering a therapeutically effective amount of a compound of formula IA, I-XII or its isomer, pharmaceutical acceptable salt, pharmaceutical product, polymorph, hydrate or any combination thereof. In another embodiment, the compound is Compound W.

In one embodiment, the term "hot flash" refers to an episodic disturbance in body temperature, e.g., a sudden elevation in body temperature in a subject. In another embodiment, the disturbance is accompanied by perspiration. In one embodiment, the term "hot flashes" refers to a sudden feeling of heat in the upper part or all of the body, face and neck flush, red blotches appearing on the chest, back and arms, heavy sweating, cold shivering, etc, or any combination thereof. In one embodiment, the hot flash is experienced by a human subject, in another embodiment, a male subject. In one embodiment, the hot flash is a result of ADT. In another embodiment, the hot flash is not a result of ADT. In one embodiment, the hot flash is a side effect of prostate cancer treatment. In another embodiment, the hot flash is not a side effect of prostate cancer treatment.

The term "severe hot flashes" refers to a hot flash that causes profuse perspiration, generates intense heat, lasts longer, and interferes with ongoing activity. In one embodiment, severe hot flashes are characterized by problems of sleeping (often characterized as insomnia).

The methods of the invention for treating hot flashes can be used, in one embodiment, to treat hot flashes that result from, for example, menopause, tamoxifen acetate treatment, prostate cancer treatment, alcohol dehydrogenase deficiency, or carcinoid syndrome/pheochromocytoma. Each type of hot flash represents a separate embodiment of the present invention.

As provided herein, the results demonstrate that administration of a therapeutically effective amount of compound of formula I, such as, for example, compound IV, attenuated hot flashes in a subject.

In one embodiment, the compounds as described herein and/or compositions comprising the same may be used for lowering total serum testosterone levels in a male subject.

In one embodiment, the compounds as described herein and/or compositions comprising the same may be used for lowering total serum testosterone levels in a male subject wherein the lowering of total serum testosterone occurs by a reduction of serum luteinizing hormone (LH) levels.

In one embodiment, the compounds as described herein and/or compositions comprising the same may be used for lowering total serum testosterone levels in a male subject wherein the lowering of total serum testosterone is independent of a reduction of serum luteinizing hormone levels.

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by the structure of formula I:

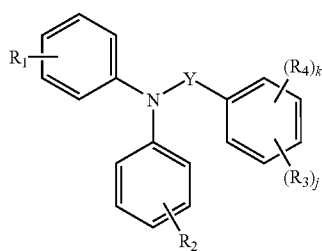

(I)

wherein

Y is C(O) or $CH_2$;

$R_1$, $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic;

$R_3$, $R_4$ are independently hydrogen, halogen, hydroxyalkyl, hydroxyl, alkoxy, cyano, nitro, $CF_3$, NHCOR, $N(R)_2$, sulfonamide, $SO_2R$, alkyl, haloalkyl, aryl or protected hydroxyl;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_5$ and $R_6$ are independently hydrogen, phenyl, an alkyl group of 1 to 6 carbon atoms, a 3 to 7 membered cycloalkyl, a 3 to 7 membered heterocycle, a 5 to 7 membered aryl; or $R_5$ and $R_6$ form a 3 to 7 membered ring with the nitrogen atom;

j and k are independently 1-4;

Alk is linear alkyl of 1-7 carbons, branched alkyl of 1-7 carbons, or cyclic alkyl of 3-8 carbons.

In additional embodiments of the methods described herein, the compound of Formula I is represented by formula IA:

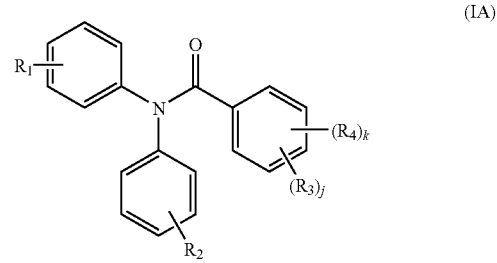

(IA)

wherein $R_1$, $R_2$, $R_3$, $R_4$, j and k are as defined for Formula I.

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula II:

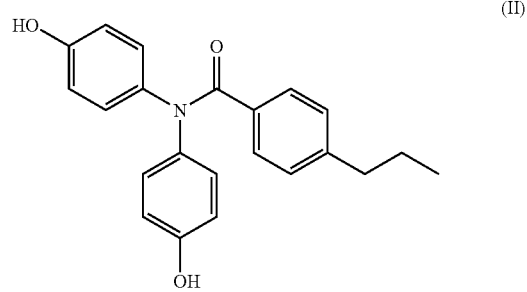 [SMILES: CCCc1ccc(C(=O)N(c2ccc(O)cc2)c2ccc(O)cc2)cc1]

(II)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula III:

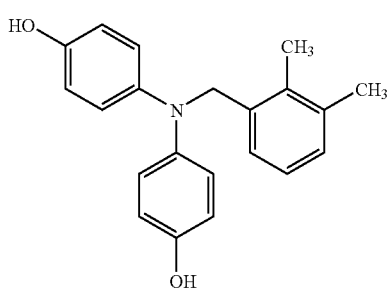
(III)

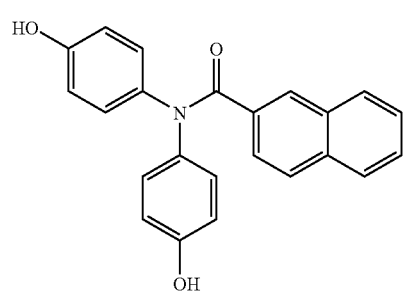
(VI)

In one embodiment, this invention provides a method of lowering total serum testosterone levels in a male subject comprising administering a therapeutically effective amount of a compound or its isomer, pharmaceutical product, pharmaceutical acceptable salt, polymorph, hydrate or any combination thereof, represented by a compound of formula IV:

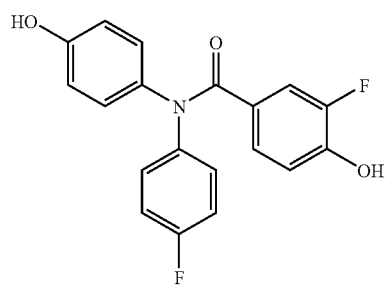
(IV)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula VII:

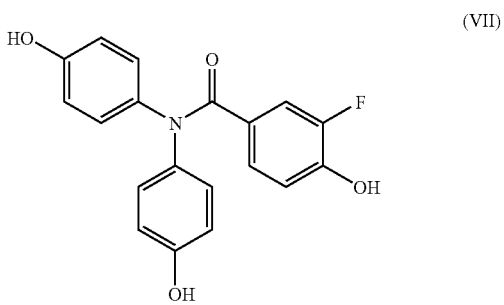 [SMILES: O=C(c1ccc(O)c(F)c1)N(c1ccc(O)cc1)c1ccc(O)cc1]
(VII)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula V:

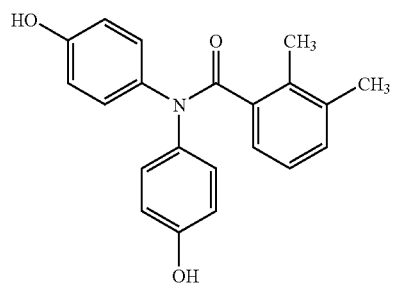
(V)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula VIII:

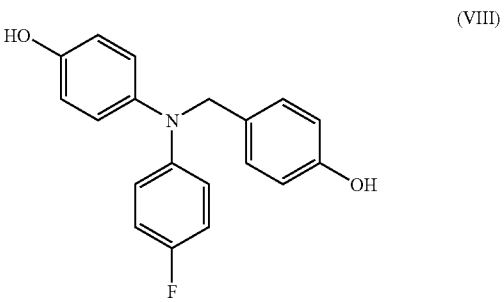 [SMILES: Oc1ccc(CN(c2ccc(O)cc2)c2ccc(F)cc2)cc1]
(VIII)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula VI:

In one embodiment, this invention provides a method of lowering total serum testosterone levels by reduction of luteinizing hormone (LH) levels in a male subject having prostate cancer, comprising administering a therapeutically effective amount of a compound or its isomer, pharmaceutical acceptable salt, pharmaceutical product, polymorph, hydrate or any combination thereof represented by a compound of formula IX:

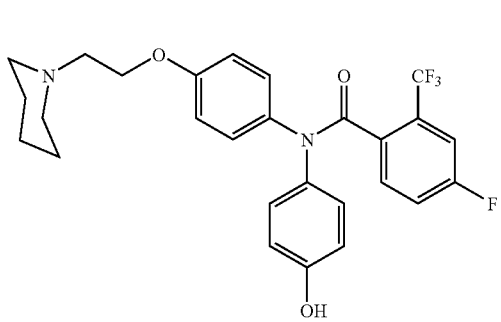

(IX)

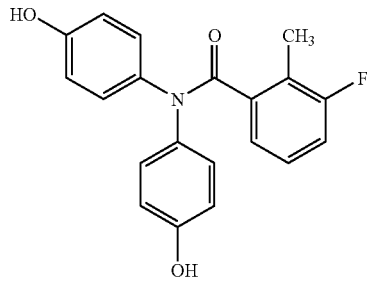

(XII)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula X:

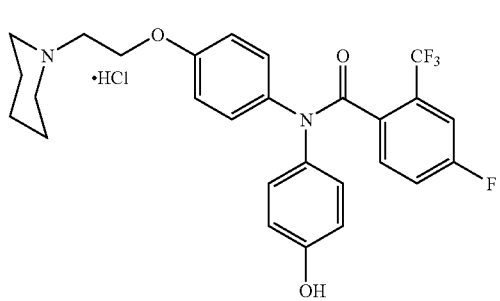

(X)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula XI:

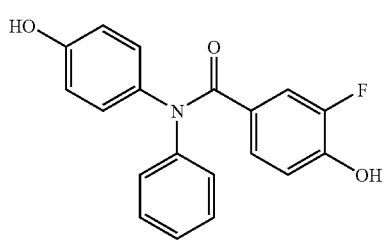

(XI)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula XII:

In one embodiment, this invention provides a method of lowering total serum testosterone levels in a male subject comprising administering a therapeutically effective amount of a compound of formula IA, I-XII or its isomer, pharmaceutical acceptable salt, pharmaceutical product, polymorph, hydrate or any combination thereof. In another embodiment the male subject has prostate cancer. In another embodiment, the total serum testosterone is lowered below about 100 ng/dL. In another embodiment, the total serum testosterone is lowered below about 50 ng/dL. In another embodiment, the total serum testosterone concentration is lowered below about 25 ng/dL.

In one embodiment, this invention provides a method of lowering total serum testosterone levels in a male subject comprising administering a therapeutically effective amount of a compound of formula IA, I-XII or its isomer, pharmaceutical acceptable salt, pharmaceutical product, polymorph, hydrate or any combination thereof, wherein the lowering of total serum testosterone occurs by a reduction of serum luteinizing hormone (LH) levels. In another embodiment the male subject has prostate cancer. In another embodiment, the total serum testosterone is lowered below about 100 ng/dL. In another embodiment, the total serum testosterone is lowered below about 50 ng/dL. In another embodiment, the total serum testosterone concentration is lowered below about 25 ng/dL.

In one embodiment, this invention provides a method of lowering free serum testosterone levels in a male subject comprising administering a therapeutically effective amount of a compound of formula IA, I-XII or its isomer, pharmaceutical acceptable salt, pharmaceutical product, polymorph, hydrate or any combination thereof, wherein the lowering of free serum testosterone occurs by a reduction of serum luteinizing hormone (LH) levels. In another embodiment the male subject has prostate cancer.

In one embodiment, this invention provides a method of lowering total serum testosterone levels in a male subject comprising administering a therapeutically effective amount of a compound of formula IA, I-XII or its isomer, pharmaceutical acceptable salt, pharmaceutical product, polymorph, hydrate or any combination thereof, wherein the lowering of total serum testosterone is independent of a reduction of serum luteinizing hormone (LH) levels. In another embodiment the male subject has prostate cancer. In another embodiment, the total serum testosterone is lowered below about 100 ng/dL. In another embodiment, the total serum testosterone is lowered below about 50 ng/dL. In another embodiment, the total serum testosterone concentration is lowered below about 25 ng/dL.

In one embodiment, this invention provides a method of lowering free serum testosterone levels in a male subject comprising administering a therapeutically effective amount of a compound of formula IA, I-XII or its isomer, pharmaceutical acceptable salt, pharmaceutical product, polymorph, hydrate or any combination thereof, wherein the lowering of free serum testosterone levels is independent of a reduction of serum luteinizing hormone levels. In another embodiment the male subject has prostate cancer.

In one embodiment, this invention provides methods of lowering total serum testosterone or free serum testosterone levels is a male subject, wherein said male subject has prostate cancer. In another embodiment said subject has advanced prostate cancer.

In one embodiment, the reduction in serum concentrations of testosterone is reversible and return to base line levels after treatment with the compounds of this invention.

Figure 23:
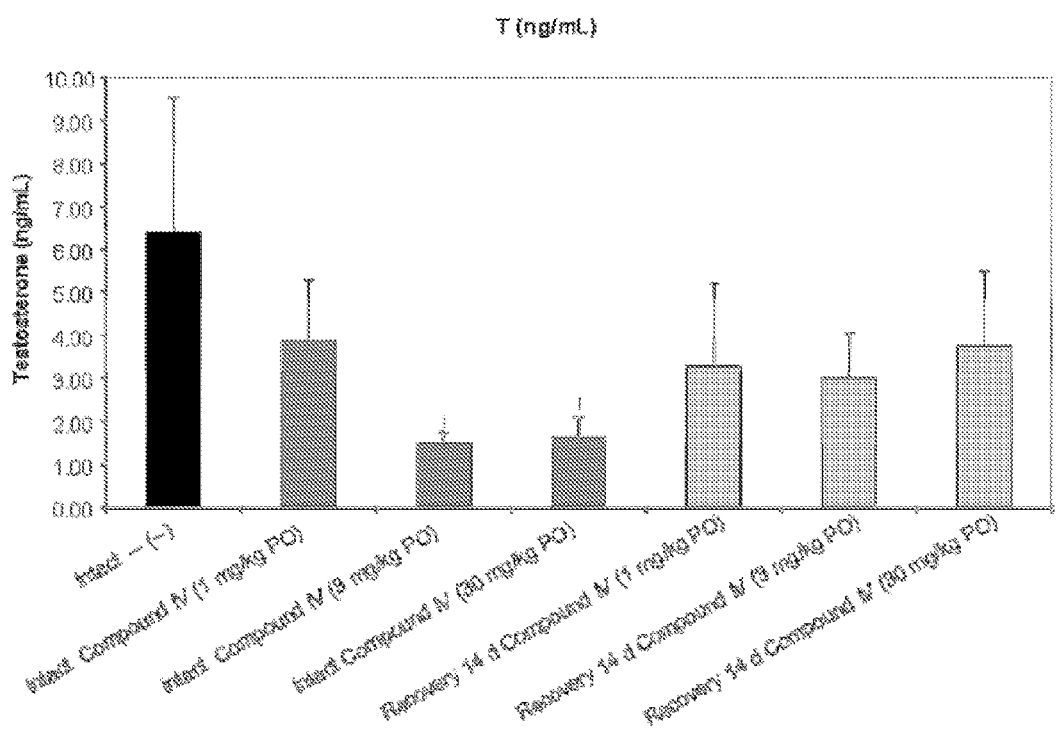
FIG. 23 depicts dose dependent serum testosterone levels (ng/mL) in intact rats after 14 days recovery of administering Compound IV. $^I$denotes P<0.05 vs Intact controls. (See Example 10.)

In another embodiment, serum concentrations of testosterone are reversible after treatment with Compound IV according to FIG. 23 and Example 10.

In one embodiment, this invention provides methods of lowering total serum testosterone levels in a male subject comprising administering a therapeutically effective amount of a compound of formula IA, I-XII or its isomer, pharmaceutical acceptable salt, pharmaceutical product, polymorph, hydrate or any combination thereof. In another embodiment, the total serum testosterone is lowered below about 100 ng/dL. In another embodiment, the total serum testosterone is lowered below about 50 ng/dL. In another embodiment, the total serum testosterone is lowered below about 25 ng/dL. In another embodiment, the total serum testosterone is lowered below about 75 ng/dL. In another embodiment, the total serum testosterone is lowered to about between 75 ng/dL-100 ng/dL. In another embodiment, the total serum testosterone is lowered to about between 50 ng/dL-75 ng/dL. In another embodiment, the total serum testosterone is lowered to about between 40 ng/dL-50 ng/dL. In another embodiment, the total serum testosterone concentration is lowered to about between 25 ng/dL-50 ng/dL. In another embodiment, the total serum testosterone is lowered to about between 40 ng/dL-60 ng/dL.

Testosterone can be measured as "free" (that is, bioavailable and unbound) or as "total" (including the percentage which is protein bound and unavailable) serum levels. Men, without prostate cancer, older than 40 years demonstrate low testosterone levels having total testosterone level of less than 250 ng/dL (<8.7 nmol/L) or a free testosterone level of less than 0.75 ng/dL (<0.03 nmol/L).

In one embodiment, the methods of this invention provides a method of lowering total serum and/or free testosterone levels independent from reduction of luteinizing hormone (LH) levels or by reduction of LH levels in a male subject having prostate cancer. In another embodiment changes in testosterone levels should be a reduction from the level prior to treatment. In another embodiment, the total serum testosterone level is lowered below 100 ng/dL. In another embodiment, the total serum testosterone is lowered below 50 ng/dL. In another embodiment, the total serum testosterone is lowered below 25 ng/dL. In another embodiment, the free testosterone level is lowered below 2 ng/dL. In another embodiment, the free testosterone level is lowered below 1 ng/dL. In another embodiment, the free testosterone level is lowered below 0.5 ng/dL. In another embodiment, the free testosterone level is lowered below 0.25 ng/dL.

Methods of determining the free serum testosterone levels and total serum testosterone levels include monitoring the testosterone levels during the course of the treatment period by a blood test. Total testosterone is a combination of circulating testosterone bound to carrier proteins (albumin, SHBG, transcortin, transferrin) and the free/unbound hormone. Total testosterone levels may be affected by several factors including the level of protein in the blood that transports the hormone in the body, age, obesity and interferences associated with commonly used test methods.

Methods available to measure free testosterone (FT) can be complex (equilibrium dialysis and calculated free testosterone (CFT)) or simple (the commercial FT kit "Coat-A-Count") using an analog tracer. In another embodiment the measurement of total testosterone and free testosterone serum levels can be achieved by simultaneous measurement of total testosterone and SHBG (e.g. Irma-Count, DPC) and then a calculated free testosterone (CFT). In another embodiment the measurement of total testosterone and free testosterone is according to the knowledge of one skilled in the art.

In one embodiment, this invention provides a method of lowering total serum testosterone levels or free serum testosterone levels in a male subject comprising administering a therapeutically effective amount of a combination of one or more other forms of ADT and a compound of formula IA, I-XII or its isomer, pharmaceutical acceptable salt, pharmaceutical product, polymorph, hydrate or any combination thereof. In another embodiment, lowering of total or free serum testosterone occurs by a reduction of serum luteinizing hormone (LH) level. In another embodiment, lowering total or free serum testosterone levels is independent of a reduction of serum luteinizing hormone levels.

The methods of this invention comprise administering a combination of other forms of ADT and a compound of this invention. In one embodiment, other forms of ADT include a LHRH agonist. In another embodiment the LHRH agonist includes Leuprolide acetate (Lupron®)(U.S. Pat. Nos. 5,480, 656; 5,575,987; 5,631,020; 5,643,607; 5,716,640; 5,814,342; 6,036,976 which are all incorporated by reference herein) or goserelin acetate (Zoladex®) (U.S. Pat. Nos. 7,118,552; 7,220,247; 7,500,964 which are all incorporated by reference herein). In one embodiment, other forms of ADT include an LHRH antagonist. In another embodiment, the LHRH antagonist includes degarelix. In one embodiment, other forms of ADT include anti-androgens. In another embodiment the anti-androgens include bicalutamide, flutamide, finasteride, dutasteride, MDV3100, nilutamide, chlormadinone, or any combination thereof.

In one embodiment, the methods of this invention comprise administering a therapeutically effective amount of an anti-androgen and a compound of this invention. In one embodiment, the methods of this invention comprise administering a therapeutically effective amount of an LHRH agonist and a compound of this invention. In one embodiment, the methods of this invention comprise administering a therapeutically effective amount of an anti-androgen, LHRH agonist and a compound of this invention.

In one embodiment, this invention provides a method for lowering total serum testosterone levels and/or free testosterone levels by reduction of luteinizing hormone (LH) levels or independent of reduction of luteinizing hormone levels in a male subject having prostate cancer for the purpose of producing androgen deprivation therapy (ADT) comprising administering a therapeutically effective amount of a compound of formula IA, I-XII. In another embodiment, the compound is Compound W.

In another embodiment, this invention provides a method for androgen deprivation therapy (ADT) in a subject, comprising administering a therapeutically effective amount of a compound of formula IA, I-XII or its isomer, pharmaceutical acceptable salt, pharmaceutical product, polymorph, hydrate or any combination thereof. In another embodiment, said subject has prostate cancer. In another embodiment, the compound is Compound IV.

In another embodiment, ADT is used for treating prostate cancer, for delaying the progression of prostate cancer, or for preventing and/or treating the recurrence of prostate cancer.

In one embodiment, this invention provides a method of treating prostate cancer, delaying the progression of prostate cancer, preventing and/or treating the recurrence of prostate cancer comprising administering a compound of this invention. In another embodiment, administering a compound of this invention in combination with LHRH analogs, reversible anti-androgens (such as bicalutamide or flutamide), anti-estrogens, anticancer drugs, 5-alpha reductase inhibitors, aromatase inhibitors, progestins, selective androgen receptor modulators (SARMS) or agents acting through other nuclear hormone receptors.

In one embodiment, the present invention provides a method of treating prostate cancer and reducing of total serum testosterone and/or free serum testosterone levels, by reducing LH levels or independent of reduction of LH levels, comprising administering a compound of formula IA, I-XIII. In another embodiment, administering Compound IV.

Androgen deprivation therapy not only reduces testosterone, but estrogen levels are also lower as estrogen is derived from the aromatization of testosterone. Androgen deprivation therapy-induced estrogen deficiency causes significant side effects which include hot flushes, gynecomastia and mastalgia, bone loss, decreases in bone quality and strength, osteoporosis, osteopenia, and life-threatening fractures, adverse lipid changes and higher cardiovascular disease and myocardial infarction, loss of libido, impotence, loss of muscle mass (sarcopenia), fatigue, cognitive dysfunction, and depression and other mood changes.

In other embodiments, the present invention provides a method of treating any disease, disorder, or symptom associated with ADT. In other embodiments, the present invention provides a method of treating any disease, disorder, or symptom associated with testosterone deprivation. Each disease, disorder, or symptom represents a separate embodiment of the present invention.

In one embodiment, this invention provides a method of lowering total serum testosterone levels in a male subject comprising administering a therapeutically effective amount of a compound of formula IA, I-XII or its isomer, pharmaceutical acceptable salt, pharmaceutical product, polymorph, hydrate or any combination thereof, wherein said administering said compounds of formula IA, I-XII or its isomer, pharmaceutical acceptable salt, pharmaceutical product, polymorph, hydrate or any combination thereof, prevents, suppresses, reduces the incidence, inhibits or treats side effects associated with androgen deprivation therapy (ADT) from occurring, wherein said subject has prostate cancer. In another embodiment the lowering of the total or free serum testosterone levels is by reducing LH levels or independent of reduction of LH levels.

In one embodiment, administering the compounds of this invention suppresses, reduces the incidence, inhibits or treats typical side effects associated with traditional androgen deprivation therapy (ADT) from occurring. In another embodiment, the subject has prostate cancer. Such prevention and/or reduction of side effects are relative to placebo or control group. In one embodiment, the typical side effects associated with traditional androgen deprivation therapy (ADT) include hot flashes, gynecomastia, decreased bone mineral density and increased bone fracture. In another embodiment, administering the compounds of this invention prevents hot flashes from occurring as would be found using traditional forms of androgen deprivation therapy (ADT). In another embodiment, administering the compounds of this invention prevents gynecomastia from occurring as would be found using traditional forms of androgen deprivation therapy (ADT). In another embodiment, administering the compounds of this invention prevents decreased bone mineral density (BMD) from occurring as would be found using traditional forms of androgen deprivation therapy (ADT). In another embodiment, administering the compounds of this invention prevents increased bone fracture from occurring as would be found using traditional forms of androgen deprivation therapy (ADT). In another embodiment, increased bone fracture is pathological fractures, non-traumatic fractures, vertebral fracture, non-vertebral fractures, new morphometric fractures, clinical fracture or a combination thereof In one embodiment, the term "traditional androgen deprivation therapy" is directed to orchiectomy (surgical castration) wherein the surgeon removes the testicles. In another embodiment, the term "traditional androgen deprivation therapy" is directed to administering luteinizing hormone-releasing hormone (LHRH) analogs: These drugs lower the amount of testosterone made by the testicles. Examples of LHRH analogs available in the United States include leuprolide (Lupron, Viadur, Eligard), goserelin (Zoladex), triptorelin (Trelstar), and histrelin (Vantas). In another embodiment, the term "traditional androgen deprivation therapy" is directed to administering anti-androgens: anti-androgens block the body's ability to use any androgens. Even after orchiectomy or during treatment with LHRH analogs, a small amount of androgens is still made by the adrenal glands. Examples of anti-androgens drugs include flutamide (Eulexin), bicalutamide (Casodex), and nilutamide (Nilandron). In another embodiment, the term "traditional androgen deprivation therapy" is directed to administering Luteinizing hormone-releasing hormone (LHRH) antagonists such as Abarelix (Plenaxis); Degarelix (Firmagon) is a new LHRH antagonist that was approved for use by the FDA in 2008 to treat advanced prostate cancer. In another embodiment, the term "traditional androgen deprivation therapy" is directed to administering 5α-reductase inhibitors such as finasteride (Proscar) and dutasteride (Avodart): 5α-Reductase inhibitors block the body's ability to convert testosterone to the more active androgen, 5α-dihydrotestosterone (DHT). In another embodiment, the term "traditional androgen deprivation therapy" is directed to administering inhibitors of testosterone biosynthesis such as ketoconazole (Nizoral). In another embodiment, the term "traditional androgen deprivation therapy" is directed to administering estrogens such as diethylstilbestrol or 17β-estradiol.

In one embodiment, the term "gynecomastia" refers to a benign enlargement of the male breast resulting from a proliferation of the glandular component of the breast, which may or may not be associated with pain. Gynecomastia is defined clinically by the presence of a rubbery or firm mass extending concentrically from the nipples. The condition known as pseudogynecomastia, or lipomastia, is characterized by fat deposition without glandular proliferation. Although gynecomastia is usually bilateral, it can be unilateral.

In one embodiment, the methods of this invention are directed to treating men with prostate cancer or advanced prostate cancer by reduction of testosterone without also causing bone loss and hot flashes. In another embodiment, the methods of this invention make use of compounds IA, I-XII, wherein the compounds has the potential to reduce testosterone, a primary stimulus for prostate cancer, without also causing certain side effects such as bone loss and hot flashes which are common with current androgen deprivation therapies (ADT) for prostate cancer.

In another embodiment, Table 8 (Example 11) hereinbelow demonstrate reduction of testosterone without also causing bone loss by administering Compound IV.

In one embodiment, the methods provided herein and/or utilizing the compounds provided herein, are effective in providing feedback on the hypothalamus-pituitary-testicular axis (HPT axis). Feedback refers to the ability of a substance produced in one organ or tissue to regulate the activity of another organ or tissue that affects its own activity. In one embodiment, feedback on the hypothalamus-pituitary-testicular axis (HPT axis) results in reduction of LH levels. In one embodiment, feedback on the hypothalamus-pituitary-testicular axis (HPT axis) results in reduction of total serum testosterone levels. In one embodiment, feedback on the hypothalamus-pituitary-testicular axis (HPT axis) results in reduction of free serum testosterone levels. In one embodiment, feedback on the hypothalamus-pituitary-testicular axis (HPT axis) results in reduction of serum, tissue or tumor levels of androgens.

The hypothalamic-pituitary-testicular (HPT) axis refers to the endocrine physiologic system that regulates hormone levels in the Hypothalmus, the Pituitary gland and the Testes. LHRH (luteinizing hormone releasing hormone) is released by the hypothalamus and stimulates the pituitary to synthesize and secrete LH and FSH (gonadotropins). LH and FSH then act on the testes to stimulate testosterone and sperm production. Testosterone then has a direct negative feedback effect on hypothalamic LHRH secretion and an indirect negative feedback effect on pituitary LH and FSH production. Estrogens, androgens and serum proteins (e.g., inhibin) also have a negative effect on LHRH secretion and secretion of LH and FSH.

The pituitary gland is one gland that controls the level of testosterone in the body. When the testosterone level is low, the pituitary gland releases the luteinizing hormone (LH). This hormone induces the testes to make more testosterone. The level of testosterone increases during puberty. The level of testosterone is the highest around age 20 to 40, and then gradually becomes less in older men. Women have a much smaller amount of testosterone in their bodies compared to men. But testosterone plays an important role throughout the body in both men and women. It affects the brain, bone and muscle mass, fat distribution, the vascular system, energy levels, genital tissues, and sexual function. Most of the testosterone in the blood is bound to a protein called sex hormone binding globulin (SHBG) or to another serum protein called albumin. Testosterone that is not bound (or "free") can also be clinically determined.

In another embodiment, lowering total serum testosterone or free serum testosterone levels independent of a reduction of serum luteinizing hormone levels is due to increase of sex hormone-binding globulin (SHBG). In another embodiment, lowering free testosterone levels independent of a reduction of serum luteinizing hormone levels is due to increase of sex hormone-binding globulin (SHBG). In another embodiment, lowering total serum or free serum testosterone levels independent of a reduction of serum luteinizing hormone (LH) levels is due to inhibition of testosterone production or secretion by Leydig cells in testes. In another embodiment, lowering total serum or free serum testosterone levels independent of a reduction of serum luteinizing hormone (LH) levels is due to decrease of adrenal steroidogenesis.

In one embodiment, the compounds as described herein and/or compositions comprising the same may be used for reduction of luteinizing hormone (LH) levels. In another embodiment, the compounds and/or compositions of this invention may be used to reduce endogenous sex hormones.

Hydroxysteroid dehydrogenase (HSD) family members are involved in the conversion of circulating steroids. 17β-HSD5 converts androstenedione to testosterone and estrone to estradiol. In addition, it is also involved in prostaglandin synthesis. In one embodiment the compounds of this invention inhibit HSD specifically 17β-hydroxysteroid dehydrogenase 5 (17β-HSD5) inhibition. Such inhibition may be useful in ADT, by preventing the peripheral/extragonadal testosterone synthesis which may escape the HPT axis control and cause incomplete reduction of total or free serum testosterone or allow locally elevated intracellular testosterone levels, either of which could be detrimental in ADT.

Androgen deprivation therapy (ADT) achieved by LHRH agonist therapy, i.e., administering luteinizing hormone releasing hormone agonists (LHRH) or analogues thereof, results in an initial stimulation of gonadotropin release from the pituitary and testosterone production from the testes (termed "flare reaction"), followed by decrease of gonadotropin release and decrease of both testosterone and estrogen levels. The "flare reaction" caused by LHRH agonist therapy has a negative impact on treatment of prostate cancer, due to the increase of androgen/testosterone levels. In addition, LHRH therapy has been associated with increased risk of diabetes and cardiovascular disease (Smith (2008) *Current Prostate Reports*. 6:149-154).

In an effort to overcome the flare effects of LHRH therapy, antiandrogen monotherapy (bicalutamide, flutamide, chlormadinone), combined LHRH/antiandrogen therapy approaches, and LHRH antagonists (degarelix) have been suggested (Suzuki et al., (2008) *Int. J. Clin. Oncol.* 13: 401-410; Sharifi, N. et al., (2005) *JAMA*. 294(2): 238-244). Antiandrogen monotherapy does not reduce androgen levels in a subject. Bicalutamide antiandrogen monotherapy was shown to be less effective than ADT in prostate cancer patients with bone metastases. In addition, adverse effects observed with bicalutamide therapy include breast tenderness and breast enlargement (Gynecomastia and Mastodynia). (Suzuki et al., ibid) Additional risk with antiandrogen therapy includes increased liver transaminases. (Sharifi et al. ibid).

In one embodiment, the present invention provides a reduction of LH levels and thereby a reduction of total serum testosterone and/or free serum testosterone levels, without production of the "flare" effect, and while overcoming the adverse effects associated with estrogen deficit caused by testosterone reduction using traditional ADT methods. Methods/uses of the subject compounds provide tissue-selective estrogen activities that provide maintenance of bone tissue (agonist effect on bone tissue), decreased thrombic potential and/or hot flushes and/or lesser or neutral effects on breast tissue than estradiol or diethylstilbestrol.

In one embodiment compound IV shows agonist but no antagonistic effects (Examples 6 and 7) so compound IV would not cause increase in gonadotropins and testosterone.

In one embodiment, compound IV shows agonist activity (Examples 8-11) demonstrating a robust pharmacologic response for the reduction of serum hormones, testosterone and total androgens.

In one embodiment, the methods provided herein utilizing the compounds and/or compositions provided herein, are effective in reducing or eliminating bone resorptive effects caused by reduction of LH using traditional forms of ADT. In one embodiment, the methods provided herein and/or utilizing the compositions provided herein, are effective in reducing or eliminating bone resorptive effects caused by reduction of testosterone levels using traditional forms of ADT. In one embodiment, the methods provided herein utilizing the compositions provided herein, are effective in reducing or eliminating bone resorptive effects caused by reduction of estrogen as a result of LH level reduction. In one embodiment, the methods provided herein utilizing the compounds and/or compositions provided herein, prevent bone resorptive effects associated with LH level reduction using traditional forms of ADT. In one embodiment, the methods provided herein utilizing the compounds and/or compositions provided herein, prevent bone loss associated with endogenous LH, testosterone and/or estradiol reduction using traditional forms of ADT. In one embodiment, the methods provided herein utilizing the compounds and/or compositions provided herein, increase bone mass density (BMD) while providing LH level reduction. In one embodiment, the methods provided herein utilizing the compounds and/or compositions provided herein, increase percent bone volume while providing endogenous LH, testosterone and/or estradiol level reduction.

In some embodiments, this invention provides a method of avoiding and/or reducing thromboembolism by administering a compound of this invention or its isomer, pharmaceutical product, polymorph, hydrate or any combination thereof.

In one embodiment, the methods provided herein utilizing the compounds and/or compositions provided herein, are effective in breast tissue. In one embodiment, the methods provided herein utilizing the compounds and/or compositions provided herein, provide LH level reduction while preventing gynecomastia associated with LH level reduction achieved by traditional ADT.

In one embodiment, Example 13 discloses special toxicity studies wherein in vitro studies with human platelets showed that Compound IV had much lower procoagulatory activity than DES. Thus, Compound IV, an ER-selective agonist, should deliver the prostate cancer benefits of DES with lesser risk of thrombotic events than DES, and also deliver the benefits of an LHRH agonist or antagonist without causing bone loss, hot flash or adverse lipid profiles.

Diethylstilbestrol (DES) therapy alone or combined with other ADT showed DES prevented bone resorption in patients with prostate cancer. Although use of DES has been promoted as a therapy for prostate cancer, effects of DES on angiogenesis and malignancy are thought to be mediated by DES metabolites and are not thought to act through the estrogen receptor. In addition, dosage levels of DES administered for therapeutic uses present numerous adverse side effects including vascular disease, cardiovascular morbidity, thrombotic toxicity, gynecomastia, erectile dysfunction and decreased libido (Schen and Pitts, ibid and Presti, J. C. Jr. (1996) JAMA. 275(15): 1153-6).

In one embodiment, the present invention overcomes the negative side effects of LHRH agonist or antagonist therapy, alone or in combination with anti-androgens or DES. In another embodiment, methods of the subject invention provide androgen deprivation therapy without adverse estrogen deprivation side-effects, such as adverse bone related conditions, and without adverse estrogen stimulation side-effects, such as gynecomastia. In another embodiment, methods of the current invention provide for a reduction of LH levels and thereby a reduction of total and/or free serum testosterone levels, without production of the "flare" effect, while overcoming the adverse effects associated with estrogen deficit caused by LH reduction and overcoming the adverse effects associated with a general estrogen agonist increase observed with DES therapy. Methods/uses of the subject compounds provide tissue-selective estrogen activities thereby providing maintenance of bone tissue (agonist effect on bone tissue), decreased thrombic potential and neutral effects on breast tissue.

Antiestrogenic effects of traditional selective estrogen receptor modulators (SERMs) such as tamoxifen, toremifene and raloxifene at the hypothalamic level result in an increase of gonadotropin levels or an increase of LH levels in men, and thereby potentially resulting in an increase in the testosterone serum levels. (Tsouri et al., 2008, Fertility and Sterility doi: 10.1016) In contrast, the methods of this invention provide reduction of LH in a male subject comprising administering a compound of formula I-XII.

Additional Embodiments for Compound of Formula I

In one embodiment of the methods of this invention, Y of compound of formula I is C(O). In another embodiment Y is $CH_2$. In another embodiment $R_1$ and $R_2$ of the compound of formula I or IA are independently O-Alk-$NR_5R_6$ or O-Alk-heterocycle. In another embodiment the Alk of said O-Alk-heterocycle, O-Alk-$NR_5R_6$, -Alk-heterocycle and Alk-$NR_5R_6$ as described herein above are linear alkyl of 1-7 carbons, branched alkyl of 1-7 carbons, or cyclic alkyl of 3-8 carbons. In another embodiment, the alkyl is ethylene (—$CH_2CH_2$—). In another embodiment the Alk is methylene (—$CH_2$—). In another embodiment the Alk is propylene (—$CH_2CH_2CH_2$—). In another embodiment the Alk is 2-methylpropylene (—$CH_2CH(CH_3)CH_2$—).

In one embodiment of the methods of this invention $R_1$ of the compound of formula I or IA is in the para position. In one embodiment of the methods of this invention $R_1$ and $R_2$ of the compound of formula I or IA are different. In another embodiment of the methods of this invention $R_1$ and $R_2$ of the compound of formula I or IA are the same. In another embodiment of the methods of this invention $R_1$ of the compound of formula I or IA is

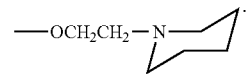

In another embodiment of the methods, $R_1$ of the compound of formula I or IA is hydroxyl. In another embodiment of the methods, $R_1$ of the compound of formula I or IA is alkoxy. In another embodiment of the methods, $R_1$ and $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic. In another embodiment of the methods, $R_1$ and $R_2$ of the compound of formula I or IA are independently halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic. In another embodiment of the methods, $R_2$ of the compound of formula I or IA is halogen. In another embodiment of the methods, $R_2$ of the compound of formula I or IA is F. In another embodiment of the methods, $R_2$ of the compound of formula I is Cl. In another embodiment of the methods, $R_2$ of the compound of formula I or IA is Br. In another embodiment of the methods, $R_2$ of the compound of formula I or IA is I. In another embodiment of the methods, $R_2$ of the compound of formula I or IA is hydroxyl. In another embodiment of the methods, $R_1$ and/or $R_2$ is $CF_3$. In another embodiment, $R_1$ and/or $R_2$ is $CH_3$. In another embodiment, $R_1$ and/or $R_2$ is halogen. In another embodiment, $R_1$ and/or $R_2$ is F. In another embodiment, $R_1$ and/or $R_2$ is Cl. In another embodiment, $R_1$ and/or $R_2$ is Br. In another embodiment, $R_1$ and/or $R_2$ is I. In another embodiment, $R_2$ of compound of formula I is in the para position.

In one embodiment of the methods of this invention, $R_3$ and $R_4$ of the compound of formula I or IA are the same. In another embodiment of the methods of this invention, $R_3$ and $R_4$ of the compound of formula I or IA are different. In another embodiment of the methods, j and k of the compound of formula I or IA are independently 1. In another embodiment of the methods, $R_3$ and $R_4$ of the compound of formula I or IA are independently halogen, haloalkyl, hydroxyl or alkyl. In another embodiment of the methods, $R_3$ and $R_4$ of the compound of formula I or IA are independently F. In another embodiment of the methods, $R_3$ and $R_4$ of the compound of formula I or IA are independently Br. In another embodiment of the methods, $R_3$ and $R_4$ of the compound of formula I or IA are independently Cl. In another embodiment, $R_4$ is in the para position. In another embodiment, $R_3$ is in the ortho position. In another embodiment, $R_3$ is in the meta position. In another embodiment, $R_3$ and/or $R_4$ is $CF_3$. In another embodiment, $R_3$ and/or $R_4$ is $CH_3$.

In one embodiment of the methods of this invention, $R_5$ and $R_6$ of the compound of formula I or IA form a 3 to 7 membered ring with the nitrogen atom. In another embodiment the ring is saturated or unsaturated ring. In another embodiment the ring substituted or unsubstituted ring. In another embodiment of the methods of this invention, $R_5$ and $R_6$ of the compound of formula I or IA form a piperidine ring with the nitrogen. In another embodiment of the methods, $R_5$ and $R_6$ of the compound of formula I or IA form a pyrazine ring with the nitrogen. In another embodiment of the methods, $R_5$ and $R_6$ of the compound of formula I or IA form a piperazine ring with the nitrogen. In another embodiment of the methods, $R_5$ and $R_6$ of the compound of formula I or IA form a morpholine ring with the nitrogen. In another embodiment of the methods, $R_5$ and $R_6$ of the compound of formula I or IA form a pyrrole ring with the nitrogen. In another embodiment of the methods, $R_5$ and $R_6$ of the compound of formula I or IA form a pyrrolidine. In another embodiment of the methods, $R_5$ and $R_6$ of the compound of formula I or IA form a pyridine ring with the nitrogen. In another embodiment the ring is substituted by halogen, alkyl, alkoxy, alkylene, hydroxyl, cyano, nitro, amino, amide, COOH or an aldehyde.

In another embodiment of the methods of this invention, $R_1$ of the compound of formula I or IA and $R_2$ of compound of the compound of formula I or IA are independently O-Alk-heterocycle or $OCH_2CH_2$-heterocycle. In another embodiment, the term "heterocycle" group refers, in one embodiment, to a ring structure comprising in addition to carbon atoms, sulfur, oxygen, nitrogen or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 4-8 membered ring. In another embodiment, the heterocycle group may be unsubstituted or substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring. In another embodiment, the heterocycle is piperidine. In another embodiment, the heterocycle is pyridine. In another embodiment, the heterocycle is piperidine, pyridine, furan, thiophene, pyrrole, pyrrolidine, pyrazine, piperazine or pyrimidine.

The term "cycloalkyl" refers to a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, (C3-C7) cycloalkyl groups, such as cyclopropyl, cyclobutyl, cyclopentyl, cyclohexyl, and cycloheptyl, and saturated cyclic and bicyclic terpenes and (C3-C7) cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two substituents. Preferably, the cycloalkyl group is a monocyclic ring or bicyclic ring.

The term "alkyl" refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. In another embodiment, the cyclic alkyl group has 3-8 carbons. In another embodiment, the cyclic alkyl group has 3-12 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted by a halogen, haloalkyl, hydroxyl, alkoxy carbonyl, amido, alkylamido, dialkylamido, nitro, amino, alkylamino, dialkylamino, carboxyl, thio and/or thioalkyl.

An "alkenyl" group refers, in another embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 2-4 carbons. Examples of alkenyl groups are ethenyl, propenyl, butenyl, cyclohexenyl, etc. The alkenyl group may be unsubstituted or substituted by a halogen, hydroxy, alkoxy carbonyl, amido, alkylamido, dialkylamido, nitro, amino, alkylamino, dialkylamino, carboxyl, thio and/or thioalkyl.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 4-8 membered ring. In another embodiment, the aryl group is a 4-12 membered ring(s). In another embodiment, the aryl group is a 6 membered ring. In another embodiment, the aryl group is a 5 membered ring. In another embodiment, the aryl group is 2-4 fused ring system.

An "aldehyde" group refers, in one embodiment to an alkyl, or alkenyl substituted by a formyl group, wherein the alkyl or alkenyl are as defined hereinabove. In another embodiment, the aldehyde group is an aryl, or phenyl group substituted by a formyl group, wherein the aryl is as defined hereinabove. Examples of aldehydes are: formyl, acetal, propanal, butanal, pentanal, benzaldehyde. In another embodiment, the aldehyde group is a formyl group.

A "haloalkyl" group refers, in another embodiment, to an alkyl group as defined above, which is substituted by one or more halogen atoms, e.g. by F, Cl, Br or I.

A "hydroxyl" group refers, in another embodiment, to an OH group. It is understood by a person skilled in the art that when $R_1$, $R_2$ or $R_3$ in the compounds of the present invention is OR, then R is not OH.

In one embodiment, the term "halogen" or "halo" refers to a halogen, such as F, Cl, Br or I.

In another embodiment, the phrase "phenol" refers to an alcohol (OH) derivative of benzene.

Reference to protected hydroxyl, in some embodiments, includes the incorporation of a substituent bonded to the oxygen moiety of the benzene ring, wherein the substituent may be readily removed. In some embodiments, phenolic protecting groups may comprise a: methyl ether (methoxy), alkyl ether (alkoxy), benzyl ether (Bn), methoxymethyl (MOM) ether, benzoyloxymethyl (BOM) ether, benzyl, carbobenzoxy, methoxyethoxymethyl (MEM) ether, 2-(trimethylsilyl)ethoxymethyl (SEM) ether, methylthiomethyl (MTM) ether, phenylthiomethyl (PTM) ether, azidomethyl ether, cyanomethyl ether, 2,2-dichloro-1,1-difluoroethyl ether, 2-chloroethyl ether, 2-bromoethyl ether, tetrahydropyranyl (THP) ether, 1-ethoxyethyl (EE) ether, phenacyl ether, 4-bromophenacyl ether, cyclopropylmethyl ether, allyl ether, propargyl ether, isopropyl ether, cyclohexyl ether, t-butyl ether, 2,6-dimethylbenzyl ether, 4-methoxybenzyl ether, o-nitrobenzyl ether, 2,6-dichlorobenzyl ether, 3,4-dichlorobenzyl ether, 4-(dimethylamino)carbonylbenzyl ether, 4-methylsulfinylbenzyl ether, 4-anthrylmethyl ether, 4-picolyl ether, heptafluoro-p-tolyl, tetrafluoro-4-pyridyl ether, trimethylsilyl (TMS) ether, t-butyldimethylsilyl (TBDMS) ether, t-butyldiphenylsilyl (TBDPS) ether, triisopropylsilyl (TIPS) ether, aryl formate, arylacetate, aryl levulinate, arylpivaloate, aryl benzoate, aryl 9-fluorencarboxylate, aryl methyl carbonate, 1-adamantyl carbonate, t-butyl carbonate, 4-methylsulfinylbenzyl carbonate, 2,4-dimethylpent-3-yl carbonate, aryl 2,2,2-trichloroethyl carbonate, aryl benzyl carbonate, aryl carbamate, dimethylphosphinyl ester (Dmp-OAr), dimethylphosphinothionyl ester (Mpt-OAr), diphenylphosphinothionyl ester (Dpt-OAr), aryl methanesulfonate, aryl toluenesulfonate or aryl 2-formylbenzenesulfonate.

In one embodiment, the methods of this invention make use of N,N-bis(4-hydroxyphenyl)-4-propylbenzamide (II) or its isomer, pharmaceutically acceptable salt, pharmaceutical product, polymorph, hydrate or any combination thereof. In another embodiment the methods of this invention make use of 4,4'-(2,3-dimethyl-benzylazanediyl)diphenol (III) or its isomer, pharmaceutically acceptable salt, pharmaceutical product, polymorph, hydrate or any combination thereof. In another embodiment the methods of this invention make use of 3-fluoro-N-(4-fluorophenyl)-4-hydroxy-N-(4-hydroxyphenyl)benzamide (IV) or its isomer, pharmaceutically acceptable salt, pharmaceutical product, polymorph, hydrate or any combination thereof. In another embodiment the methods of this invention make use of N,N-bis(4-hydroxyphenyl)-2,3-dimethylbenzamide (V) or its isomer, pharmaceutically acceptable salt, pharmaceutical product, polymorph, hydrate or any combination thereof. In another embodiment the methods of this invention make use of N,N-bis(4-hydroxyphenyl)-2-naphthylamide (VI) or its isomer, pharmaceutically acceptable salt, pharmaceutical product, polymorph, hydrate or any combination thereof. In another embodiment the methods of this invention make use of 3-fluoro-4-hydroxy-N,N-bis(4-hydroxyphenyl)-benzamide (VII) or its isomer, pharmaceutically acceptable salt, pharmaceutical product, polymorph, hydrate or any combination thereof. In another embodiment the methods of this invention make use of a 4-((4-fluorophenyl)(4-hydroxybenzyl)amino)phenol (VIII) or its isomer, pharmaceutically acceptable salt, pharmaceutical product, polymorph, hydrate or any combination thereof. In another embodiment the methods of this invention make use of a 4-fluoro-N-(4-hydroxy-phenyl)-N-[4-(2-piperidin-1-yl-ethoxy)-phenyl]-2-trifluoromethyl-benzamide (IX) or its isomer, pharmaceutically acceptable salt, pharmaceutical product, polymorph, hydrate or any combination thereof. In another embodiment the methods of this invention make use of a hydrochloride salt of IX (HCl salt of IX) or 4-fluoro-N-(4-hydroxy-phenyl)-N-[4-(2-piperidin-1-yl-ethoxy)-phenyl]-2-trifluoromethyl-benzamide hydrochloride (X) or its isomer, pharmaceutically acceptable salt, pharmaceutical product, polymorph, hydrate or any combination thereof. In another embodiment the methods of this invention make use of a 3-fluoro-4-hydroxy-N-(4-hydroxyphenyl)-N-phenyl-benzamide (XI) or its isomer, pharmaceutically acceptable salt, pharmaceutical product, polymorph, hydrate or any combination thereof. In another embodiment the methods of this invention make use of a 3-fluoro-N,N-bis-(4-hydroxyphenyl)-2-methyl-benzamide (XII) or its isomer, pharmaceutically acceptable salt, pharmaceutical product, polymorph, hydrate or any combination thereof.

In one embodiment the methods of this invention make use of "pharmaceutically acceptable salts" of the compounds, which may be produced, by reaction of a compound of this invention with an acid or base.

Suitable pharmaceutically-acceptable salts of amines of the compounds of the methods of this invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrate, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, carboxylates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates, gluconates, glutamates, glycolates, glucorates, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, nitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, pectinates, phenylpropionates, palmitates, pantothenates, polygalacturates, pyruvates, quinates, salicylates, succinates, stearates, sulfanilates, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or phenols may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In one embodiment, the methods of this invention make use of a pharmaceutically acceptable salt of the compounds of this invention. In one embodiment the methods of this invention make use of a pharmaceutically acceptable salt of compounds of formula IA, I-XII. In one embodiment, the methods of this invention make use of a salt of an amine of the compounds of formula IA, I-XIII of this invention. In one embodiment, the methods of this invention make use of a salt of a phenol of the compounds of formula IA, I-XIII of this invention.

In one embodiment the methods of this invention make use of a free base, free acid, non charged or non-complexed compounds of formula IA, I-XIII and/or its isomer, pharmaceutical product, hydrate, polymorph, or combinations thereof.

In some embodiments of this invention, the compounds of this invention comprise three phenyl groups which are held together by an amide bond. In one embodiment, the compounds of this invention are non-charged structures. In another embodiment, the compounds of this invention are free base structures. In another embodiment, the compounds of this invention are free acid structures. In another embodiment, the compounds of this invention are non-complexed structures. In another embodiment, the compounds of this invention are non-ionized structures. In another embodiment, the compounds of this invention are pharmaceutically acceptable salts. In another embodiment, some compounds of this invention include hydrochloride (HCl) salts.

In one embodiment, the methods of this invention make use of an isomer of a compound of formula IA, I-XIII. In one embodiment, the methods of this invention make use of a pharmaceutical product of a compound of formula IA, I-XIII. In one embodiment, the methods of this invention make use of a hydrate of a compound of formula IA, I-XIII. In one embodiment the methods of this invention make use of a polymorph of a compound of formula IA, I-XIII. In one embodiment the methods of this invention make use of a metabolite of a compound of formula IA, I-XIII. In another embodiment the methods of this invention make use of a composition comprising a compound of formula IA, I-XIII, as described herein, or, in another embodiment, a combination of isomer, metabolite, pharmaceutical product, hydrate, polymorph of a compound of formula IA, I-XIII.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the compound. In one embodiment, the term "isomer" is meant to encompass stereoisomers of the compound. The compounds of this invention possess an amide bond which may be in its cis or trans isomerization. It is to be understood that the present invention encompasses any optically-active, or stereroisomeric form, or mixtures thereof, and use of these for any application is to be considered within the scope of this invention.

In another embodiment, this invention further includes hydrates of the compounds. In one embodiment, the term "hydrate" refers to hemihydrate, monohydrate, dihydrate, trihydrate or others, as known in the art.

Synthetic Processes

Compounds of Formula IA may readily be prepared, for example, by reacting a substituted diphenyl amine with benzoic acid or benzoyl halide in the presence of a base to yield a benzamide. In one embodiment, the base is pyridine. In another embodiment, the benzoyl halide is benzoyl chloride. In another embodiment, a hydroxyl substituent is protected during the reaction between the diphenylamine and the benzoic acid or benzoyl halide. In another embodiment, the protecting group for the hydroxyl, optionally is removed in the last step. See also U.S. Publication No. 2009/00624231, which is incorporated by reference in its entirety.

For example, a compound of formula IA:

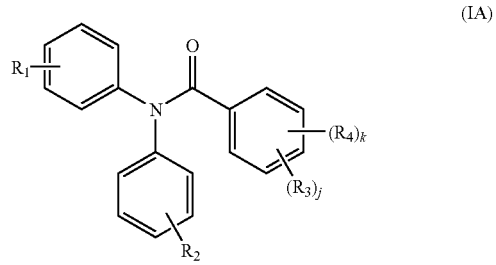

(IA)

wherein $R_1$, $R_2$, $R_3$ and $R_4$, j and k are as described above; may be prepared by a process that comprises reacting

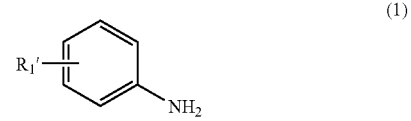

(1)

together with

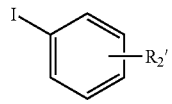 (2)

to yield

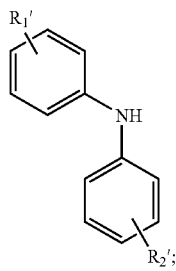 (3)

and the diphenyl amine (3) is reacted with

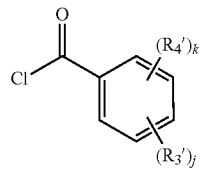 (4)

in the presence of a base to yield

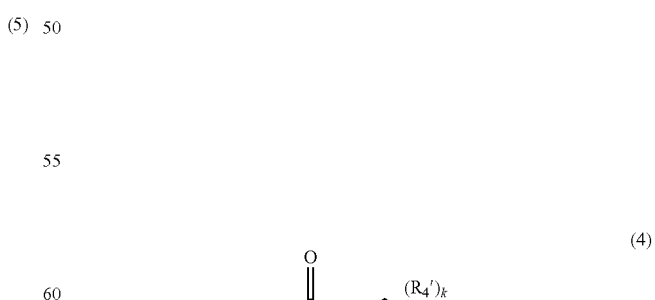 (5)

wherein if $R_1$, $R_2$, $R_3$ and $R_4$ are independently OH, O-Alk-$R_5R_6$ or O-Alk-heterocycle, then $R_1'$, $R_2'$, $R_3'$, $R_4'$ are protected hydroxyl group, wherein the protecting group is removed to obtain the free hydroxyl or optionally followed by reacting with Cl-Alk-heterocycle or Cl-Alk-$NR_5R_6$ to yield a compound of formula IA:

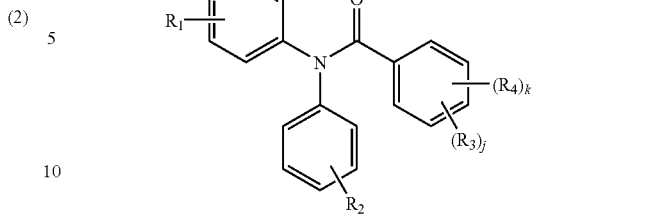 (IA)

wherein, if $R_1$, $R_2$, $R_3$ and $R_4$ are independently different than OH, O-Alk-$NR_5R_6$ or O-heterocycle then $R_1'$, $R_2'$, $R_3'$ and $R_4'$ are $R_1$, $R_2$, $R_3$ and $R_4$, respectively.

As another example, a process for the preparation of compound of Formula IA:

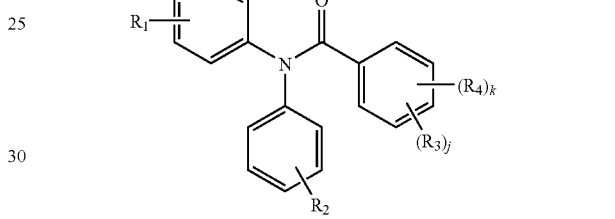 (IA)

wherein $R_1$, $R_2$, $R_3$ and $R_4$ are as described above, comprises reacting

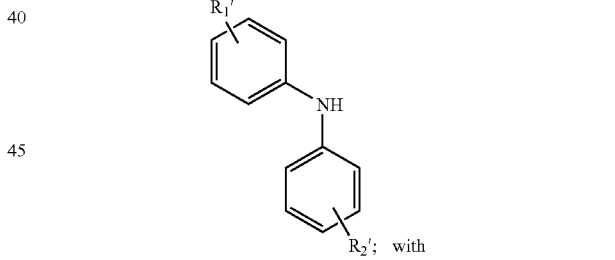 (3)

with (4)

in the presence of a base to yield

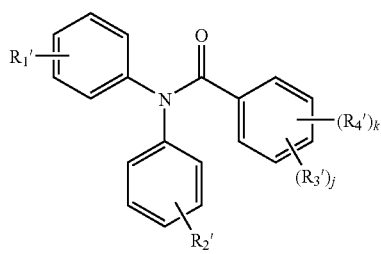

(5)

wherein if $R_1$, $R_2$, $R_3$ and $R_4$ are independently OH, O-Alk-$R_5R_6$ or O-Alk-heterocycle, then $R_1'$, $R_2'$, $R_3'$, $R_4'$ are protected hydroxyl group, wherein the protecting group is removed to obtain the free hydroxyl or optionally followed by reacting with Cl-Alk-heterocycle or Cl-Alk-$NR_5R_6$ to yield a compound of formula AI:

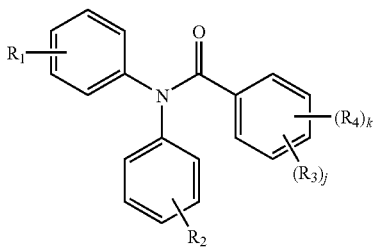

(IA)

wherein, if $R_1$, $R_2$, $R_3$ and $R_4$ are independently different than OH, O-Alk-$NR_5R_6$ or O-Alk-heterocycle then $R_1'$, $R_2'$, $R_3'$ and $R_4'$ are $R_1$, $R_2$, $R_3$ and $R_4$, respectively.

Figure 5:
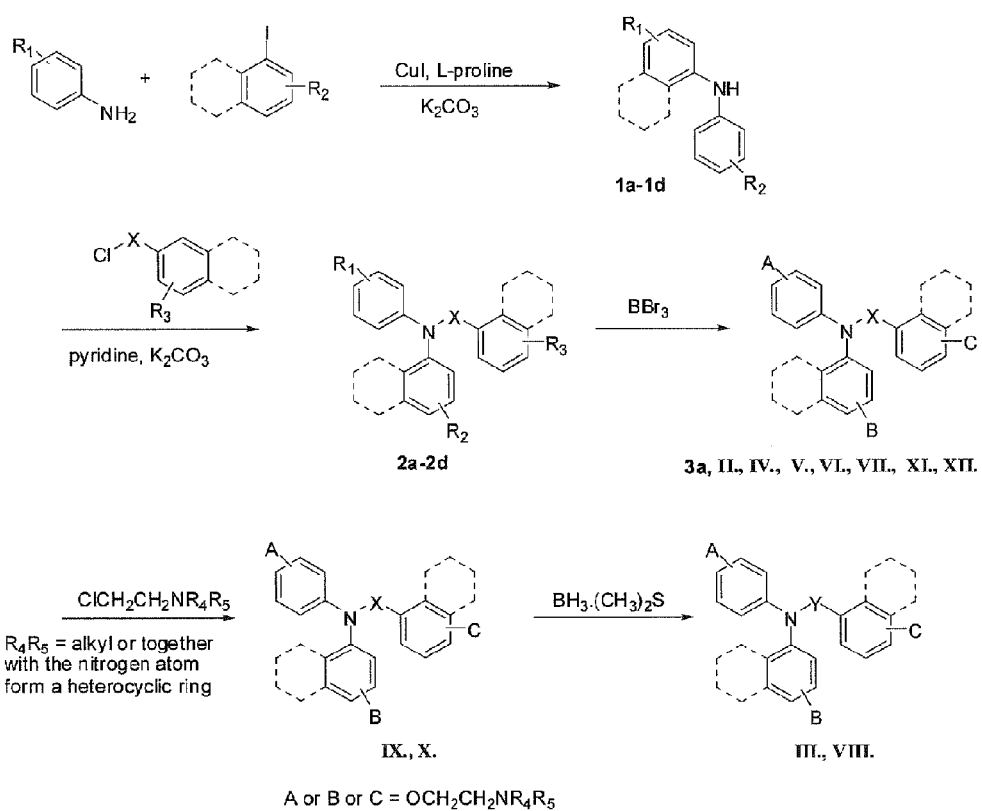
FIG. 5 Generic synthetic scheme for the preparation of Compounds II-XII. (See Example 1.)

In one example, Compound II is prepared according to Example 1, and FIG. 5.

In another example Compound III is prepared according to Example 1, and FIG. 5.

In a further example a compound of Formula IV:

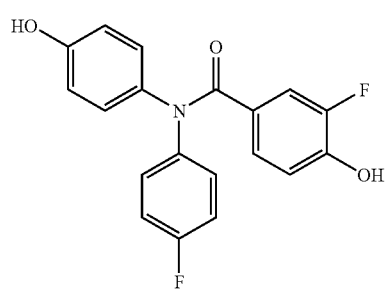

(IV)

May be prepared by reacting

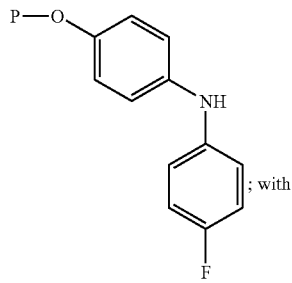

(11)

; with

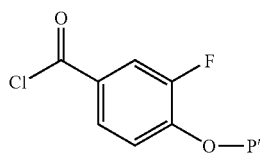

(12)

in the presence of a base to yield

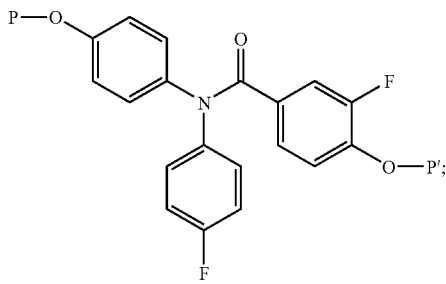

(13)

followed by deprotection of the protecting groups to yield Compound IV:

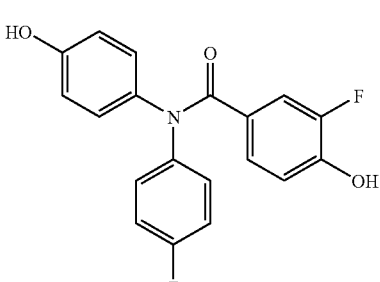

(IV)

wherein P and P' are the same or different protecting groups.

Figure 6:
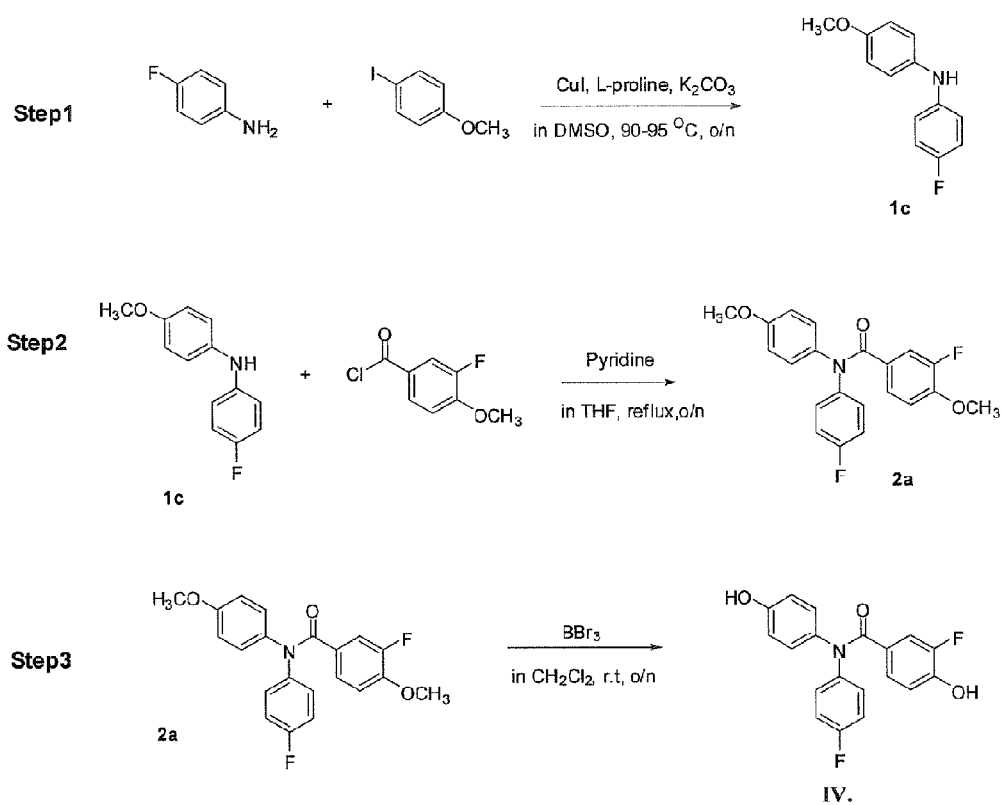
FIG. 6 Synthetic scheme for the preparation of Compound IV. (See Example 2.)

In one example, Compound IV is prepared according to Example 2, and FIG. 6.

In another example, Compound V is prepared according to Example 1, and FIG. 5.

Figure 7:
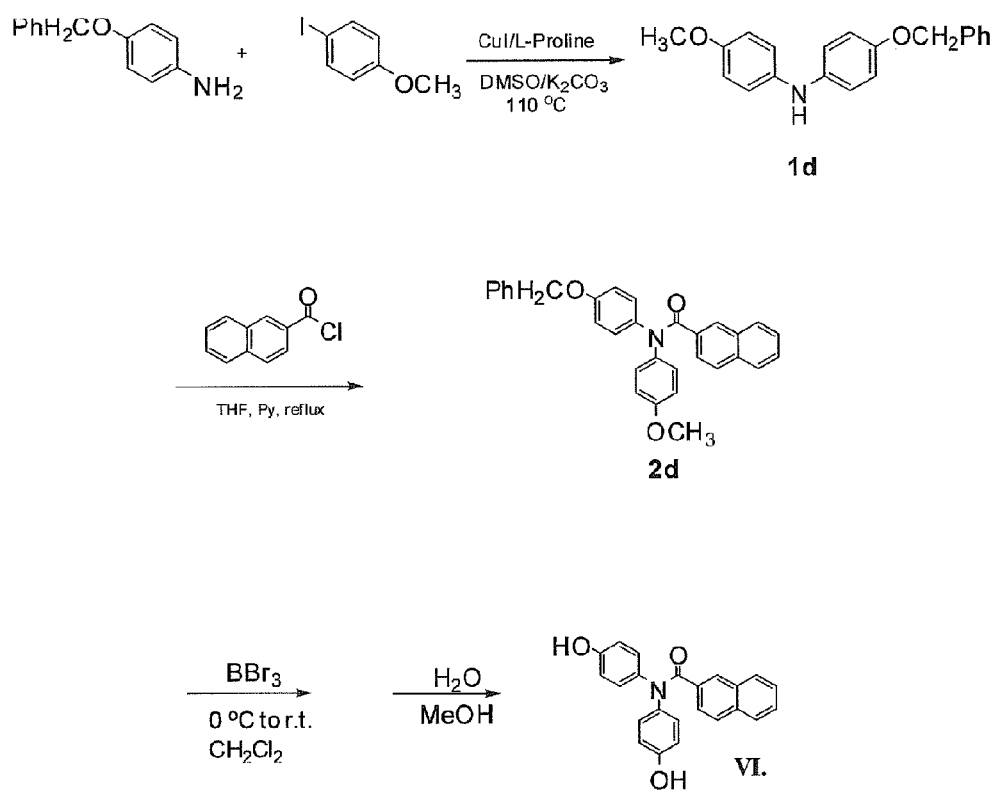
FIG. 7 Synthetic scheme for the preparation of Compound VI. (See Example 3.)

In a further example, Compound VI is prepared according to Example 3, and FIG. 7.

In another example, Compound VII is prepared according to Example 1, and FIG. 5.

In another example, Compound VIII is prepared according to Example 4, and FIG. 5.

Figure 8:
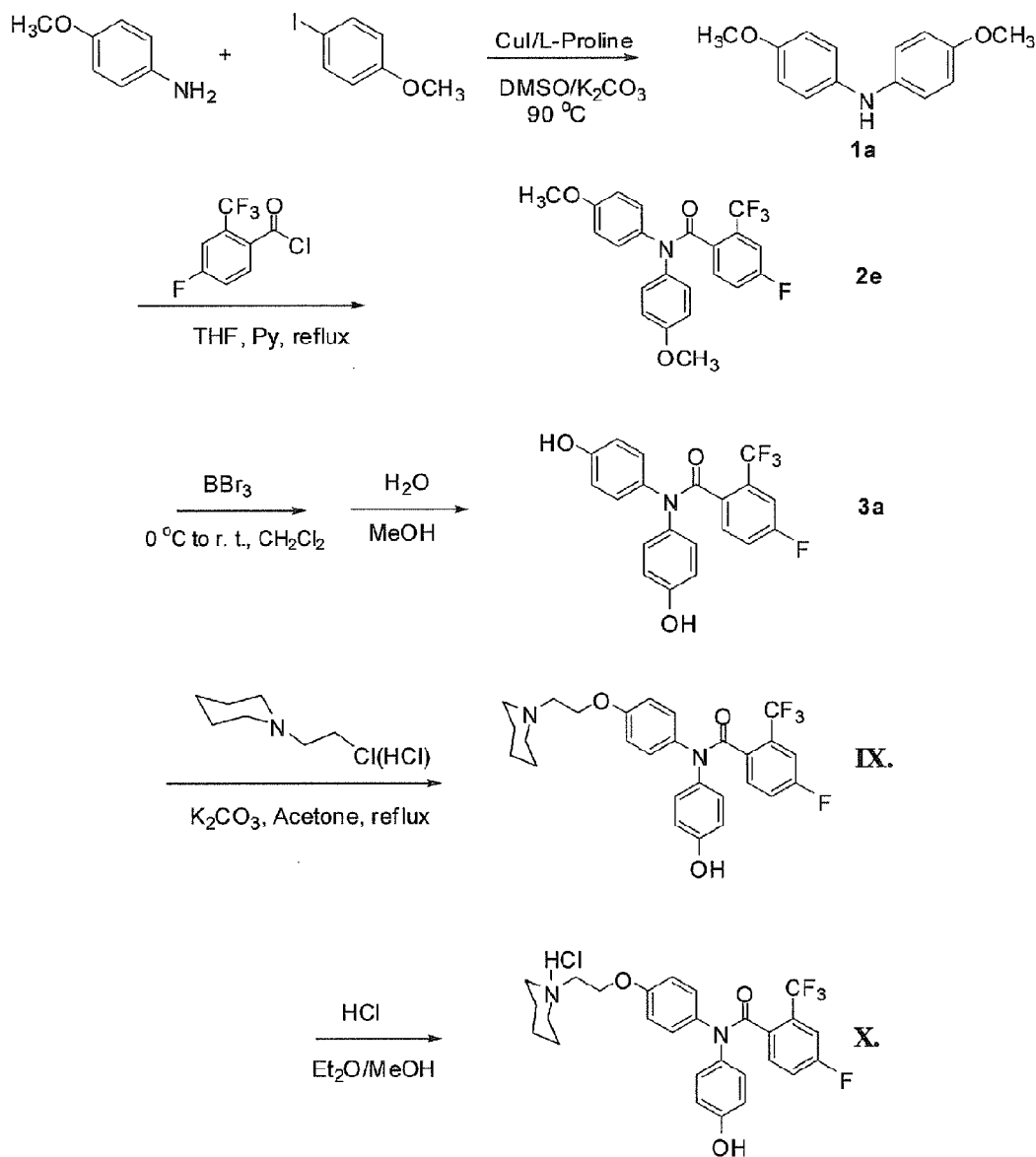
FIG. 8 Synthetic scheme for the preparation of Compounds IX and X. (See Example 5.)

In another example, Compound IX is prepared according to Example 5 and FIG. 8.

In another example, Compound X hydrochloride is prepared according to Example 5 and FIG. 8.

In another example, Compound XI is prepared according to Example 1, and FIG. 5.

In another example, Compound XII is prepared according to Example 1, and FIG. 5.

Suitable hydroxyl protecting groups include, for example, a methyl ether(methoxy), benzyl ether(benzyloxy)methoxymethyl (MOM) ether, benzoyloxymethyl (BOM) ether, benzyl, carbobenzoxy, methoxyethoxymethyl (MEM) ether, 2-(trimethylsilyl)ethoxymethyl (SEM) ether, methylthiomethyl (MTM) ether, phenylthiomethyl (PTM) ether, azidomethyl ether, cyanomethyl ether, 2,2-dichloro-1,1-difluoroethyl ether, 2-chloroethyl ether, 2-bromoethyl ether, tetrahydropyranyl (THP) ether, 1-ethoxyethyl (EE) ether, phenacyl ether, 4-bromophenacyl ether, cyclopropylmethyl ether, allyl ether, propargyl ether, isopropyl ether, cyclohexyl ether, t-butyl ether, benzyl ether, 2,6-dimethylbenzyl ether, 4-methoxybenzyl ether, o-nitrobenzyl ether, 2,6-dichlorobenzyl ether, 3,4-dichlorobenzyl ether, 4-(dimethylamino) carbonylbenzyl ether, 4-methylsulfinylbenzyl ether, 4-anthrylmethyl ether, 4-picolyl ether, heptafluoro-p-tolyl, tetrafluoro-4-pyridyl ether, trimethylsilyl (TMS) ether, t-butyldimethylsilyl (TBDMS) ether, t-butyldiphenylsilyl (TBDPS) ether, triisopropylsilyl (TIPS) ether, aryl formate, arylacetate, aryl levulinate, arylpivaloate, aryl benzoate, aryl 9-fluorencarboxylate, aryl methyl carbonate, 1-adamantyl carbonate, t-butyl carbonate, 4-methylsulfinylbenzyl carbonate, 2,4-dimethylpent-3-yl carbonate, aryl 2,2,2-trichloroethyl carbonate, aryl benzyl carbonate, aryl carbamate, dimethylphosphinyl ester (Dmp-OAr), dimethylphosphinothionyl ester (Mpt-OAr), diphenylphosphinothionyl ester (Dpt-OAr), aryl methanesulfonate, aryl toluenesulfonate or aryl 2-formylbenzenesulfonate.

The methods of this invention comprise the use of compounds IA, I-XII, wherein the process for the preparation of the compounds of this invention comprise reaction of a diphenyl amine with a benzoyl chloride in the presence of a base. Suitable bases include, for example, pyridine, triethylamine, $K_2CO_3$, $Cs_2CO_3$, $Na_2CO_3$, methylamine, imidazole, benzimidazole, histidine, tributylamine or any combination thereof. In one embodiment, the base is pyridine.

The methods of this invention comprise the use of compounds IA, I-XII, wherein the process for the preparation of the compounds of this invention comprises deprotection of a protected hydroxyl. In another embodiment, the deprotection conditions depend on the protecting group. In some embodiment, the deprotection step comprises hydrogenation in the presence of Pd/C. In another embodiment, the deprotection comprises reaction with $BBr_3$. In another embodiment, the deprotection step comprises reaction with an acid.

In further examples, Compounds IA, I-XII are prepared according to FIGS. 5-8 and Examples 1-5.

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the compound of this invention, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a male subject.

This invention provides, in other embodiments, pharmaceutical products of the compounds described herein. The term "pharmaceutical product" refers, in other embodiments, to a composition suitable for pharmaceutical use (pharmaceutical composition), for example, as described herein.

The compounds of the invention can be administered alone or as an active ingredient of a formulation. Thus, the present invention also includes pharmaceutical compositions of compounds of Formula I, containing, for example, one or more pharmaceutically acceptable carriers.

Numerous standard references are available that describe procedures for preparing various formulations suitable for administering the compounds according to the invention.

Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The mode of administration and dosage forms is closely related to the therapeutic amounts of the compounds or compositions which are desirable and efficacious for the given treatment application.

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterile administration, and other dosage forms for systemic delivery of active ingredients. Formulations suitable for oral administration are preferred.

To prepare such pharmaceutical dosage forms, the active ingredient may be mixed with a pharmaceutical carrier according to conventional pharmaceutical compounding techniques. The carrier may take a wide variety of forms depending on the form of preparation desired for administration.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Treatment methods of the present invention using formulations suitable for oral administration may be presented as discrete units such as capsules, cachets, tablets, or lozenges, each containing a predetermined amount of the active ingredient as, for example, a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration may comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from, for example, diluents, buffers, flavoring agents, binders, disintegrants, surface active agents, thickeners, lubricants, preservatives (including antioxidants), and the like.

The formulations of the present invention can have immediate release, sustained release, delayed-onset release or any other release profile known to one skilled in the art.

In one embodiment, this invention provides methods of a) lowering total serum testosterone levels; b) lowering free serum testosterone levels by reduction of luteinizing hormone (LH) or independent of reduction of LH hormone in a male subject having prostate cancer comprising administering an oral composition comprising a compound of formula IA, I-XII. In additional embodiments, the methods of this invention make use of an oral composition comprising a compound of formula II, formula III, formula IV, formula V, formula VI, formula VII, formula VIII, formula IX, formula X, formula XI or formula XII.

In one embodiment, this invention provides a method of treating prostate cancer by reducing LH levels or independent of reduction of LH levels in a male subject having prostate cancer comprising administering an oral composition comprising a compound of formula IA, I-XII. In additional embodiments, this invention provides methods of treating prostate cancer by reducing LH levels or independent of reduction of LH levels in a male subject having prostate cancer comprising administering an oral composition comprising a compound of formula II, formula III, formula IV, formula V, formula VI, formula VII, formula VIII, formula IX, formula X, formula XI or formula XII.

It is to be understood that this invention encompasses any embodiment of a compound as described herein, which in some embodiments is referred to as "a compound of this invention".

In one embodiment, the methods of this invention may comprise administration of a compound of this invention at various dosages. In one embodiment, a compound of this invention is administered at a dosage of 1-1500 mg per day. In additional embodiments, a compound of this invention is administered at a dose of 1-10 mg per day, 3-26 mg per day, 3-60 mg per day, 3-16 mg per day, 3-30 mg per day, 10-26 mg per day, 15-60 mg, 50-100 mg per day, 50-200 mg per day, 150-300 mg per day, 20-50 mg per day, 5-50 mg per day, 200-500 mg per day, 150-500 mg per day, 200-1000 mg per day, 300-1500 mg per day or 100-1000 mg per day.

In one embodiment, the methods of this invention may comprise administration of a compound of this invention at various dosages. In one embodiment, a compound of this invention is administered at a dosage of 3 mg. In additional embodiments, a compound of this invention is administered at a dosage of 10 mg, 30 mg, 50 mg, 100 mg, 200 mg, 300 mg, 450 mg, 500 mg, 600 mg, 900 mg, 1000 mg, or 1500 mg.

In one embodiment, the methods of this invention may comprise administration of a compound of this invention at various dosages. In one embodiment, a compound of this invention is administered at a dosage of 0.1 mg/kg/day. In additional embodiments, a compound of this invention is administered at a dosage between 0.2 to 30 mg/kg/day, or 0.2 mg/kg/day, 0.3 mg/kg/day, 1 mg/kg/day, 3 mg/kg/day, 5 mg/kg/day, 10 mg/kg/day, 20 mg/kg/day or 30 mg/kg/day.

In one embodiment of the methods of this invention are provided for use of a pharmaceutical composition comprising a compound of formula IA, I-XII. In additional embodiments, the methods of this invention are provided for use of a pharmaceutical composition comprising a compound of formula II, formula III, formula IV, formula V, formula VI, formula VII, formula VIII, formula IX, formula X, formula XI or formula XII.

In certain embodiment, the pharmaceutical composition is a solid dosage form. In another embodiment, the pharmaceutical composition is a tablet. In another embodiment, the pharmaceutical composition is a capsule. In another embodiment, the pharmaceutical composition is a solution. In another embodiment, the pharmaceutical composition is a transdermal patch.

In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

For administration to mammals, and particularly humans, it is expected that the physician will determine the actual dosage and duration of treatment, which will be most suitable for an individual and can vary with the age, weight, genetics and/or response of the particular individual.

In some embodiments, any of the compositions of this invention will comprise a compound of this invention, in any form or embodiment as described herein. In some embodiments, any of the compositions of this invention will consist of a compound of this invention, in any form or embodiment as described herein. In some embodiments, of the compositions of this invention will consist essentially of a compound of this invention, in any form or embodiment as described herein. In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

It is to be understood that any use of any of the compounds as herein described may be used in the treatment of any disease, disorder or condition as described herein, and represents an embodiment of this invention. In one embodiment, the compounds are a free base, free acid, non charged or non-complexed compound.

The following examples are presented in order to more fully illustrate the preferred embodiments of the invention. They should in no way, however, be construed as limiting the broad scope of the invention.

EXAMPLES

Example 1

General Synthesis Procedures for Compounds of Formulas II-XII and Synthetic Intermediates The organic solvents, surfactants and antioxidants, etc., they may be used in the compositions described herein are typically readily available from commercial sources. For example, PEG-300, polysorbate 80, Captex™ 200, Capmul™ MCM C8 may be purchased, for example, from Dow Chemical Company (Midland, Mich.), ICI Americas, Inc (Wilmington, Del.) or Abitec Corporation (Janesville, Wis.).

The estrogen receptor ligands described herein may be prepared in a number of ways well known to those skilled in the art. For example, the estrogen receptor ligands described herein may be prepared by the synthetic methods described in U.S. Patent Application Publication Nos. 2009/0062341, the disclosures of each of which are hereby incorporated by reference in their entireties.

General Synthesis of N,N-bis Aryl Benzamide Derivatives

General synthesis of diarylanilines (FIG. 5). A mixture of arylamine (1.5 equivalent), aryl iodide (1 equivalent), $K_2CO_3$ (2 equivalents), CuI (0.1 equivalent) and L-proline (0.2 equivalent) were mixed together and dissolved in anhydrous DMSO at room temperature. Then, the reaction mixture was stirred and heated to 90° C. for 28 hours. The mixture was cooled to room temperature and hydrolyzed with water. EtOAc was added to partition the solution. The EtOAc layer was separated, washed with brine, and dried over anhydrous $MgSO_4$. The solvent was removed under reduced pressure. The solid residue was purified by flash column chromatography (silica gel) using 5% EtOAc/hexanes as eluent to afford the corresponding diarylaniline.

Bis-(4-methoxyphenyl)amine (1a): pale-yellow solid, 73% yield. M.p. 98.6-99.0° C. $^1$H NMR ($CDCl_3$, 300 MHz) δ 6.93-6.81 (m,8H), 5.37 (s, br, 1H), 3.78 (s, 6H). MS m/z 228.4(M–H)$^+$ N-(4-Methoxyphenyl)-phenylamine (1b): pale-yellow solid, 70% yield. M.p. 106.3-106.5° C. $^1$H NMR ($CDCl_3$, 300 MHz) δ 7.24-7.18 (m, 3H), 7.08-7.06 (m, 2H), 6.92-6.84 (m, 4H), 5.61 (s, br, 1H), 3.79 (s, 3H). MS m/z 200.1(M+H)$^+$.

N-(4-Fluorophenyl)-N-4-methoxyphenylamine (1c): pale-yellow solid, 54% yield. M.p. 60.6-61.0° C. $^1$H NMR ($CDCl_3$, 300 MHz) δ 7.01-6.83 (m,8H), 3.78 (s, 3H). MS m/z 217(M)$^+$.

N-(4-Benzyloxyphenyl)-N-4-methoxyphenylamine (1d): pale-yellow solid, 54% yield. M.p. 108.0-108.4° C. $^1$H NMR ($CDCl_3$, 300 MHz) δ 7.34-7.08 (m, 5H), 6.90-6.81 (s, 3H), 3.78 (s, 3H). MS m/z 306(M+H)$^+$.

General Synthesis of Benzamides. A mixture of arylaniline (1 equivalent), benzoyl chlorides (1.3 equivalents), and pyridine (6 equivalents) was mixed together and dissolved in anhydrous THF at room temperature. The mixture was stirred and refluxed for 24 hours. The reaction solution was cooled to room temperature, and hydrolyzed by addition of 2N HCl solution. The solution was extracted with ethyl acetate. The organic layer was washed with a saturated aqueous $NaHCO_3$ solution to remove excess acid, dried over anhydrous $MgSO_4$, filtered and concentrated under reduced pressure. The residue was purified by flash column chromatography using EtOAc/hexanes (3/7 v/v) to afford the corresponding benzamide compounds.

3-Fluoro-N-(4-fluorophenyl)-4-methoxy-N-(4-methoxyphenyl)benzamide (2a): yellow solid, M.p. 54-56° C., $^1$H NMR ($CDCl_3$/TMS) δ 7.24-7.11 (m, 4H), 7.05-6.97 (m, 4H), 6.85-6.78 (m, 3H), 3.86 (s, 3H), 3.79 (s, 3H). MS (ESI) m/z 370.1 [M+H]$^+$ 4-Fluoro-N,N-bis(4-methoxyphenyl)-2-(trifluoromethyl)benzamide (2b): colorless oil, 84.2% yield. $^1$H NMR ($CDCl_3$, 300 MHz) δ 7.34-7.26 (m, 4H), 7.09-7.01 (m, 3H), 6.91 (d, 2H, J=8.7 Hz), 6.87 (d, 2H, J=8.7 Hz), 3.80 (s, 3H), 3.71 (s, 3H). MS m/z 442.1(M+Na)$^+$.

4-Methoxy-N-(4-methoxyphenyl)-N-(4-fluorophenyl)-benzamide (2c): white solid, 97% yield, M.p. 133.5.0-134.5°

C. $^1$H NMR (CDCl$_3$, 300 MHz) δ 8.11-6.66 (m, 15H), 3.74 (s, 3H), 3.73 (s, 3H). MS m/z 384 (M+H)$^+$.

N-(4-Methoxyphenyl)-N-(4-benzyloxyphenyl)-2-naphthylamide (2d): white solid, 58% yield. M.p. 174.9-175.5° C. $^1$H NMR (CDCl$_3$, 300 MHz) δ 8.04 (s, 1H), 7.77-7.74 (m, 2H), 7.64-7.61 (m, 1H), 7.51-7.43 (m, 4H), 7.40-7.31 (m, 4H), 7.13-7.10 m, 4H), 6.88-6.78 (m, 4H), 4.99 (s, 2H), 3.74 (s, 3H). MS m/z 460 (M+H)$^+$.

4-Fluoro-N,N-bis(4-methoxyphenyl)-2-(trifluoromethyl)benzamide (2e): colorless oil, 84.2% yield. $^1$H NMR (CDCl$_3$, 300 MHz) δ 7.34-7.26 (m, 4H), 7.09-7.01 (m, 3H), 6.91 (d, 2H, J=8.7 Hz), 6.87 (d, 2H, J=8.7 Hz), 3.80 (s, 3H), 3.71 (s, 3H). MS m/z 442.1(M+Na)$^+$.

General Procedure for Demethylation of Benzamide Derivatives Using BBr$_3$. A methoxybenzamide compound was dissolved in dry CH$_2$Cl$_2$. BBr$_3$ (1.0 M CH$_2$Cl$_2$ solution) was added dropwise at 0° C. The reaction solution was slowly warmed to room temperature and allowed to stir overnight at room temperature. The mixture was cooled to 0° C. in an ice bath and hydrolyzed by adding water. EtOAc was added to partition the solution. The organic layer was separated; the aqueous layer was extracted with EtOAc. The organic layer was washed with brine and dried over anhydrous MgSO$_4$. The solvent was removed under reduced pressure. The residue was purified by flash column chromatography using CH$_3$OH/CH$_2$Cl$_2$ (1/9 v/v) to afford the corresponding phenolic compounds.

4-Fluoro-N,N-bis(4-hydroxyphenyl)-2-(trifluoromethyl)benzamide (3a): white solid, 92.5% yield. $^1$H NMR (DMSO-d$_6$, 300 MHz) δ 9.55 (s, 1H), 9.53 (s, 1H), 7.69-7.58 (m, 2H), 7.46-7.39 (m, 1H), 7.18 (d, 2H, J=8.7 Hz), 6.93 (d, 4H, J=8.7 Hz), 7.03 (d, 2H, J=8.4 Hz), 6.78 (d, 2H, J=8.7 Hz), 6.57 (d, 2H, J=8.7 Hz). MS m/z 392.1(M+H)$^+$.

The following compounds where synthesized as described herein above and characterized and summarized in Table 1: N,N-bis(4-hydroxyphenyl)-4-propylbenzamide (II); 3-fluoro-N-(4-fluorophenyl)-4-hydroxy-N-(4-hydroxyphenyl)benzamide (IV); N,N-bis(4-hydroxyphenyl)-2,3-dimethylbenzamide (V); 3-fluoro-4-hydroxy-N,N-bis(4-hydroxyphenyl)-benzamide (VII); 3-fluoro-4-hydroxy-N-(4-hydroxyphenyl)-N-phenylbenzamide (XI); and 3-fluoro-N,N-bis(4-hydroxyphenyl)-2-methylbenzamide (XII).

General Procedures for Debenzylation of Benzyloxyphenyl-benzamides. Compound was dissolved in EtOH in a 250 mL hydrogenation bottle. Pd/C powder (5% mol) was added to the solution. The reaction vessel was mounted to a hydrogenation apparatus under 20 psi pressure hydrogen gas. The reaction was monitored by TLC until the disappearance of starting material. Then, the solvent was removed under reduced pressure. The residue was purified by flash column chromatography with hexanes/EtOAc=3/2 v/v to afford the desired product.

The following compounds where synthesized as described herein above and characterized and summarized in Table 1: N,N-bis(4-hydroxyphenyl)-2-naphthylamide (VI).

General Procedures for Reduction of Deprotected Benzamides. Benzamide compounds were dissolved in 20 mL anhydrous THF at room temperature. H$_3$B(SMe$_2$) was added via a syringe at room temperature under argon. The reaction solution was stirred and heated to reflux for 6 hours. Then, the reaction was quenched by adding 10 mL of MeOH at 0° C. The solvent was removed under reduced pressure. The residue was subjected to flash column chromatography (silicagel, CH$_2$Cl$_2$/MeOH=9/1 v/v) to afford the desired product.

The following compounds where synthesized as described herein above and characterized and summarized in Table 1: 4,4'-(2,3-dimethylbenzylazanediyl)diphenol (III); 4-((4-fluorophenyl)(4-hydroxybenzyl)amino)phenol (VIII).

General synthesis of O-(2-piperidin-1-ylethoxy)-benzamides and analogues. To a solution of hydroxyphenyl containing benzamide analogue (1 equivalent) in acetone, K$_2$CO$_3$ (3 equivalents) and N-chloroethyl-piperidine hydrochloride salt (1.2 equivalents) were added. The solution was heated to reflux for 6 hours. The solution was evaporated to dryness. The residue was hydrolyzed by adding water, and then extracted with ethyl acetate. The organic layers were separated and dried over anhydrous MgSO$_4$. The solvent was removed under reduced pressure. The residue was purified by flash chromatography with methylene chloride/methanol=9/1 v/v to give the desired compound. The hydrochloride salts were prepared by adding HCl in Et$_2$O to the methanol solution of the compounds followed by evaporation of solvents.

The following compounds where synthesized as described herein above and characterized and summarized in Table 1: 4-fluoro-N-(4-hydroxyphenyl)-N-(4-(2-(piperidin-1-yl)ethoxy)phenyl)-2-(trifluoromethyl)benzamide (IX); and 4-fluoro-N-(4-hydroxyphenyl)-N-(4-(2-(piperidin-1-yl)ethoxy)phenyl)-2-(trifluoromethyl)benzamide hydrochloride (X) which is the HCl salt of IX.

TABLE 1

Physical Characterization of Compounds of Formulas II-XII.

| Cmpd # | Structure | PHYSICAL CHARACTERIZATION |
|---|---|---|
| II. | (structure) | $^1$H NMR (DMSO-d$_6$, 300 MHz) δ 9.46 (s, 2H, 2 X OH), 7.27-7.26 (m, 2H, ArH), 7.06-7.04 (m, 2H, ArH), 6.99-6.97 (m, 4H, ArH), 6.66-6.65 (m, 4H, ArH), 2.50 (s, 2H, CH$_2$, overlapped with DMSO peak), 1.53-1.52 (m, 2H, CH$_2$), 0.82 (t, J = 7.33 Hz, 3H, CH$_3$). m/z 346.0 (M − H)$^-$ |

TABLE 1-continued

Physical Characterization of Compounds of Formulas II-XII.

| Cmpd # | Structure | PHYSICAL CHARACTERIZATION |
|---|---|---|
| III. | 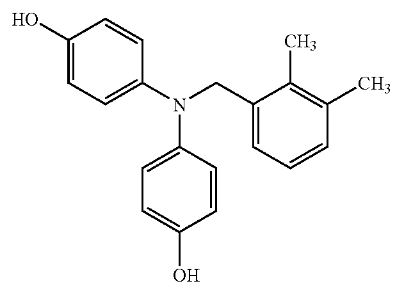 [SMILES: Cc1cccc(CN(c2ccc(O)cc2)c2ccc(O)cc2)c1C] | Tan foam, 41% yield. M.p. 147-150° C. $^1$H NMR (DMSO-$d_6$, 300 MHz) δ 8.92 (s, 2H), 7.07 (d, J = 7.33 Hz, 1H), 7.00-6.94 (m, 2H), 6.76-6.72 (m, 4H), 6.63-6.59 (m, 4H), 4.72 (s, 2H), 2.23 (s, 3H), 2.16 (s, 3H). m/z 320.2 (M + H)$^+$ |
| IV. | 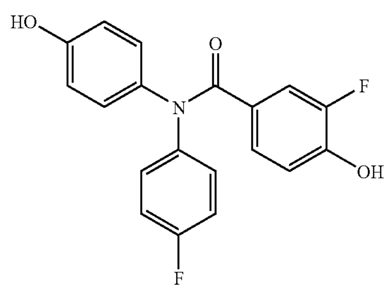 [SMILES: O=C(c1ccc(O)c(F)c1)N(c1ccc(O)cc1)c1ccc(F)cc1] | Tan solid, 92% yield. M.p. 110-112° C. $^1$H NMR (DMSO-$d_6$, 300 MHz) δ 10.14 (bs, 1H), 9.71 (bs, 1H), 7.26-7.11 (m, 5H), 7.05-6.99 (m, 3H), 6.78 (t, J = 8.61 Hz, 2H), 6.68 (d, J = 8.68 Hz, 2H). m/z 364.1 (M + Na)$^+$ |
| V. | 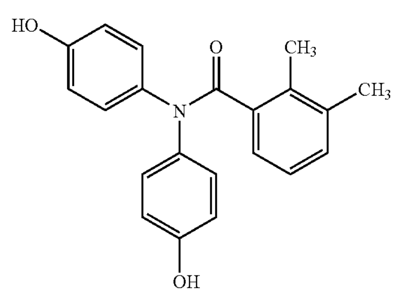 [SMILES: Cc1cccc(C(=O)N(c2ccc(O)cc2)c2ccc(O)cc2)c1C] | $^1$H NMR (DMSO-$d_6$, 300 MHz) δ 9.47 (bs, 2H, 2 X OH), 7.18 (d, J = 8.30 Hz, 2H, ArH), 7.06 (d, J = 7.08 Hz, 1H, ArH), 7.00-6.92 (m, 4H, ArH), 6.78 (d, J = 8.30 Hz, 2H, ArH), 6.51 (d, J = 8.06 Hz, 2H, ArH), 2.22 (s, 3H, CH$_3$), 2.15 (s, 3H, CH$_3$). m/z 334.3 (M + H)$^+$ |
| VI. | 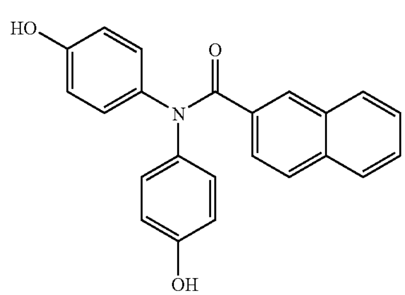 [SMILES: O=C(c1ccc2ccccc2c1)N(c1ccc(O)cc1)c1ccc(O)cc1] | white solid, 70% yield. M.p. 264.3-265.2° C. (decomposed). $^1$H NMR (DMSO-$d_6$, 500 MHz) δ 9.46 (s, 2H), 7.98 (s, 1H), 7.85-7.75 (m, 2H), 7.75-7.73 (m, 2H), 7.54-7.48 (m, 2H), 7.45-7.43 (m, 1H), 7.05 (s, 4H), 6.66 (s, 4H). m/z 356 (M + H)$^+$ |
| VII. | 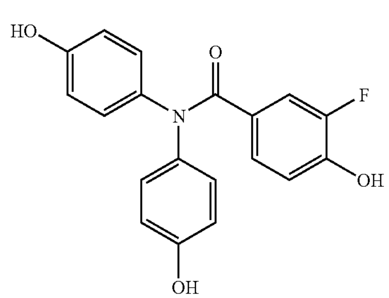 [SMILES: O=C(c1ccc(O)c(F)c1)N(c1ccc(O)cc1)c1ccc(O)cc1] | $^1$H NMR (DMSO-$d_6$, 300 MHz) δ 10.25 (bs, 1H, OH), 9.48 (bs, 2H, 2 X OH), 7.12-6.95 (m, 6H, ArH), 6.80-6.65 (m, 5H, ArH). m/z 338.0 (M − H)$^−$ |

TABLE 1-continued

Physical Characterization of Compounds of Formulas II-XII.

| Cmpd # | Structure | PHYSICAL CHARACTERIZATION |
|---|---|---|
| VIII. | 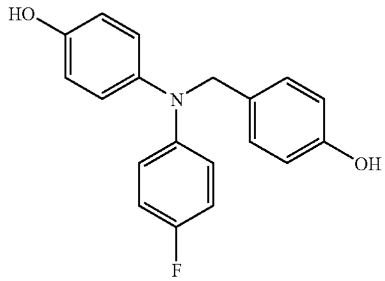 [SMILES: Oc1ccc(CN(c2ccc(O)cc2)c2ccc(F)cc2)cc1] | yellow oil, 92% yield. $^1$H NMR (DMSO-$d_6$, 500 MHz) δ 9.29 (s, 1H), 9.24 (s, 1H), 7.09 (d, 2H, J = 8.3 Hz), 6.98 (d, 2H, J = 9.0 Hz), 6.94-6.91 (m, 2H), 6.73 (d, 2H, J = 9.0 Hz), 6.68-6.64 (m, 4H), 4.70 (s, 2H). m/z 307.8 (M − H)$^−$ |
| IX. and X. (HCl salt of IX.) | 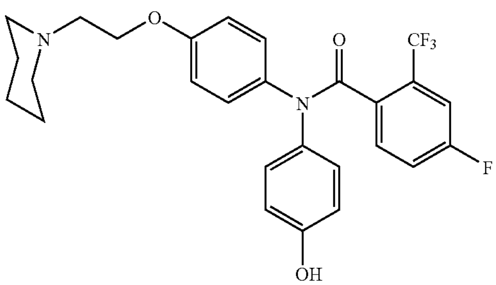 [SMILES: O=C(c1ccc(F)cc1C(F)(F)F)N(c1ccc(O)cc1)c1ccc(OCCN2CCCCC2)cc1] | white solid, 57.7% yield. $^1$H NMR (DMSO-$d_6$, 300 MHz) δ 9.57 (s, 1H), 7.71-7.68 (m, 2H), 7.47-7.44 (m, 1H), 7.28 (d, 1H, J = 9.0 Hz), 7.18 (d, 1H, J = 8.7 Hz), 7.13 (d, 1H, J = 8.7 Hz), 7.05 (d, 1H, J = 8.4 Hz), 6.97 (d, 1H, J = 9.0 Hz), 6.80-6.76 (m, 2H), 6.57 (d, 1H, J = 87. Hz), 4.06 (t, 1H, J = 6.0 Hz), 3.93 (t, 1H, J = 6.0 Hz), 2.66 (t, 1H, J = 5.7 Hz), 2.55 (t, 1H, J = 5.4 Hz), 2.44 (s, 2H), 2.36 (s, 2H), 1.49-1.37 (m, 6H). m/z 501.0 (M − H)$^−$ |
| XI. | 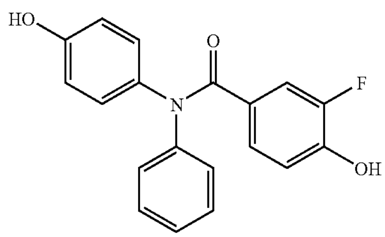 [SMILES: O=C(c1ccc(O)c(F)c1)N(c1ccccc1)c1ccc(O)cc1] | $^1$H NMR (DMSO-$d_6$, 300 MHz) δ 9.95 (bs, 1H, OH), 9.47 (bs, 2H, 2 X OH), 7.02-6.95 (m, 6H, ArH), 6.75-6.72 (m, 1H, ArH), 6.68-6.66 (m, 4H, ArH). m/z 324.0 (M + H)$^+$ |
| XII. | 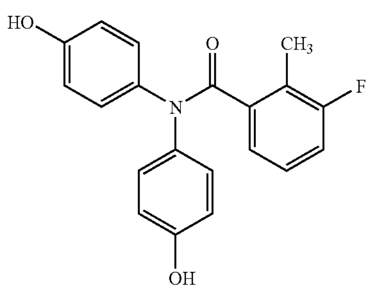 [SMILES: Cc1c(F)cccc1C(=O)N(c1ccc(O)cc1)c1ccc(O)cc1] | Pale-red solid. 72.0% yield. M.p. >240 °C. $^1$H NMR (DMSO-$d_6$, 300 MHz) δ 9.50 (bs, 2H), 7.19-6.79 (m, 7H), 6.61 (d, J = 8.93 Hz, 2H), 6.53 (d, J = 7.79 Hz, 2H), 2.23 (s, 3H). m/z 336.0 (M − H)$^−$. |

Example 2

Synthesis of the Compound of Formula IV (FIG. 6)

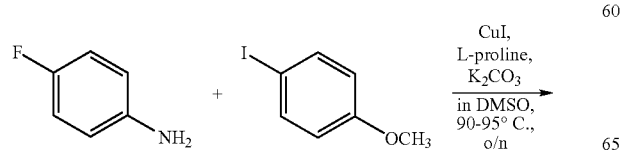

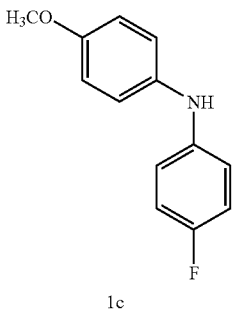

-continued

Step 1: Synthesis of 4-fluoro-N-(4-methoxyphenyl)aniline (1c)

A mixture of 4-fluoroaniline (78.63 g, 0.708 mol), 4-iodoanisole (138.00 g, 0.590 mol), anhydrous $K_2CO_3$ (122.23 g, 0.884 mol), CuI (11.23 g, 58.96 mmol) and L-proline (13.58 g, 0.118 mol) was mixed together in a dry 1 L three-necked round-bottomed flask fitted with a stirring bar, a reflux condenser and an argon inlet. Anhydrous DMSO (300 mL) was added at room temperature. The reaction mixture was stirred and heated to 90° C. for 20 hours under argon. Then, the mixture was cooled to room temperature and hydrolyzed with water (300 mL). EtOAc (200 mL) was added to partition the solution. The EtOAc layer was separated. The aqueous layer was extracted with 100 mL of EtOAc. The EtOAc layers were combined, washed with brine (2×100 mL) and dried over anhydrous $MgSO_4$ (50 g). The solvent was removed under reduced pressure. The brown oil residue was purified by flash column chromatography (silica gel, Hexanes/EtOAc=9/1 v/v) to afford 4-fluoro-N-(4-methoxyphenyl)aniline (1c) as a yellow solid product, 99.70 g, 77.8% yield. M.p. 46-48° C. MS (ESI) m/z 218.1 [M+H]$^+$, $^1$H NMR (DMSO-d$_6$, 300 MHz) δ 7.77 (bs, 1H), 7.03-6.98 (m, 4H), 6.93-6.82 (m, 4H), 3.70 (s, 3H).

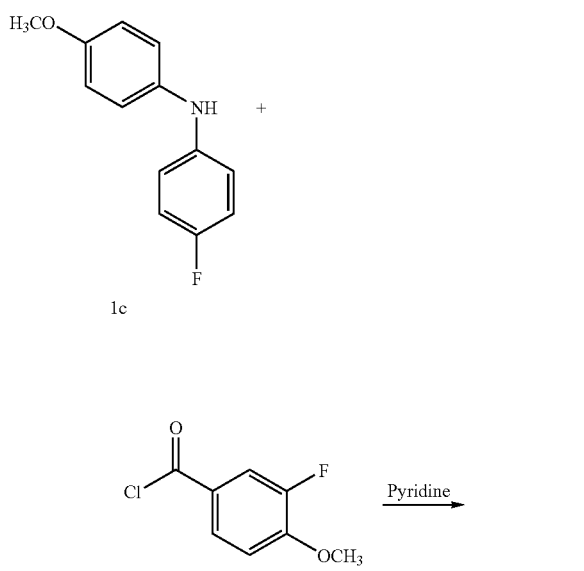

1c

Step 2: Synthesis of 3-fluoro-N-(4-fluorophenyl)-4-methoxy-N-(4-methoxyphenyl)benzamide (2a)

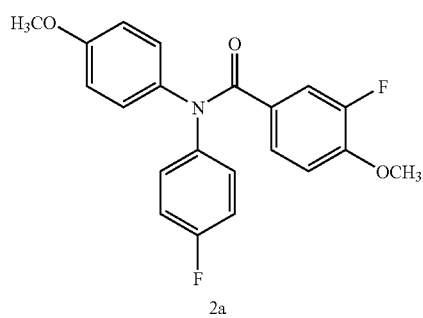

2a

4-Fluoro-N-(4-methoxyphenyl)aniline (1c) (90.78 g, 0.418 mol) and 3-fluoro-4-methoxybenzoyl chloride (94.55 g, 0.501 mol) were mixed together and dissolved in anhydrous THF (200 mL) in a dry 1 L three-necked round-bottomed flask fitted with a stifling bar, a reflux condenser and an argon inlet. Anhydrous pyridine (132.22 g, 1.672 mol) was added via a syringe at room temperature under argon. The reaction mixture was stirred and heated to reflux overnight. Then, the reaction mixture was cooled to room temperature and filtered to remove pyridine salt. The solution was concentrated to remove THF solvent. The residue oil was washed with 200 mL of 2N HCl solution and extracted with ethyl acetate (2×200 mL). The combined organic layer was washed with a saturated aqueous $Na_2CO_3$ solution (150 mL) to remove excess benzoyl chloride and acid, dried over $MgSO_4$ (50 g), filtered, and concentrated under reduced pressure to give an oil. The residue was purified by flash column chromatography using silica-gel with $CH_2Cl_2$/acetone (50/1 v/v) to afford the pure corresponding benzamide compound as a yellow solid. M.p. 54-56° C. MS (ESI) m/z 370.1 [M+H]$^+$, $^1$H NMR (CDCl$_3$/TMS) δ 7.24-7.11 (m, 4H), 7.05-6.97 (m, 4H), 6.85-6.78 (m, 3H), 3.86 (s, 3H), 3.79 (s, 3H).

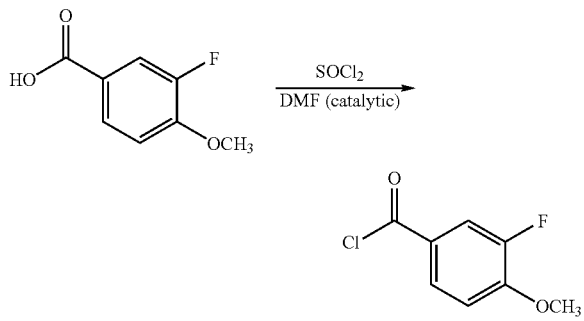

2a

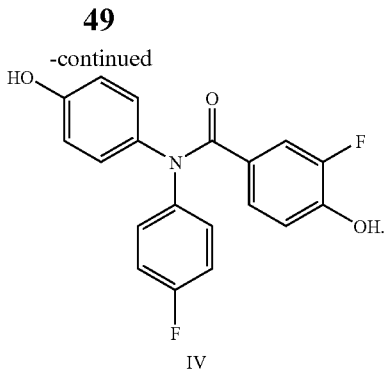

IV

Step 3: Synthesis of 3-fluoro-N-(4-fluorophenyl)-4-hydroxy-N-(4-hydroxyphenyl)benzamide (IV)

Compound 3-fluoro-N-(4-fluorophenyl)-4-methoxy-N-(4-methoxyphenyl)benzamide (2a) (138.0 g, 0.374 mol) was dissolved in dry $CH_2Cl_2$ (600 mL) at room temperature under an argon. $BBr_3$ (374.75 g, 1.496 mol) was added dropwise with stirring via a syringe at 0° C. in an ice-bath under an argon. The reaction solution was allowed to stir at room temperature overnight. Then, the solution was poured to 1 L of ice water with stifling. The slurry mixture was stirred at room temperature for 2 hours. The white precipitate was filtered, washed with water (2×100 mL) and dried under vacuum. The $CH_2Cl_2$ layer was separated, dried over anhydrous $MgSO_4$ (50 g), filtered and concentrated under reduced pressure to dryness. The white precipitate and residue from $CH_2Cl_2$ solution were combined and purified by flash column chromatography (silica gel, $CH_2Cl_2$/Acetone/MeOH=90/7/3 v/v/v) to give a light tan solid which was recrystallized from hot EtOAc/Hexanes solution twice to afford a white crystalline solid, 104.0 g, 81.6% yield. M.p. 110-112° C. MS (ESI) m/z 364.1 [M+Na]$^+$, $^1$H NMR (DMSO-d$_6$) δ 10.14 (bs, 1H), 9.71 (bs, 1H), 7.25-7.11 (m, 5H), 7.05-6.99 (m, 3H), 6.78 (t, J=8.6 Hz, 1H), 6.68 (d, J=8.7 Hz, 2H).

Example 3

Synthesis of the Compound of Formula VI (FIG. 7)

Synthesis of 4-(benzyloxy)-N-(4-methoxyphenyl)aniline (1d)

A mixture of 4-benzyloxyaniline (16.6 g, 83.31 mmol), 4-iodoanisole (15.0 g, 64.09 mmol), $K_2CO_3$ (17.72 g, 128.18 mmol), CuI (1.22 g, 6.41 mmol) and L-proline (1.48 g, 12.82 mmol) were mixed together and dissolved in anhydrous DMSO (120 mL) at room temperature. Then, the reaction mixture was stirred and heated to 90° C. for 48 hours. The mixture was cooled to room temperature and hydrolyzed with water. EtOAc was added to partition the solution. The EtOAc layer was separated washed with brine, dried over anhydrous $MgSO_4$. The solvent was removed under reduced pressure. The solid residue was purified by flash column chromatography (silica gel) using EtOAc/hexanes (1/9 v/v) to afford the corresponding diarylaniline as a yellow solid, 9.8 g, 50% yield. M.p. 108.0-108.4° C. $^1$H NMR (CDCl$_3$, 300 MHz) δ 7.34-7.25 (m, 5H), 6.90-6.81 (m, 8H), 5.02 (s, 2H), 3.78 (s, 3H). MS m/z 306 (M+H)$^+$.

Synthesis of N-(4-benzyloxyphenyl)-N-(4-methoxyphenyl)-2-naphthamide (2d)

One equivalent of 4-(benzyloxy)-N-(4-methoxyphenyl) aniline (0.80 g, 2.62 mmol) was mixed with 1.5 equivalents of 2-naphthoyl chloride (0.75 g, 3.93 mmol) and 4 equivalents of pyridine (0.83 g, 10.48 mmol) in a dry three-necked round-bottomed flask equipped with a magnetic stirring bar and a reflux condenser. The mixture was dissolved in anhydrous THF (30 mL) and heated to reflux for 20 hours. The reaction solution was cooled to room temperature and filtered. The solvent was removed under reduced pressure. The residue was purified by flash column chromatography using silica-gel with EtOAc/hexanes (3/7 v/v) to afford the pure corresponding naphthamide compound as a white solid, 0.70 g, 58% yield. M.p. 174.9-175.5° C. $^1$H NMR (CDCl$_3$, 300 MHz) δ 8.04 (s, 1H), 7.77-7.74 (m, 2H), 7.64-7.61 (m, 1H), 7.51-7.43 (m, 4H), 7.40-7.31 (m, 4H), 7.13-7.10 (m, 4H), 6.88-6.78 (m, 4H), 4.99 (s, 2H), 3.74 (s, 3H). MS m/z 460 (M+H)$^+$.

Synthesis of N,N-Bis(4-hydroxyphenyl)-2-naphthylamide (VI)

Compound N-(4-benzyloxyphenyl)-N-(4-methoxyphenyl)-2-naphthamide (2d) (0.50 g, 1.09 mmol) was dissolved in dry $CH_2Cl_2$ (30 mL) at room temperature. $BBr_3$ (3.26 mL of 1.0 M $CH_2Cl_2$ solution, 3.26 mmol) was added dropwise with stirring via a syringe at room temperature. The reaction solution was allowed to stir overnight at room temperature. The mixture was cooled to 0° C. in an ice bath and hydrolyzed by adding water. EtOAc was added to partition the solution. The organic layer was separated; the aqueous layer was extracted with EtOAc twice. The organic layers were combined, washed with brine and dried over anhydrous $MgSO_4$. The solvent was removed under vacuum. The residue was purified by flash column chromatography using silica-gel with $CH_3OH/CH_2Cl_2$ (1/9 v/v) to afford the pure desired phenolic compound as a white solid, 0.27 g, white solid, 70% yield. M.p. 264.3-265.2° C. (decomposed). $^1$H NMR (DMSO-d$_6$, 500 MHz) δ 9.46 (s, 2H), 7.98 (s, 1H), 7.85-7.75 (m, 2H), 7.75-7.73 (m, 2H), 7.54-7.48 (m, 2H), 7.45-7.43 (m, 1H), 7.05 (s, 4H), 6.66 (s, 4H). MS m/z 356 (M+H)$^+$.

Example 4

Synthesis of the Compound of Formula VIII

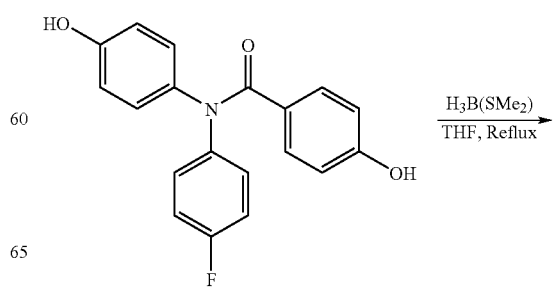

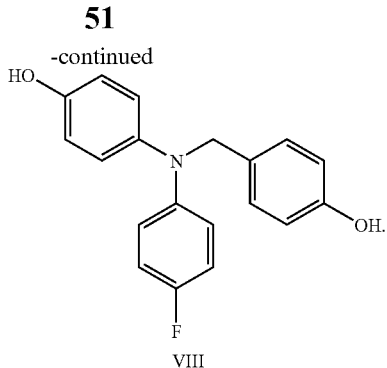

VIII

Synthesis of 4-((4-fluorophenyl)(4-hydroxybenzyl) amino)phenol (VIII.)

Compound N-(4-fluorophenyl)-4-hydroxy-N-(hydroxyphenyl)benzamide (0.30 g, 0.93 mmol) was dissolved in 20 mL anhydrous THF at room temperature. $H_3B(SMe_2)$ (1.86 mL of 2M THF solution, 3.71 mmol) was added via a syringe at room temperature under argon. The reaction solution was stirred and heated to reflux for 6 hours. Then, the reaction was quenched by adding 10 mL of MeOH at 0° C. The solvent was removed under reduced pressure. The residue was subjected to flash column chromatography (silica-gel, $CH_2Cl_2$/MeOH=9/1 v/v) to give a yellow oil, 0.26 g, 92% yield. $^1$H NMR (DMSO-$d_6$, 500 MHz) δ 9.29 (s, 1H), 9.24 (s, 1H), 7.09 (d, 2H, J=8.3 Hz), 6.98 (d, 2H, J=9.0 Hz), 6.94-6.91 (m, 2H), 6.73 (d, 2H, J=9.0 Hz), 6.68-6.64 (m, 4H), 4.70 (s, 2H). MS m/z 307.8 (M−H)$^−$.

Example 5

Synthesis of the Compound of Formulas IX and X (FIG. 8)

Synthesis of diarylanilines. A mixture of arylamine (1.5 equivalent), aryl iodide (1 equivalent), $K_2CO_3$ (2 equivalents), CuI (0.1 equivalent) and L-proline (0.2 equivalent) were mixed together and dissolved in anhydrous DMSO at room temperature. Then, the reaction mixture was stirred and heated to 90° C. for 28 hours. The mixture was cooled to room temperature and hydrolyzed with water. EtOAc was added to partition the solution. The EtOAc layer was separated, washed with brine, dried over anhydrous $MgSO_4$. The solvent was removed under reduced pressure. The solid residue was purified by flash column chromatography (silica gel) using EtOAc/hexanes (3/7 v/v) as solvent to afford the corresponding diarylaniline. Bis-(4-methoxyphenyl)amine (1a): pale-yellow solid, 73% yield. $^1$H NMR (CDCl$_3$, 300 MHz) δ 6.93-6.81 (m, 8H), 5.37 (s, br, 1H), 3.78 (s, 6H). MS m/z 228.4(M−H)$^+$.

Synthesis of 4-fluoro-N,N-bis(4-methoxyphenyl)-2-(trifluoromethyl)benzamide (2e)

1 equivalent of bis-(4-methoxyphenyl)amine (1a) (0.73 g, 3.18 mmol) was mixed with 1.2 equivalents of 4-fluoro-2-trifluoromethylbenzoyl chloride (0.87 g, 3.82 mmol) and 6 equivalents of pyridine (1.51 g, 19.08 mmol) in a dry three-necked round-bottomed flask equipped with a magnetic stirring bar and a reflux condenser. The mixture was dissolved in anhydrous THF (20 mL) and heated to 90° C. for 20 hours. The reaction solution was cooled to room temperature and filtered. The solvent was removed under reduced pressure. The residue was purified by flash column chromatography using silica-gel with EtOAc/hexanes (3/7 v/v) to afford the pure corresponding benzamide compound as a colorless oil, 1.12 g, 84.2% yield. $^1$H NMR (CDCl$_3$, 300 MHz) δ 7.34-7.26 (m, 4H), 7.09-7.01 (m, 3H), 6.91 (d, 2H, J=8.7 Hz), 6.87 (d, 2H, J=8.7 Hz), 3.80 (s, 3H), 3.71 (s, 3H). MS m/z 442.1 (M+Na)$^+$.

Synthesis of 4-fluoro-N,N-bis(4-hydroxyphenyl)-2-(trifluoromethyl)benzamide (3a)

Compound 4-fluoro-N,N-bis(4-methoxyphenyl)-2-(trifluoromethyl)benzamide (2e) (1.00 g, 2.38 mmol) was dissolved in dry $CH_2Cl_2$ (30 mL) at room temperature. BBr$_3$ (10 mL of 1.0 M $CH_2Cl_2$ solution, 10.0 mmol) was added dropwise with stirring via a syringe at room temperature. The reaction solution was allowed to stir overnight at room temperature. The mixture was cooled to 0° C. in an ice bath and hydrolyzed by adding water. EtOAc was added to partition the solution. The organic layer was separated; the aqueous layer was extracted with EtOAc twice. The organic layers were combined, washed with brine and dried over anhydrous $MgSO_4$. The solvent was removed under vacuum. The residue was purified by flash column chromatography using silica-gel with $CH_3OH/CH_2Cl_2$ (1/9 v/v) to afford the pure desired phenolic compound as a white solid, 0.86 g, 92.5% yield. $^1$H NMR (DMSO-$d_6$, 300 MHz) δ 9.55 (s, 1H), 9.53 (s, 1H), 7.69-7.58 (m, 2H), 7.46-7.39 (m, 1H), 7.18 (d, 2H, J=8.7 Hz), 6.93 (d, 4H, J=8.7 Hz), 7.03 (d, 2H, J=8.4 Hz), 6.78 (d, 2H, J=8.7 Hz), 6.57 (d, 2H, J=8.7 Hz). MS m/z 392.1(M+H)$^+$.

Synthesis of 4-fluoro-N-(4-hydroxyphenyl)-N-[4-(2-piperidin-1-yl)-ethoxy)phenyl]-2-(trifluoromethyl) benzamide. (IX)

To a solution of 4-fluoro-N,N-bis(4-hydroxyphenyl)-2-(trifluoromethyl)benzamide (3a) (0.61 g, 1.56 mmol) in acetone, $K_2CO_3$ (1.29 g, 9.36 mmol) and N-chloroethyl-piperidine hydrochloride salt (0.34 g, 1.87 mmol) were added. The solution was heated to reflux for 20 hours. The solution was evaporated to dryness. The residue was purified by flash chromatography (silica-gel; methylene chloride/methanol=9/1 v/v) to give the desired compound as a white solid, 0.45 g, 57.7% yield. $^1$H NMR (DMSO-$d_6$, 300 MHz) δ 9.57 (s, 1H), 7.71-7.68 (m, 2H), 7.47-7.44 (m, 1H), 7.28 (d, 1H, J=9.0 Hz), 7.18 (d, 1H, J=8.7 Hz), 7.13 (d, 1H, J=8.7 Hz), 7.05 (d, 1H, J=8.4 Hz), 6.97 (d, 1H, J=9.0 Hz), 6.80-6.76 (m, 2H), 6.57 (d, 1H, J=87. Hz), 4.06 (t, 1H, J=6.0 Hz), 3.93 (t, 1H, J=6.0 Hz), 2.66 (t, 1H, J=5.7 Hz), 2.55 (t, 1H, J=5.4 Hz), 2.44 (s, 2H), 2.36(s, 2H), 1.49-1.37 (m, 6H). MS m/z 501.0 (M−H)$^−$.

The hydrochloride salt (X) was prepared by adding HCl in Et$_2$O to the methanol solution of the compounds followed by evaporation of solvents.

Example 6

Estrogen Receptor Binding Affinities, Agonist and Antagonist Activity

The ER binding affinity of the compounds was determined using an in vitro competitive radioligand binding assay with [2,4,6,7-$^3$H(N)]-Estradiol ([$^3$H]E2), a natural high affinity ER ligand, and bacterially expressed GST fusion ER-α or ER-β ligand binding domain (LBD) protein.

Method

Recombinant ER-α or ER-β was combined with [$^3$H]E$_2$ to determine the equilibrium dissociation constant (K$_d$) of [$^3$H]E$_2$. Protein was incubated with increasing concentrations of [$^3$H]E$_2$ with and without a high concentration of unlabeled E$_2$ at 4° C. for 18 h in order to determine total and non-specific binding. Non-specific binding was subtracted and the K$_d$ of E$_2$ (ERα: 0.71 nM; ERβ: 1.13 nM) was determined using non-linear regression. In addition, the concentration of [$^3$H]E$_2$ required to saturate ER-α and ER-β LBD was determined to be 4-6 nM.

Increasing concentrations of the compounds (range: $10^{-11}$ to $10^{-6}$ M) were incubated with [$^3$H]E$_2$ (5.7 nM) and ER LBD using the conditions described above. Following incubation, plates were harvested with GF/B filters on the Unifilter-96 Harvester (PerkinElmer) and washed three times with ice-cold buffer B (50 mM Tris, pH 7.2). The filter plates were dried at room temperature, then 35 µl Microscint-O cocktail was added to each well and the filter plates were sealed with TopSeal-A. Radioactivity was counted in a TopCount® NXT Microplate Scintillation Counter using the settings for $^3$H in Microscint cocktail (PerkinElmer).

The specific binding of [$^3$H]E$_2$ at each concentration of the compounds was determined by subtracting the nonspecific binding of [$^3$H] E$_2$ (determined by incubating with $10^{-6}$ M unlabeled E$_2$) and expressing it as a percentage of the specific binding in the absence of test compound. The concentration of the compounds that reduced the specific binding of [$^3$H]E$_2$ by 50% (IC$_{50}$) was determined. The equilibrium binding constant (K$_i$) of the compounds was then calculated by: K$_i$=K$_d$× IC$_{50}$/(K$_d$+L), where K$_d$ is the equilibrium dissociation constant of [$^3$H]E$_2$ (ER-α=0.71 nM; ER-β=1.13 nM), and L is the concentration of [$^3$H]E$_2$ (ER-α: 5.7 nM; ER-β: 5.7 nM).

Results

Binding assays revealed that ligands bound ER-α and ER-β at various concentrations ranging from 3.75 nM to greater than 1000 nM and selectivity ranges from the compound being isoform selective to being non-isoform selective. Results from representative compounds are listed in Table 2.

TABLE 2

Binding results for selected compounds.

| COMPOUNDS | ER-α K$_i$ (nM) | ER-β K$_i$ (nM) |
|---|---|---|
| 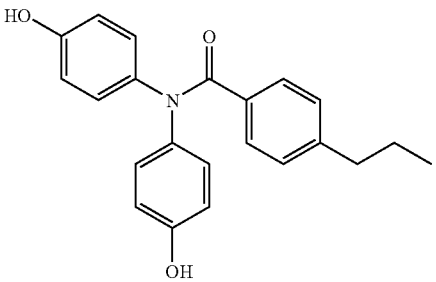<br>II | 3.75 | 81.6 |
| 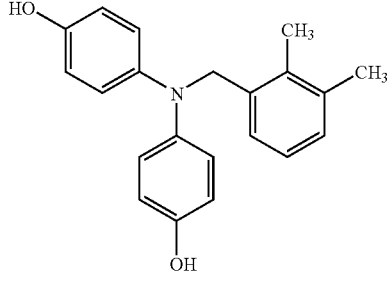<br>III | 3.81 | 6.44 |
| 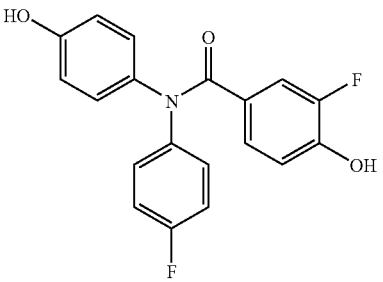<br>IV | 21.7 | 15.2 |

TABLE 2-continued
Binding results for selected compounds.
| COMPOUNDS | ER-α $K_i$ (nM) | ER-β $K_i$ (nM) |
|---|---|---|
| 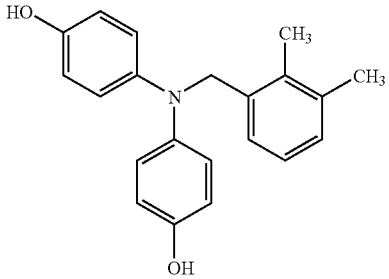<br>V | 7.13 | 35.9 |
| 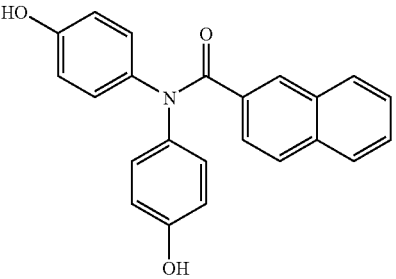<br>VI | 9 | 72 |
| 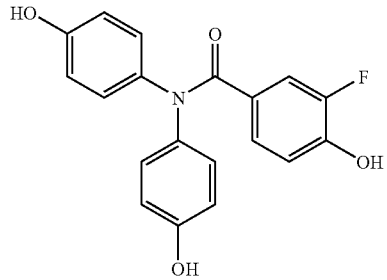<br>VII | 6.06 | 76.92 |
| 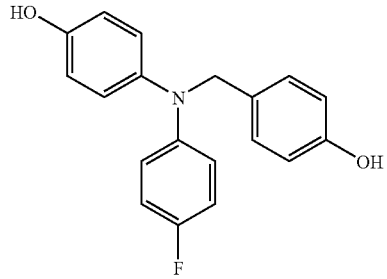<br>VIII | 13 | 19 |

TABLE 2-continued

Binding results for selected compounds.

| COMPOUNDS | ER-α $K_i$ (nM) | ER-β $K_i$ (nM) |
|---|---|---|
| 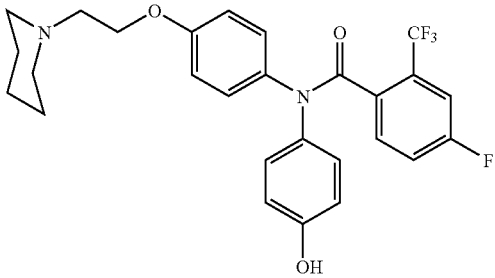<br>IX (or X) | 14.79 | 646.32 |
| 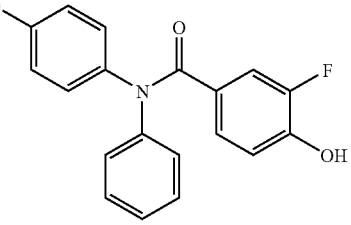<br>XI | 15 | 57 |
| 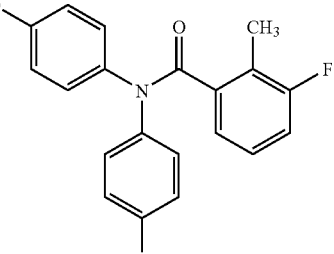<br>XII | 15.12 | 25.02 |

Compound IV binds to ERα and ERβ. The ER binding affinity of Compound IV was determined using an in vitro competitive radioligand binding assay with [2,4,6,7-$^3$H(N)]-Estradiol ([$^3$H]E$_2$), a natural high affinity ER ligand, and bacterially expressed GST fusion ERα or ERβ ligand binding domain (LBD) protein. In this assay, the ERα and ERβ binding affinities ($K_i$ values) of Compound IV were 21.7±1.7 nM (n=3) and 15.2±4.1 nM (n=3), respectively. Upon binding to ER, Compound IV initiates a complex series of molecular events that lead to the expression or repression of target genes involved with pharmacologic response in a tissue-selective manner. In transient transfection assays, Compound IV is an ERα and ERβ agonist, with greater demonstrated potency to stimulate ERα-mediated transcriptional activation as compared to that of ERβ. Whereas estradiol activates ERα and ERβ with a 5.1-fold greater selectivity for ERα, Compound IV shows a 49.0-fold selectivity for ERα. Thus, Compound IV has a relative 9.7-fold selectivity in relative transactivation potency (normalized to estradiol values) for ERα over ERβ. Additionally, no antagonist effects were observed in estradiol (1 nM)-stimulated transcriptional activation by Compound IV at concentrations up to 10 µM. Although many steroidal ligands cross-react with other nuclear hormone receptors, the actions of Compound IV are specific for ERα and ERβ. Compound IV was screened for cross-reactivity against rat isoforms of glucocorticoid receptor (GR), mineralocorticoids receptor (MR), progesterone receptor (PR), androgen receptor (AR) and human isoforms of farnesoid X receptor (FXR), liver X receptor (LXR), peroxisome proliferator-activated receptors (PPAR-α and PPAR-γ), and retinoid X receptor (RXR-α) in both agonist and antagonist modes in transcriptional activation assays. Compound IV did not display any agonist or antagonist activity in any of these assays, supporting the conclusion that Compound IV does not functionally cross-react with these nuclear hormone receptor superfamily members.

Example 7

Transactivation of Selected Compounds

Transactivation assays in agonist and antagonist modes were performed to identify whether the compound is an agonist, antagonist or a partial.

Method

Rat estrogen receptors (ER-α and ER-β) were cloned from rat ovarian cDNA into a pCR3.1 plasmid vector backbone. Sequencing was performed to determine the absence of any mutations. HEK-293 cells were plated at 100,000 cells per well of a 24 well plate in Dulbecco's Minimal Essential Media (DMEM) +5% charcoal-stripped fetal bovine serum (csFBS). The cells were transfected using Lipofectamine (Invitrogen, Carlsbad, Calif.) with 0.25 μg ERE-LUC, 0.02 μg CMV-LUC (renilla luciferase) and 12.5 ng of rat ER-α or 25 ng rat ER-β. The cells were treated 24 hrs after transfection with various concentrations of compounds or a combination of compounds and estradiol to determine the antagonistic activity. Luciferase assays were performed 48 hrs after transfection.

Results

Screening of compounds of this invention in the transactivation system revealed that the compounds belonged to all the three classes i.e. agonists, antagonists and partial agonist. An example of an agonist and an antagonist is given in Table-3. Transactivation results matched extremely well with the binding results for isoform selectivity.

Table 3 provides the $EC_{50}$ and $IC_{50}$ transactivation values for some selected compounds of this invention.

Example 8

Testosterone Suppression in Cynomolgus Monkeys

Two-year old gonadally-intact male Cynomolgus monkeys (n=2) were housed during the study in compliance with USDA Guidelines with free access to primate diet and water (except fasted prior to oral dose administration). Animals were given a once-daily oral gavage dose of 30 mg/kg of compound of formula IV in a microemulsion vehicle of Tween 80/deionized water for 7 consecutive days. Serum samples were withdrawn by venipuncture prior to the oral dose administration on days 1 (baseline), 3, 4, 5, 6, and 7. Testosterone and total androgens were quantified using an enzyme immunoassay (EIA) method combined with or without an HPLC method respectively. After 6-days of treatment with compound of formula IV, time-dependent decreases were apparent for testosterone and total androgens (testosterone/dihydrotestosterone). Compound of formula IV suppressed the levels of testosterone by 58% and 64% in animal #1 and animal #3, respectively, relative to baseline values (see solid lines in FIG. 1; Table 4). Similarly, total androgen levels were suppressed by 56% in both animals #1 and #3 (see dashed lines in FIG. 1; Table 4) compared to baseline values.

TABLE 3

Transactivation (both agonist and antagonist) of selective compounds of this invention.

| COMPOUND | ER-α $EC_{50}$ (nM) | ER-β $EC_{50}$ (nM) | ER-α $IC_{50}$ (nM) | ER-β $IC_{50}$ (nM) |
|---|---|---|---|---|
| 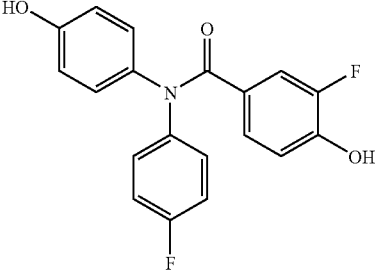 IV | 0.65 | 40.4 | >1000 | >1000 |
| 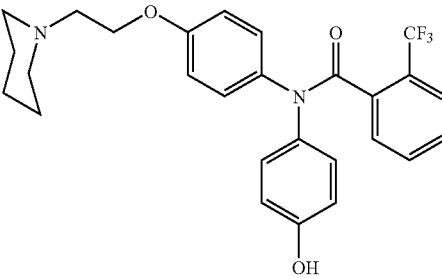 IX (or X) | >1000 | >1000.000 | 2.207 | 145 |

Consistent with estrogen feedback of the pituitary-testicular axis in males, these results demonstrate a robust pharmacologic response for the suppression of serum hormones (testosterone and total androgens) in intact non human primates (Cynomolgus monkeys) after repeated oral doses (30 mg/kg) of compound of formula IV.

TABLE 4

Testosterone and total androgen levels in serum of intact male monkeys with daily 30 mg/kg oral administration compound of formula IV (first dose on Day 0).

| Day | Testosterone Serum level (pg/mL) | | Total Androgens Serum level (pg/mL) | |
|---|---|---|---|---|
| | Animal 1 | Animal 3 | Animal 1 | Animal 3 |
| 0 (baseline) | 1120 | 617 | 1868 | 1643 |
| 2 | 937 | 479 | 1178 | 847 |
| 3 | 784 | 437 | 1078 | 786 |
| 4 | 552 | 415 | 988 | 924 |
| 5 | 403 | 276 | 966 | 664 |
| 6 | 474 | 221 | 819 | 726 |

| Day | Percent reduction from baseline | | Percent reduction from baseline | |
|---|---|---|---|---|
| | Animal 1 | Animal 3 | Animal 1 | Animal 3 |
| 0 (baseline) | 100 | 100 | 100 | 100 |
| 2 | 16 | 22 | 37 | 48 |
| 3 | 30 | 29 | 42 | 52 |
| 4 | 51 | 33 | 47 | 44 |
| 5 | 64 | 55 | 48 | 60 |
| 6 | 58 | 64 | 56 | 56 |

Example 9

Suppression of LH and Testosterone Hormone Levels in Rats

An in vivo dose-response study was conducted to evaluate the effect of Compound IV on LH suppression in intact and orchiectomized (ORX) male rats. In intact and ORX animals, Compound IV at doses ≥10 mg/kg per day significantly suppressed LH levels when compared to respective controls. (The same pattern of suppression was observed in FSH levels.) LH suppression resulted in robustly decreased testosterone levels to below the limit of quantitation (BLOQ) which is 0.08 ng/mL and decreased weights of prostate, seminal vesicles, and levator ani weights muscle since these are highly androgen-dependent organs. In intact animals, dose-dependent decreases in the weights of these target organs were noted with the seminal vesicles and levator ani muscle weights to the level of castrated controls. Although prostate weights were significantly reduced in intact animals, these values did not reach the level of castrated controls. Results are summarized in Table 6 hereinbelow.

Materials and Methods:

Male Sprague-Dawley rats weighing approximately 200 g were maintained on a 12-h light/dark cycle with food (2016 Teklad Global 16% Protein Rodent Diet, Harlan, Madison, Wis.) and water available ad libitum. The animal protocol was reviewed and approved by the Institutional Animal Care and Use Committee of the University of Tennessee.

The test article for this study was weighed and dissolved in 10% DMSO (Fisher) diluted with PEG 300 (Acros Organics, NJ) to prepare the appropriate dose formulations. For this study, sixty (60) male Sprague-Dawley rats were randomized by body weight, and assigned to one of the twelve treatment groups (n=5 animals/group). Treatment groups are listed in Table 5. The animals were housed in groups of 2 to 3 animals per cage. Control groups (intact and orchidectomized (ORX)) were administered vehicle daily. Compound IV was administered via subcutaneous injection (200 μL) at doses of 0.3, 1, 3, 10, and 30 mg/kg/day to both intact and ORX groups.

After a 14-day dosing regimen, the animals were sacrificed under anesthesia (ketamine/xylazine, 87:13 mg/kg) and body weights were recorded. In addition, ventral prostate, seminal vesicles, and levator ani muscle were removed, cleaned of extraneous tissue, and individually weighed. Organ weight were normalized to body weight and expressed as a percentage of intact control. Blood was collected from the abdominal aorta under isoflurane anesthesia and allowed to clot. Serum was separated by centrifugation and stored at −80° C. prior to determination of serum hormone levels. Serum luteinizing hormone (LH) and follicle stimulating hormone (FSH) concentrations were determined by the Rat Pituitary Luminex Assay (Millipore, Billerica, Mass.) according to manufacturer's directions. The lower limit of quantitation for this assay was 3.2 pg/mL for LH and 32 pg/mL for FSH. Testosterone was measured by a Testosterone EIA (Alpco Diagnostics, Salem, N.H.) with a LLOQ of 0.08 ng/mL. Serum hormone values below the lower limit of quantitation (BLOQ) were omitted from analysis of group means. Therefore, the reported value for LH and T in the groups with samples BLOQ is higher than the actual value. This method of analysis provided the most conservative estimate of LH and T suppression. Fisher's Least Significant Difference test was used to compare individual dose groups to the intact and ORX vehicle control groups. Significance was defined a priori as a P-value<0.05.

TABLE 5

Treatment groups.

| Group | Gonadal Status | Dose (mg/kg/day) | Test Article |
|---|---|---|---|
| 1 | Intact | — | Vehicle |
| 2 | ORX | — | Vehicle |
| 3 | Intact | 0.3 | Compound IV |
| 4 | Intact | 1 | Compound IV |
| 5 | Intact | 3 | Compound IV |
| 6 | Intact | 10 | Compound IV |
| 7 | Intact | 30 | Compound IV |
| 8 | ORX | 0.3 | Compound IV |
| 9 | ORX | 1 | Compound IV |
| 10 | ORX | 3 | Compound IV |
| 11 | ORX | 10 | Compound IV |
| 12 | ORX | 30 | Compound IV |

Luteinizing Hormone Levels in Intact and ORX Rats (Table 6)

Figure 10A:
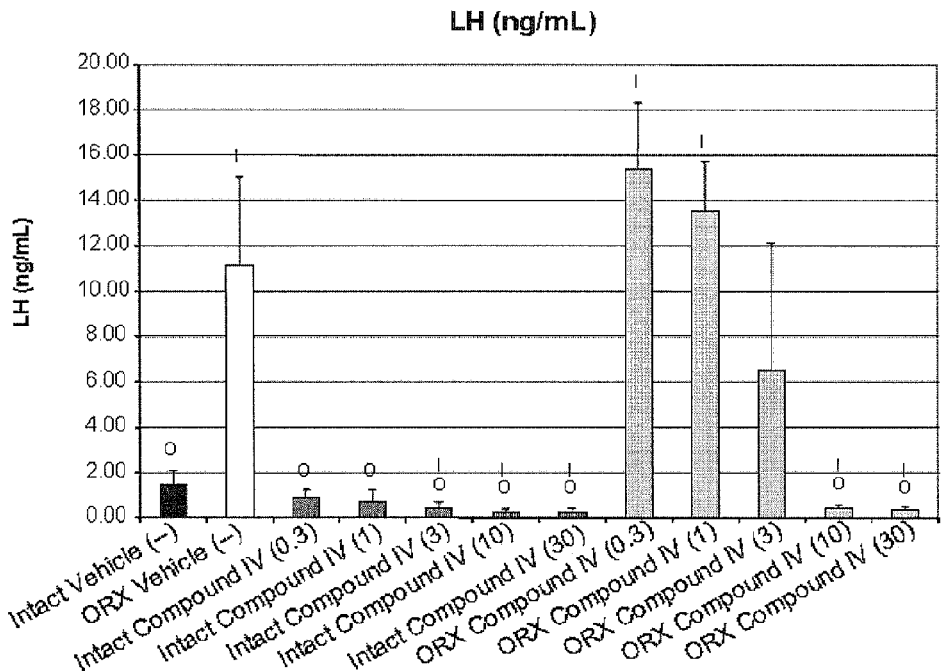
FIG. 10 depicts LH levels (FIG. 10A), FSH levels (FIG. 10B), testosterone levels (FIG. 10C), prostate weight levels (FIG. 10D), seminal vesicle weight levels (FIG. 10E) and levator ani weight (FIG. 10F) of treated intact and orchidectomized (ORX) rats with 0.3 mg/kg, 1 mg/kg, 3 mg/kg, 10 mg/kg and 30 mg/kg dosages of Compound IV. $^I$denotes P<0.05 vs. intact vehicle controls. $^O$denotes P<0.05 vs. ORX vehicle controls BLOQ values are represented graphically at the limit of quantitation 0.08 ng/mL. (See Example 9.)

LH levels (mean±SD) in intact and ORX vehicle control groups were 1.46±0.64 and 11.1±3.9 ng/mL, respectively. Compound IV dose-dependently reduced LH levels in intact animals, reaching statistically significant reductions with daily doses ≥3 mg/kg. LH levels in intact Compound IV treated animals were 0.863±0.384, 0.704±0.530, 0.395±0.302, 0.226±0.165, and 0.236±0.176 ng/mL, following doses of 0.3, 1, 3, 10, and 30 mg/kg/day, respectively. LH levels in ORX males were also significantly decreased by Compound IV treatment. In ORX animals the LH levels were 15.4±2.9, 13.5±2.2, 6.5±5.6, 0.425±0.135, and 0.368±0.119 ng/mL, following doses of 0.3, 1, 3, 10, and 30 mg/kg/d, respectively. The results are presented graphically in FIG. 10A.

Follicle Stimulating Hormone Levels in Intact and ORX Rats (Table 6)

Figure 10B:
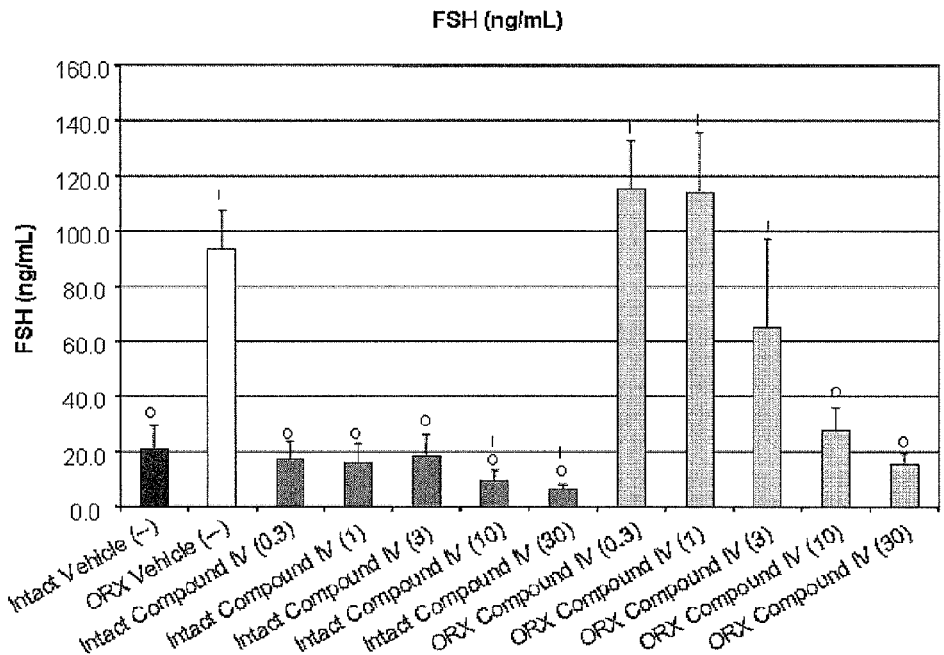

Serum FSH levels in intact and ORX vehicle control groups were 20.9±8.5 and 93.5±13.8 ng/mL, respectively. In intact animals, Compound IV dose-dependently reduced FSH levels with significant reductions observed at doses ≥10 mg/kg/day. FSH levels in intact Compound IV treated animals were 17.3±6.4, 15.7±7.3, 18.4±7.7, 9.2±4.0, and 6.3±1.8 ng/mL, following doses of 0.3, 1, 3, 10, and 30 mg/kg/day, respectively. In ORX animals the LH levels were 115±17, 114±22, 65.2±31.9, 27.6±8.2, and 15.1±4.1 ng/mL, following doses of 0.3, 1, 3, 10, and 30 mg/kg/day, respectively. The results are presented graphically in FIG. 10B.

Testosterone Levels in Intact and ORX Rats

Figure 2:
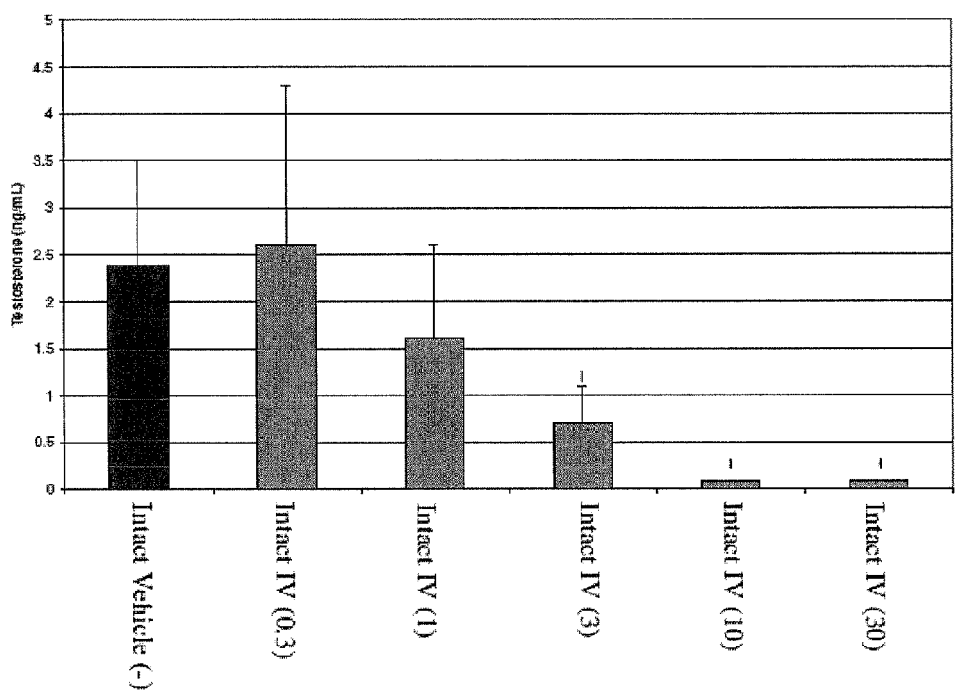
FIG. 2 depicts testosterone levels in intact rats treated with Compound IV (0.3, 1, 10, 30 mg/kg). $^I$denotes P<0.05 vs. intact vehicle controls. BLOQ values are represented graphically at the limit of quantitation 0.08 ng/mL. (See Example 9.)
Figure 10C:
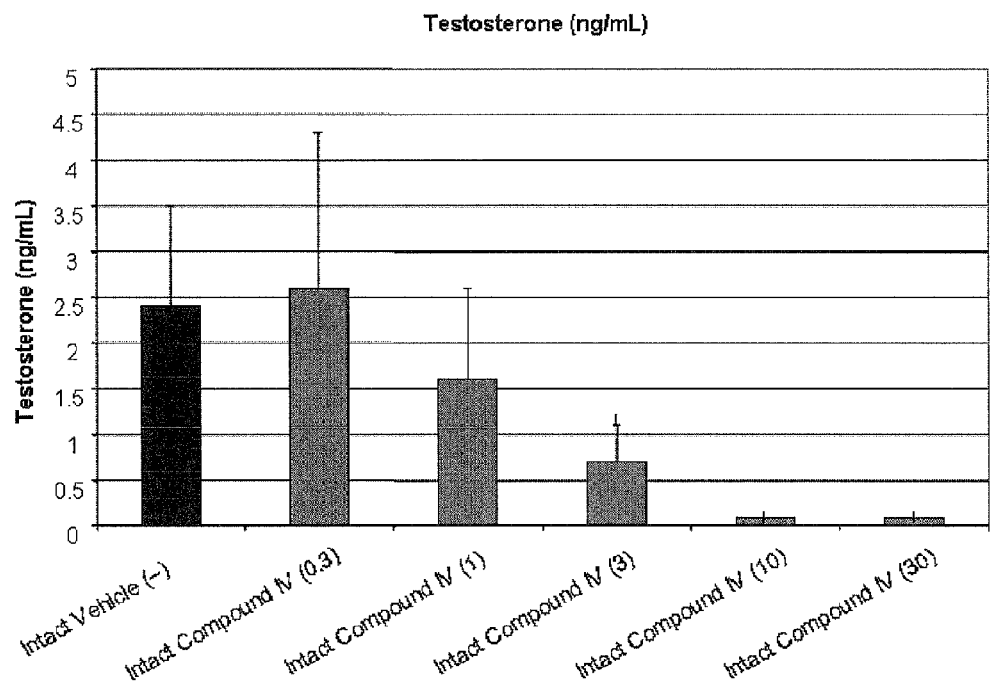

Serum testosterone levels in intact vehicle control groups were 2.4±1.1 ng/mL. The lower limit of quantitation for T was 0.08 ng/mL. Values less than 0.08 ng/mL are designated as Below the Limit Of Quantitation (BLOQ). In intact animals, compound of formula IV dose-dependently reduced T levels with significant reductions observed at doses ≥3 mg/kg per day. Testosterone levels in intact animals treated with compound of formula IV were 2.6±1.7, 1.6±1.0, 0.7±0.4, BLOQ, and BLOQ ng/mL, following doses of 0.3, 1, 3, 10, and 30 mg/kg per day, respectively. In ORX animals the T levels were BLOQ for all groups treated with compound IV and the vehicle treated group. The results are for the intact animals are presented graphically in FIG. 10C (and FIG. 2) (BLOQ values are represented at the limit of quantitation for graphical purposes).

Figure 9:
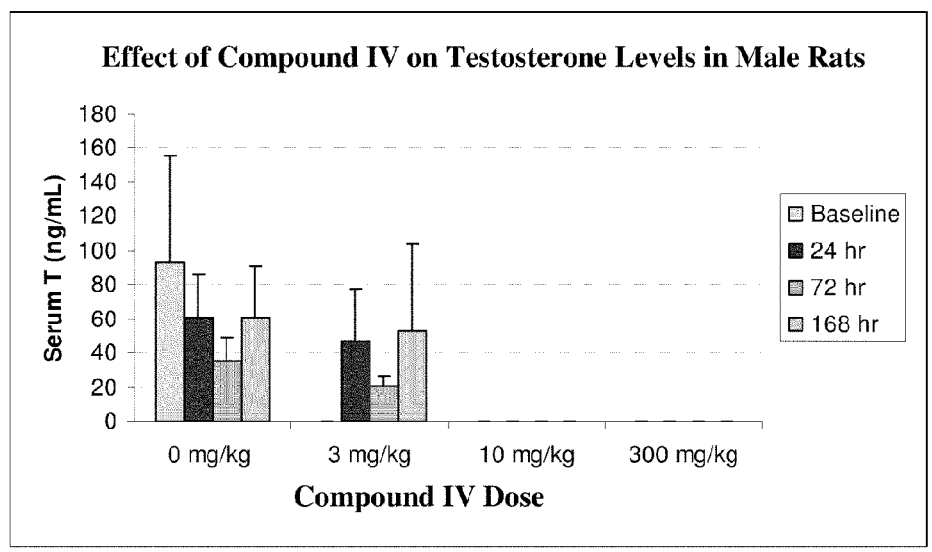
FIG. 9 depicts testosterone levels in intact rats treated with Compound IV after 24 h, 72 h and 168 h with dosages of 3 mg/kg, 10 mg/kg and 300 mg/kg. (See Example 9.)

Rapid and potent suppression of serum testosterone in intact male rats was measured by administering Compound IV with dosages of 3 mg/kg, 10 mg/kg and 300 mg/kg after 24 h, 72 h and 168 h as presented in FIG. 9.

Organ Weights (Table 6)

Figure 10D:
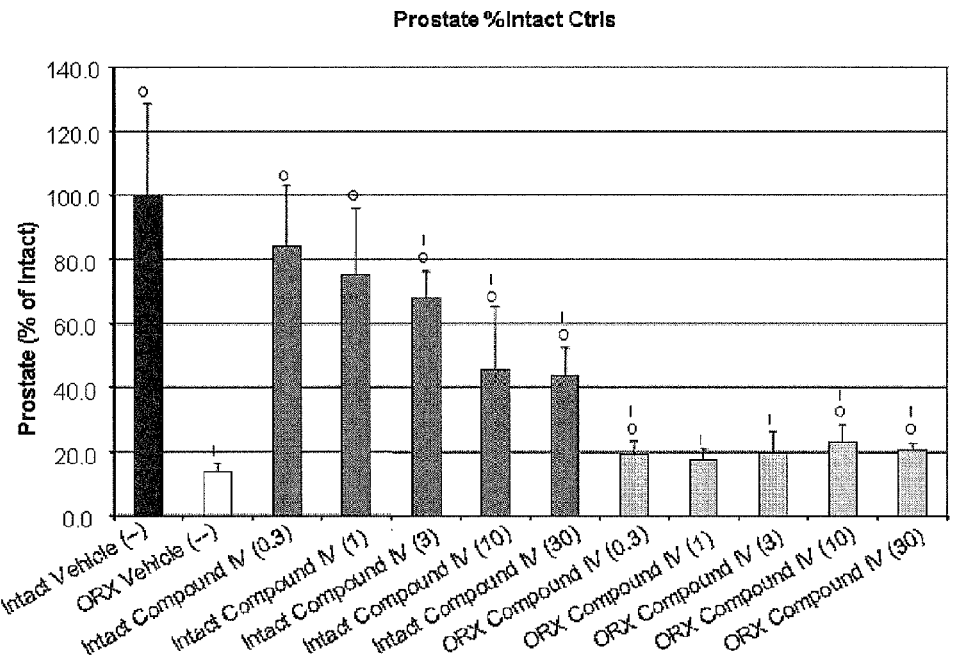
Figure 10E:
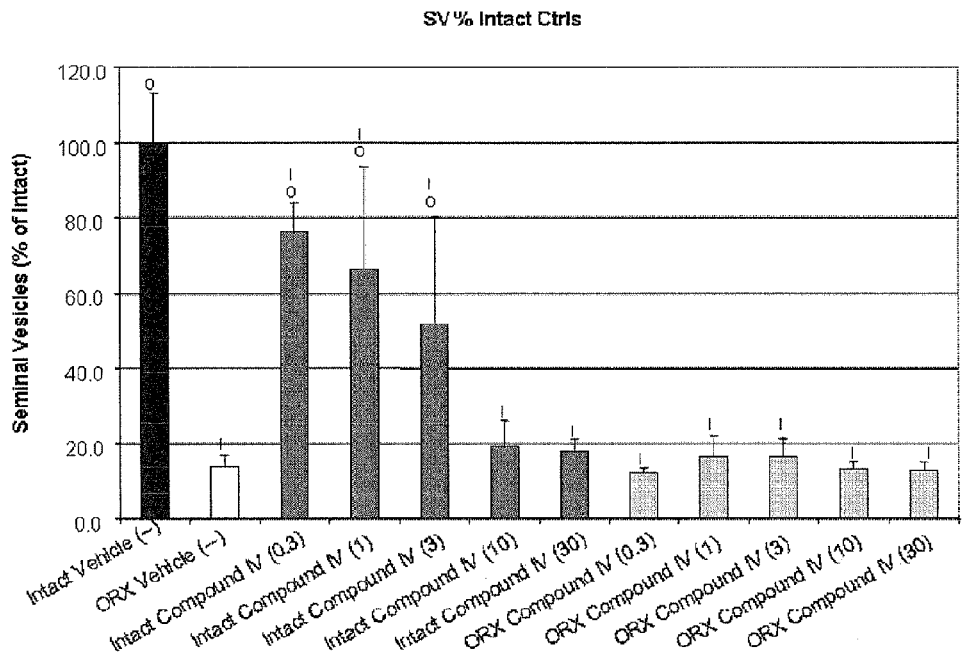
Figure 10F:
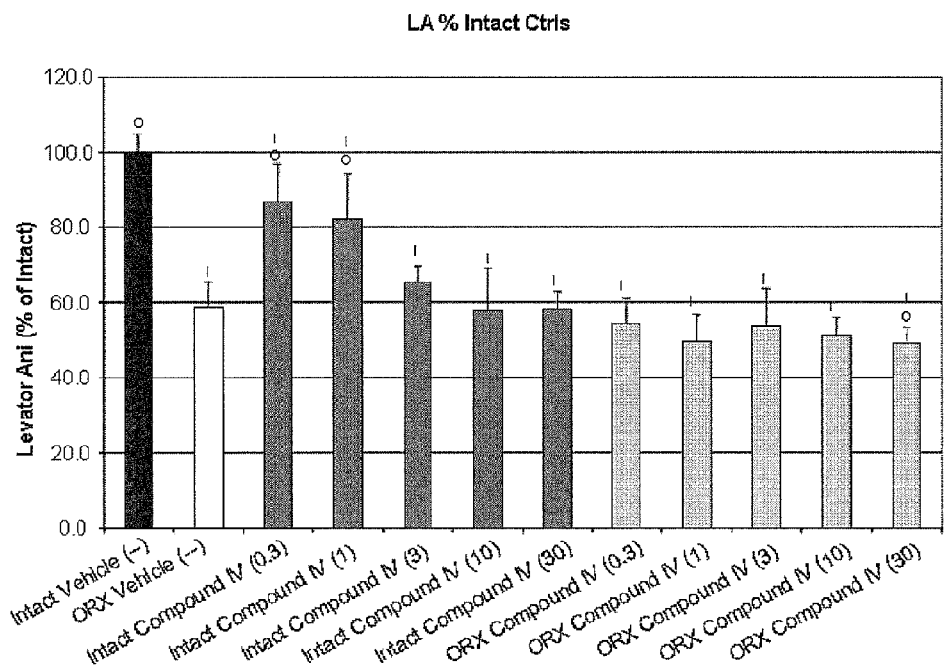

Prostate, seminal vesicles, and levator ani muscle weights were measured to confirm the suppression of T. The organ weights (mean±SD) are presented in FIGS. 10D, 10E and 10F respectfully. Dose-dependant decreases in prostate, seminal vesicles, and levator ani muscle weight were observed in intact animals treated with Compound IV. Prostate weights in intact animals were 84.0±19.2, 75.2±20.7, 68.2±8.1, 45.1±20.0, and 43.6±8.8, following doses of 0.3, 1, 3, 10, and 30 mg/kg/day, respectively. Prostate weights in ORX animals were 19.0±4.2, 17.4±3.4, 19.6±6.7, 22.9±5.4, and 20.6±2.1, following doses of 0.3, 1, 3, 10, and 30 mg/kg/day, respectively. Seminal vesicle weights in intact animals were 76.2±7.8, 66.3±27.2, 51.8±28.5, 19.1±7.0, and 17.9±3.3, following doses of 0.3, 1, 3, 10, and 30 mg/kg/day, respectively. Seminal vesicle weights in ORX animals were 12.2±1.3, 16.6±5.4, 16.5±4.8, 13.3±1.9, and 12.9±2.1, following doses of 0.3, 1, 3, 10, and 30 mg/kg/day, respectively. Levator ani weights in intact animals were 86.9±10.0, 82.1±12.1, 65.2±4.4, 57.8±11.2, and 58.1±4.7, following doses of 0.3, 1, 3, 10, and 30 mg/kg/day, respectively. Levator ani weights in ORX animals were 54.5±6.6, 49.6±7.0, 53.6±10.0, 51.1±4.9, and 49.2±4.2, following doses of 0.3, 1, 3, 10, and 30 mg/kg/day, respectively.

The LH suppression and organ weights data are summarized in Table 6.

TABLE 6

In vivo effects of the compound of formula IV on serum hormones and organ weight.

| Gonadal Status | Compound | Dose (mg/kg per day) | | LH (ng/mL) | FSH (ng/mL) | Prostate (% of Intact) | Seminal Vesicles (% of Intact) | Levator Ani Muscle (% of Intact) |
|---|---|---|---|---|---|---|---|---|
| Intact | Vehicle | — | Mean | $1.46^b$ | $20.9^b$ | $100.0^b$ | $100.0^b$ | $100.0^b$ |
|  |  |  | S.D. | 0.642 | 8.49 | 28.6 | 13.4 | 4.97 |
| ORX | Vehicle | — | Mean | $11.1^a$ | $93.5^a$ | $13.7^a$ | $14.0^a$ | $58.8^a$ |
|  |  |  | S.D. | 3.87 | 13.8 | 2.56 | 2.93 | 6.62 |
| Intact | Compound IV | 0.3 | Mean | $0.863^b$ | $17.3^b$ | $84.0^b$ | $76.2^{a,b}$ | $86.9^{a,b}$ |
|  |  |  | S.D. | 0.384 | 6.44 | 19.2 | 7.83 | 10 |
| Intact | Compound IV | 1 | Mean | $0.704^b$ | $15.7^b$ | $75.2^b$ | $66.3^{a,b}$ | $82.1^{a,b}$ |
|  |  |  | S.D. | 0.53 | 7.26 | 20.7 | 27.2 | 12.1 |
| Intact | Compound IV | 3 | Mean | $0.395^{a,b}$ | $18.4^b$ | $68.2^{a,b}$ | $51.8^{a,b}$ | $65.2^a$ |
|  |  |  | S.D. | 0.302 | 7.72 | 8.12 | 28.5 | 4.35 |
| Intact | Compound IV | 10 | Mean | $0.226^{a,b}$ | $9.25^{a,b}$ | $45.1^{a,b}$ | $19.1^a$ | $57.8^a$ |
|  |  |  | S.D. | 0.165 | 3.97 | 20 | 6.98 | 11.2 |
| Intact | Compound IV | 30 | Mean | $0.236^{a,b}$ | $6.25^{a,b}$ | $43.6^{a,b}$ | $17.9^a$ | $58.1^a$ |
|  |  |  | S.D. | 0.176 | 1.82 | 8.75 | 3.33 | 4.71 |
| ORX | Compound IV | 0.3 | Mean | $15.4^a$ | $116^a$ | $19.0^{a,b}$ | $12.2^a$ | $54.5^a$ |
|  |  |  | S.D. | 2.94 | 17.2 | 4.19 | 1.31 | 6.56 |
| ORX | Compound IV | 1 | Mean | $13.5^a$ | $114^a$ | $17.4^a$ | $16.6^a$ | $49.6^a$ |
|  |  |  | S.D. | 2.18 | 22.3 | 3.4 | 5.36 | 7.04 |
| ORX | Compound IV | 3 | Mean | 6.5 | $65.2^a$ | $19.6^a$ | $16.5^a$ | $53.6^a$ |
|  |  |  | S.D. | 5.63 | 31.9 | 6.67 | 4.82 | 10 |
| ORX | Compound IV | 10 | Mean | $0.425^{a,b}$ | $27.6^b$ | $22.9^{a,b}$ | $13.3^a$ | $51.1^a$ |
|  |  |  | S.D. | 0.135 | 8.16 | 5.44 | 1.91 | 4.88 |
| ORX | Compound IV | 30 | Mean | $0.368^{a,b}$ | $15.1^b$ | $20.6^{a,b}$ | $12.9^a$ | $49.2^{a,b}$ |
|  |  |  | S.D. | 0.119 | 4.11 | 2.08 | 2.14 | 4.21 |

[a] $P < 0.05$ versus Intact Vehicle.
[b] $P < 0.05$ versus ORX Vehicle

Example 10

Recovery of Testosterone Levels Following Suppression by Compound IV in Rats and Monkeys The reversibility of chemical castration with Compound IV was studied.

Materials and Methods:

Thirty-five (35) male Sprague-Dawley rats weighing approximately 200 g were maintained on a 12-h light/dark cycle with food (2016 Teklad Global 16% Protein Rodent Diet, Harlan, Madison, Wis.) and water available ad libitum. The animal protocol was reviewed and approved by the Institutional Animal Care and Use Committee of the University of Tennessee.

The test article for this study was weighed and dissolved in PEG 300 (100%) (Acros Organics, NJ) to prepare the appropriate dose formulations. Animals were randomly assigned to one of the ten treatment groups (n =5 animals/group). Treatment groups are listed in Table 7. The animals were housed in groups of 2 to 3 animals per cage. Group 1 was sacrificed at the initiation of the study (Day 1) for determination of baseline testosterone levels in intact animals. Groups 2-7 received daily doses of 1, 3, or 30 mg/kg via oral gavage (~200 uL) for three days. Groups 2, 3, and 4 were sacrificed on Day 4 to measure maximal testosterone suppression. Groups 5, 6, and 7 were allowed to recover for 14 days with a drug free washout period.

TABLE 7

Treatment groups.

| Group | Compound IV P.O. Dose | Treatment |
|---|---|---|
| Group 1 | — | Baseline |
| Group 2 | 1 mg/kg for 3 days | No Recovery |
| Group 3 | 3 mg/kg for 3 days | No Recovery |
| Group 4 | 30 mg/kg for 3 days | No Recovery |
| Group 5 | 1 mg/kg for 3 days | 14 day recovery |
| Group 6 | 3 mg/kg for 3 days | 14 day recovery |
| Group 7 | 30 mg/kg for 3 days | 14 day recovery |

Results:

Serum testosterone levels in intact rats were 6.4±3.1 ng/mL (mean±S.D) at baseline. Compound IV administered at doses of 3 and 30 mg/kg for three days significantly suppressed serum testosterone levels to 1.47±0.26 and 1.62±0.49 ng/mL, respectively. No significant suppression was observed in animals that received 1 mg/kg of Compound IV for three days. Most importantly, serum testosterone levels were 3.3±1.92, 3.00±1.06 and 3.8±1.72 in animals that received 1, 3, or 30 mg/kg, respectively, of Compound IV for three days when measured after a 14 day recovery period, and were not statistically significantly differences from baseline serum testosterone concentrations in intact rats as depicted in FIG. 23.

This study confirms previous results showing that Compound IV quickly suppresses serum testosterone levels in intact male rats. We observed suppression of serum testosterone levels in dose groups receiving ≥3 mg/kg/day for 3 days. A significant decrease in serum testosterone was not observed with the 1 mg/kg dose group. However, within 14 days of recovery, serum testosterone levels had returned back to the level of intact controls. This study shows that pharmacologic castration by Compound IV is reversible in rats.

The effect of Compound IV on suppression and recovery of testosterone levels in intact male monkeys was evaluated in conjunction with an oral pharmacokinetic study. Three treatment naïve male Cynomolgus monkeys (2 to 3 years old) were administered Compound IV at 30 mg/kg daily by oral gavage for 7 consecutive days. Blood samples were collected and divided into serum and plasma for testosterone and Compound IV quantitative measurements, respectively. Results show that daily oral doses of Compound IV significantly decreased circulating androgen (primarily testosterone and dihydrotestosterone) levels in all three male monkeys by up to 47% compared to baseline levels (levels of 1591±72.5, 997±104, and 852±136 ng/mL, respectively for baseline, Day 2 and Day 6 of treatment [mean±SEM]). Following a 18-day drug-free recovery period, androgen levels returned to normal, and were not significantly different from pre-treatment baseline levels (1757.7±369.5 ng/mL after recovery).

Example 11

Bone Preservation Despite Reduction of LH and Testosterone in Rats (Table 8)

The effect of compound of formula IV on treatment on bone was studied. Orally administered compound of formula IV completely prevented the bone loss associated with LH suppression in intact male rats. Significant reduction of LH was induced by the compound of formula IV in intact animals at dose levels ≥10 mg/kg per day. Although at 1 mg/kg per day, compound of formula IV did not significantly reduce LH, significant reductions in prostate, seminal vesicles, and levator ani muscle were apparent at this dose indicating that the reduction in circulating testosterone was physiologically relevant to these androgen responsive organs. However, 1 mg/kg per day compound of formula IV maintained trabecular bone volume (measured in the distal femur) at the level of intact controls. When administered at doses of 10 and 30 mg/kg per day, compound of formula IV increased bone volume in the distal femur significantly above that of intact controls. These data show that compound IV increased trabecular bone mineral density (BMD) and percent bone volume at a dose level that reduces LH levels in intact rats. Data from this study are presented in Table 8.

TABLE 8

In vivo effects of Compound IV on rat bone, organ weight, and serum hormone parameters.

| Gonadal Status | Compound | Dose (mg/kg per day) | | Bone Mineral Density (g/cm³) | Percent Bone Volume (BV/TV) (%) | Prostate (% of Intact) | Seminal Vesicles (% of Intact) | Levator Ani Muscle (% of Intact) | FSH (ng/mL) | LH (ng/mL) |
|---|---|---|---|---|---|---|---|---|---|---|
| Intact | Vehicle | — | Mean | 0.274[b] | 20.2[b] | 100.0[b] | 100.0[b] | 100.0[b] | 9.93[b] | 0.781[b] |
| | | | S.D. | 0.033 | 3.57 | 11.1 | 15.9 | 11.6 | 2.94 | 0.263 |
| ORX | Vehicle | — | Mean | 0.224[a] | 15.4[a] | 14.8[a] | 10.3[a] | 59.4[a] | 117[a] | 22.0[a] |
| | | | S.D. | 0.025 | 2.6 | 4.08 | 0.767 | 7.26 | 40.2 | 5.81 |
| Intact | Compound IV | 1 | Mean | 0.273[b] | 20.0[b] | 69.2[a,b] | 44.6[a,b] | 80.0[a,b] | 14.1[a,b] | 0.820[b] |
| | | | S.D. | 0.04 | 4.08 | 13.5 | 15.7 | 6.69 | 4.07 | 0.392 |
| Intact | Compound IV | 10 | Mean | 0.326[a,b] | 25.9[a,b] | 30.7[a,b] | 12.8[a,b] | 58.1[a] | 5.48[a,b] | 0.060[a,b] |
| | | | S.D. | 0.048 | 4.76 | 12.4 | 0.886 | 9.68 | 1.97 | 0.092 |

TABLE 8-continued

In vivo effects of Compound IV on rat bone, organ weight, and serum hormone parameters.

| Gonadal Status | Compound | Dose (mg/kg per day) | | Bone Mineral Density (g/cm$^3$) | Percent Bone Volume (BV/TV) (%) | Prostate (% of Intact) | Seminal Vesicles (% of Intact) | Levator Ani Muscle (% of Intact) | FSH (ng/mL) | LH (ng/mL) |
|---|---|---|---|---|---|---|---|---|---|---|
| Intact | Compound IV | 30 | Mean S.D. | 0.326$^{a,b}$ 0.046 | 25.5$^{a,b}$ 4.49 | 30.1$^{a,b}$ 17.4 | 14.4$^{a,b}$ 1.45 | 56.1$^a$ 4.67 | 6.32$^{a,b}$ 3.4 | 0.078$^{a,b}$ 0.114 |

$^a$P < 0.05 versus Intact Vehicle.
$^b$P < 0.05 versus ORX Vehicle

Example 12

Effects on 17β Hydroxysteroid Dehydrogenase 5 (17β-HSD5) Enzyme Activity

HSD family members are involved in the conversion of circulating steroids. 17β-HSD5 converts androstenedione to testosterone and estrone to estradiol. In addition, it is also involved in prostaglandin synthesis. Here the ability of some select compounds of this invention to inhibit 17β-HSD5 activity was demonstrated.

Method

Human 17β-HSD5 was cloned in pGEX 4t1 vector and purified protein was prepared. The purified protein was incubated with the representative compound of this invention, $^{14}$C androstenedione and NADPH in an appropriate buffer. The synthesized testosterone was extracted using ethyl acetate, air dried, spotted and run on a thin layer chromatography (TLC) plate. The TLC was exposed to phosphorimager and the intensity of testosterone band was quantified. Indomethcin was used as a positive control (LHRH agonist).

Results

Figure 3:
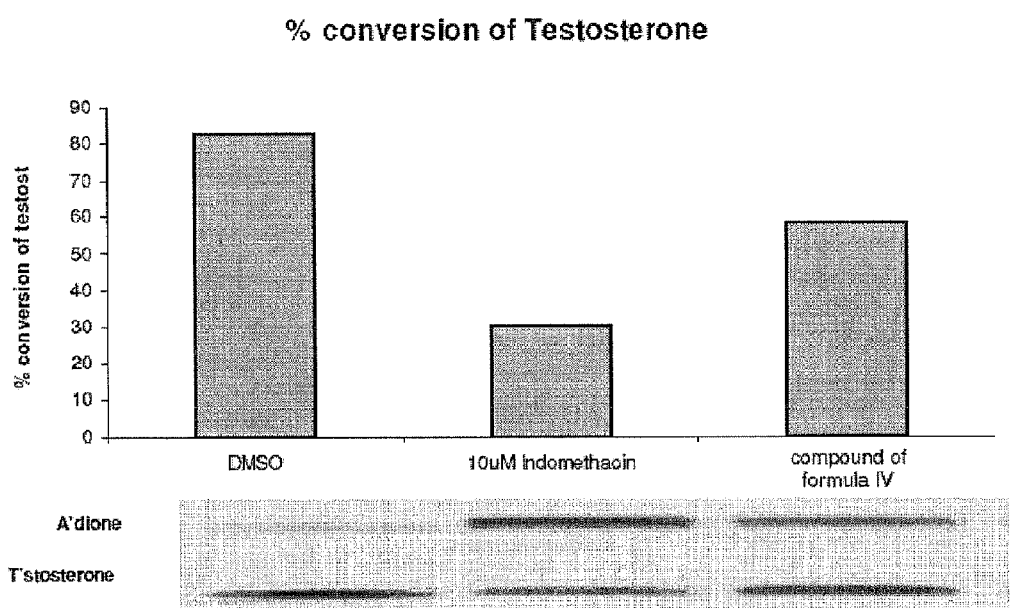
FIG. 3 depicts the inhibitory effect of Compound IV on 17β-HSD5 enzyme activity. (See Example 12.)

Compound IV was tested and had partial inhibitory effect on 17β-HSD5 enzyme activity. The positive control (LHRH agonist), indomethacin as expected exhibited strong inhibition of this enzyme, as presented in FIG. 3.

Example 13

Toxicity Studies

Figure 4:
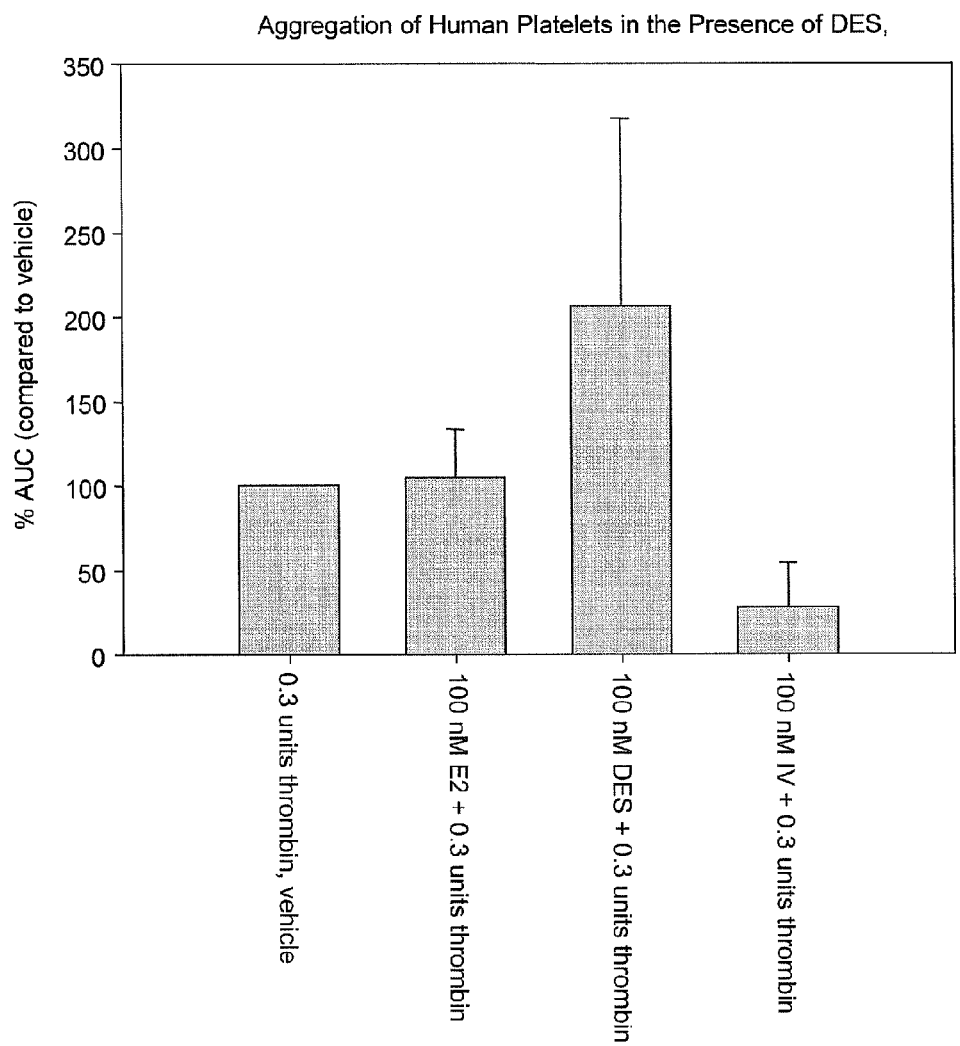
FIG. 4 depicts in vitro aggregation of human platelets in the presence of DES, 17β-estradiol (E2), and Compound IV. Platelet Rich Plasma (PRP) was incubated with vehicle, E2, DES, or Compound IV for 30 seconds before inducing aggregation with 0.3 units of thrombin. Aggregation was monitored for 5 minutes and expressed as a percentage of vehicle control. (See Example 13.)

A study was conducted to compare the thrombotic potential of Compound IV and diethylstilbestrol (DES, positive control) using the in vitro human platelet aggregation assay. Blood from healthy male donors was used in the study since males are the intended treatment population for Compound IV (LH suppression). Platelet rich plasma was preincubated with either estradiol (E2), DES, Compound IV or vehicle for 30 seconds, and then thrombin (0.3 units) was added to induce platelet aggregation. Results of the study show that preincubation with DES increased the thrombin-induced platelet aggregation by approximately 10-fold. However, Compound IV and estradiol decreased aggregation in the platelet rich plasma. These data demonstrate that Compound IV reduced the reactivity of human platelets in vitro compared to DES, and suggest that Compound IV may have lower thromboembolic potential than DES (FIG. 4).

Example 14

Effect of Compound IV on Hot Flashes

A study was conducted to investigate the effect of Compound IV on hot flashes using the morphine dependent rat model (MD model) which was developed by Simpkins et.al (1983) and was shown to have several similarities to the menopausal hot flash. In addition to the similarities to the human condition, this experimental animal model has a short turn around time which makes it a useful high throughput screening tool for identifying compounds that can alleviate vasomotor symptoms using the tail skin temperature (TST). TST probes TA-40 (Data Sciences International, MN) were taped to the base of the tails and baseline temperatures were obtained for 15 minutes. After 15 minutes the animals were treated with naloxone (1 mg/kg, SQ) to reverse the effects of the morphine. Tail skin temperature (TST) was measured for one hour post-naloxone treatment with a sampling frequency of 5 secs throughout the course of the experiment. Following the data acquisition, the moving average of the temperature recorded every 60 seconds for each animal was calculated and further analyzed. Baseline temperature was computed as the average temperature acquired over the 15 minutes preceding naloxone administration. The area under the curve (AUC) was calculated by subtracting all the values post-naloxone administration from the baseline using a linear trapezoid method.

Figure 13:
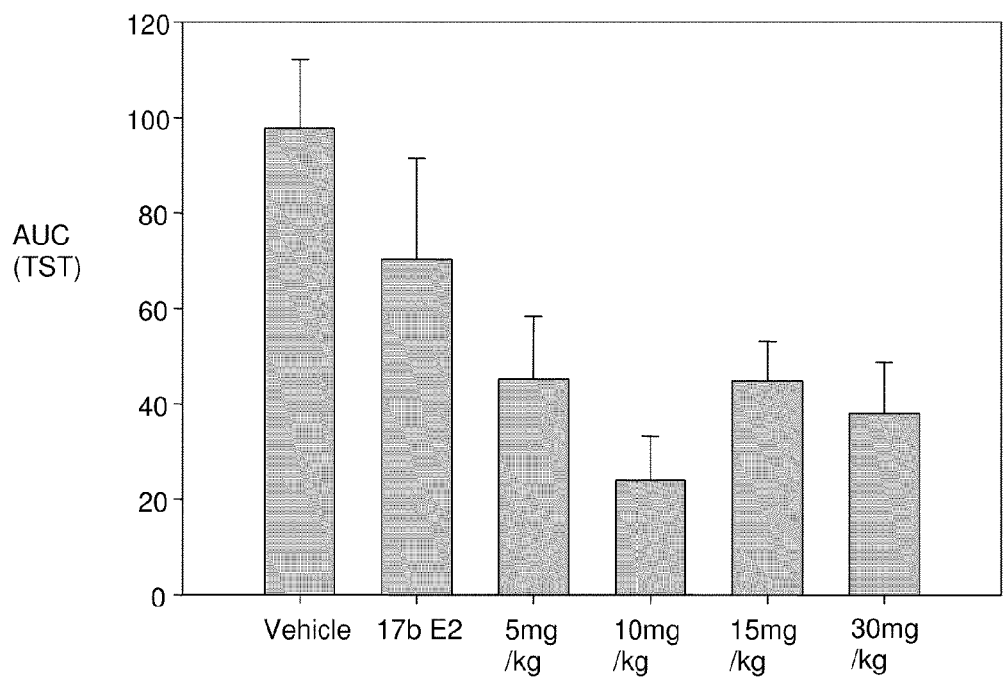
FIG. 13 depicts effect of Compound IV on attenuation of hot flashes in morphine withdrawal model with 5 mg/kg, 10 mg/kg, 15 mg/kg and 30 mg/kg dosages. N=7 animals per group. 17β-E2 was used at 5 mg/kg in 100% DMSO. (See Example 14.)

Compound IV attenuated hot flushes in the morphine withdrawal model (see FIG. 13) with the best results at 10 mg Compound IV. 17β E2 was used at 5 mg/kg in 100% DMSO.

Example 15

Compound IV Versus DES in Rats

Prior to the introduction of LHRH agonists, castrate testosterone levels were achieved by increasing estrogen activity in the pituitary via estrogens, primarily diethylstilbestrol (DES). DES was equally effective as LHRH agonists at suppressing testosterone to castrate levels. Patients treated with DES did not have hot flashes or bone loss, but did have gynecomastia at higher rates than ADT with LHRH agonists. Unfortunately, highly potent, pure estrogens, like DES and estradiol, are often associated with a high risk of severe cardiovascular and thromboembolic complications which have limited their clinical use. It has been hypothesized, but not proven, that the increased risk of venous thromboembolic complications with DES is due to its cross-reactivity with other hormone receptors. In vitro studies with human platelets showed that Compound IV had much lower procoagulatory activity than DES. Thus, Compound IV, an ER-alpha selective agonist, may deliver the prostate cancer benefits of DES and also deliver the benefits of an LHRH agonist without causing osteoporosis or adverse lipid profiles.

Figure 11:
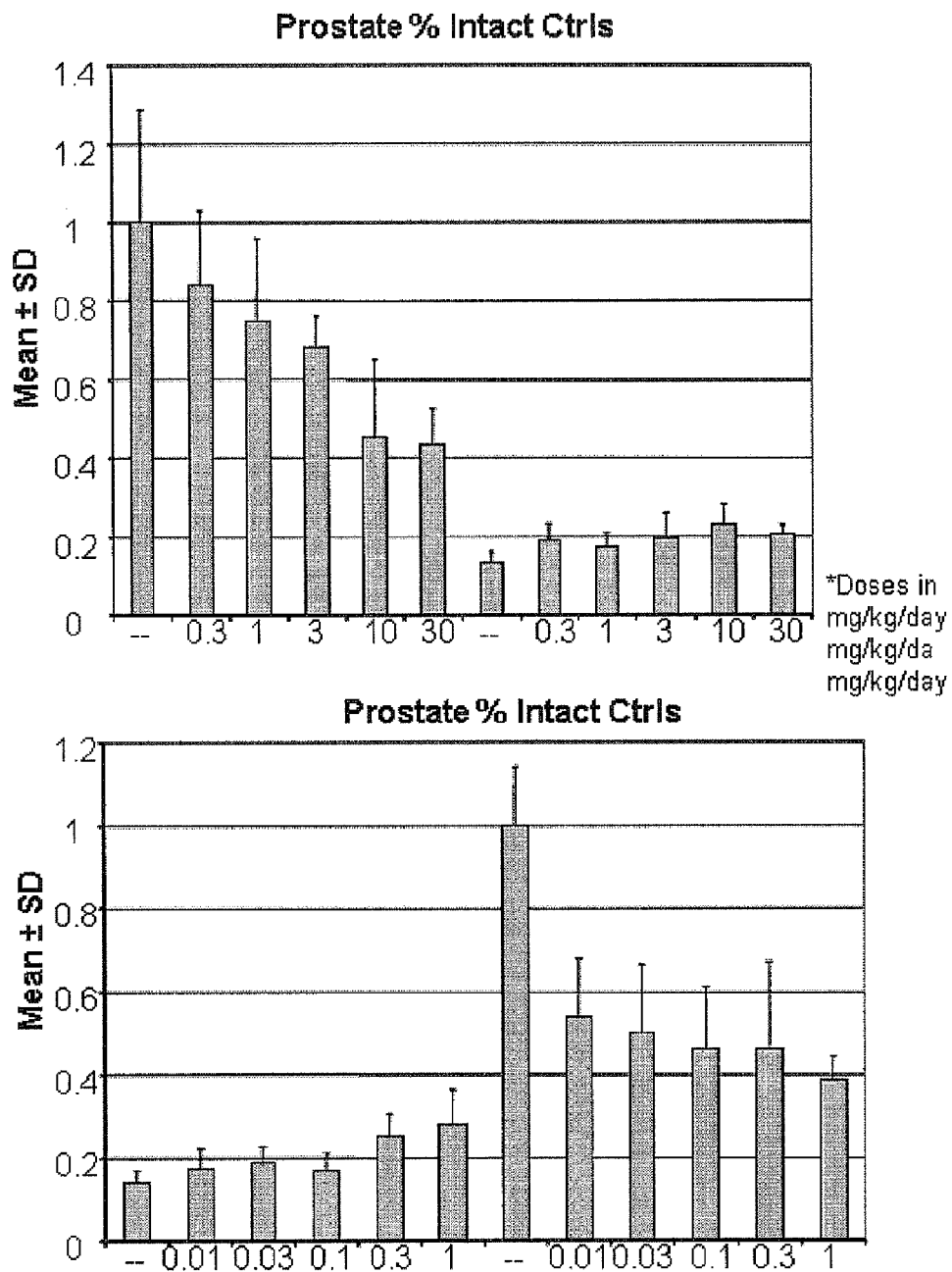
FIG. 11 depicts prostate size in intact and ORX rats by administering Compound IV (FIG. 11A) and DES (FIG. 11B) at different dosages. (See Example 15.)

Compound IV is as effective as DES in reducing prostate size in rats (FIG. 11A) and presenting moderate increase in prostate size of ORX rats (FIG. 11B).

Figure 12A:
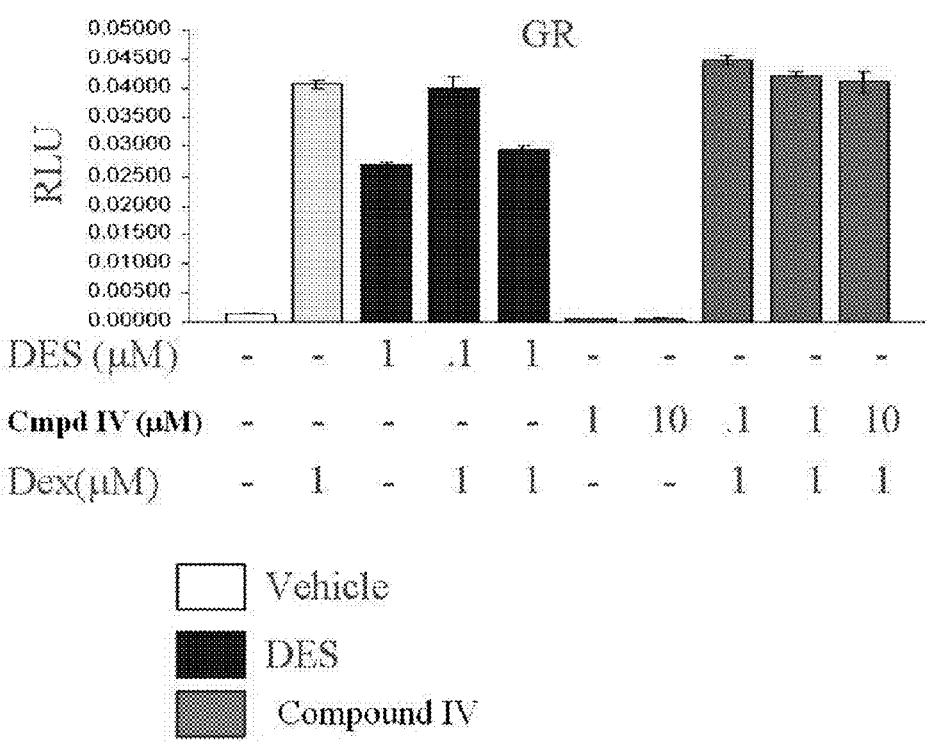
FIG. 12 depicts differences between DES and Compound IV; DES crossreacts with glucocorticoid receptor (GR) while Compound IV does not (FIG. 12A); DES crossreacts with androgen receptor (AR). It mildly stimulates AR action and mildly inhibits (i.e., it is a partial agonist/antagonist) while Compound IV does not (FIG. 12B); DES abrogates estrogen related receptor (ERR) transactivation, while Compound IV does not (FIG. 12C). (See Example 15.)
Figure 12B:
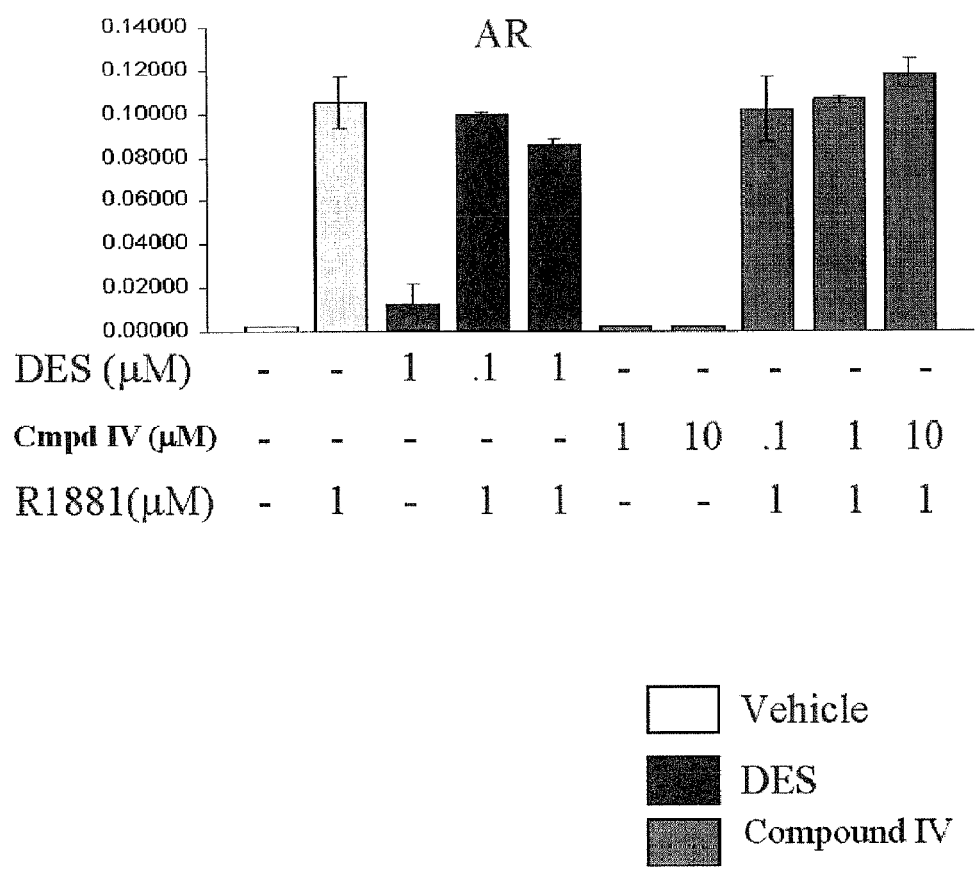
Figure 12C:
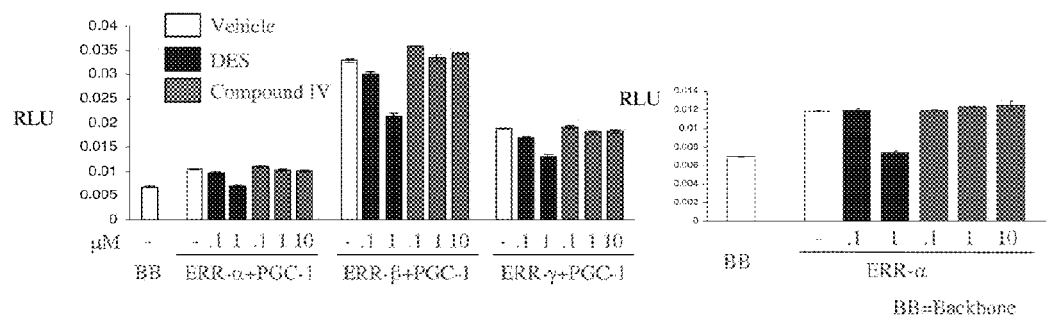

Differences between DES and Compound IV are presented in FIGS. 12A-12C, where DES crossreacted with glucocorticoid receptor (GR) (FIG. 12A) and androgen receptor (AR) (FIG. 12B) while Compound IV did not. In addition, DES antagonized estrogen related receptor (ERR) transactivation while Compound IV did not. Compound IV failed to cross-react with any of the three ERR isoforms (ERR-α, ERR-β and ERR-γ) as depicted in FIG. 12C Example 16

Monkey Toxicity Study—90 Days

Figure 14:
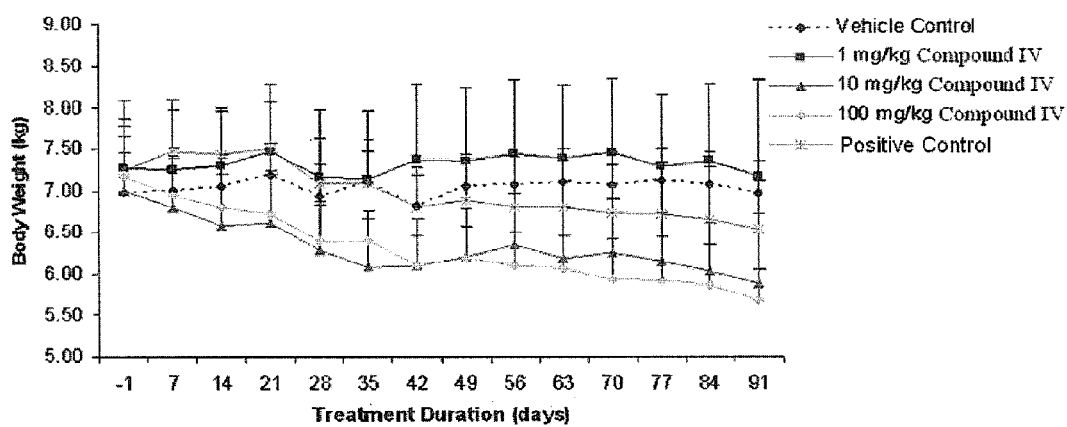
FIG. 14 depicts dose dependent body weight (kg) reductions of monkeys (~20% at 100 mg/kg) by administering Compound IV for 91 days. No sign of gynecomastia or hyperestrogenicity was observed. (See Example 16.)

Colony-bred cynomolgus macaques of Mauritius origin were obtained. The prospective study was designed as a 39-week oral pharmacology and toxicology evaluation of Compound IV and positive control (LHRH agonist) in the male cynomolgus monkey with a 13-week interim period. A total of 39 sexually mature male monkeys, 5 to 8 years of age, were randomly assigned to five groups prior to treatment initiation. Groups included: 1) vehicle control, 2) 1 mg/kg Compound IV, 3) 10 mg/kg Compound IV, 4) 100 mg/kg Compound IV, and 5) positive control (LHRH agonist). Drug was delivered orally by cage-side administration once daily for 39 weeks with vehicle control article (Tween 80/PRANG™) for Groups 1 and 5, or Compound IV in vehicle for Groups 2, 3, and 4. Dose levels of Compound IV were 1, 10, and 100 mg/kg/day for Groups 2, 3, and 4, respectively. Oral doses were delivered in a 10 mL/kg dose volume as calculated based on most recent available body weight for each animal (FIG. 14). Animals in Group 5 also received a once-daily subcutaneous injection of positive control (LHRH agonist) (0.02 mL constant volume) for the 39 week study period. General appearance and clinical signs were observed and recorded daily. Routine evaluations and select other study investigations were performed as indicated in the study protocol. Select parameters include, but are not limited to, testosterone, prostate specific antigen (PSA), and prostate volume and weight.

Testosterone and total PSA levels were quantified in serum samples (following standard procedure) using an enzyme immunoassay (EIA) method and chemiluminescence immunoassay (LIA, ALPCO Diagnostics, Salem N.H.), respectively. Blood samples for testosterone evaluations were collected from all animals (in fasted state) at baseline (i.e., prior to commencement of treatment) and on Days 1, 3, 7, 14, 28, 64, and 90. Blood samples for PSA determinations were collected from all animals (in fasted state) at baseline and during Week 6. For the purpose of discussion, results for samples with concentrations below the limit of quantitation (BLQ) for the testosterone and PSA assays are calculated as ½ of the lower limit of quantitation (LLOQ) of the assay, and are considered as "Estimated final concentrations". Data in Tables 9 through 16 are presented as "Quantifiable concentrations only" (i.e., excludes BLQ values) in addition to "Estimated final concentrations" (i.e., samples with BLQ result included as ½ LLOQ of assay). Prostate volume was measured in live animals under anesthesia using a transrectal ultrasound (TRUS) procedure at baseline and Week 6. The width and height of prostate were recorded. Prostate volumes were calculated as width*width*height*pi/6 [ref] and were normalized to body weight. The wet weight of prostate was recorded at necropsy after trimming the tissue free of fat and extraneous tissue.

Figure 15:
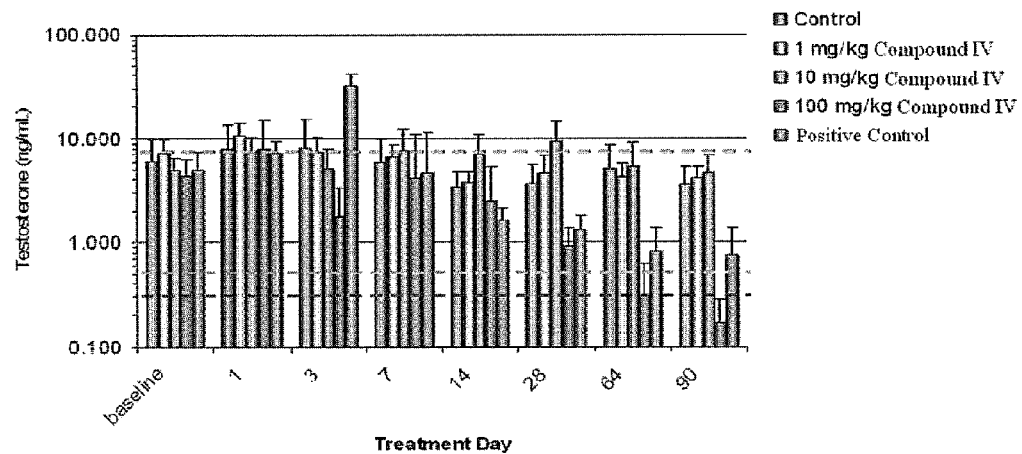
FIG. 15 depicts dose dependent serum testosterone level reductions (ng/mL) in monkeys after daily oral administration of Compound IV compared to positive control (LHRH agonist). Dotted line indicates the testosterone level of chemically castrated patients and the bold dashed line indicates the testosterone level of surgically castrated monkeys. (See Example 16.)

Results and Discussion:

Serum testosterone levels are presented in FIG. 15 and Tables 9 through 12. At baseline, the testosterone levels for all monkeys on the study were in the normal range for sexually mature adult male cynomolgus monkeys. However, testosterone levels were significantly reduced in monkeys receiving Compound IV at 100 mg/kg/day and in monkeys treated with positive control (LHRH agonist). Testosterone levels in the positive control (LHRH agonist) group illustrated a biphasic change, with an initial significant increase (i.e., flare) of 47.4% and 547% ($p<0.01$) on Days 1 and 3, respectively, followed by decreases of 3.6%, 67%, 73%, 83%, and 85% on Days 7, 14, 28, 64 and 90 (see FIG. 15 and Tables 9 to 12). A similar flare was not observed for any animal treated with Compound IV even at the highest dose level (i.e., 100 mg/kg/day). Dose and treatment duration were important to the pharmacologic action of Compound IV, where doses of 100 mg/kg/day suppressed the serum testosterone by 60%, 51%, 42%, 79% and 92% on Days 3, 7, 14, 28 and 64, respectively, relative to the baseline value (see FIG. 15 and Tables 9 and 10). After 90 days of treatment with 100 mg/kg/day Compound IV, the testosterone level in 6 of 10 Group 4 monkeys was reduced to concentrations below the limit of quantification of the assay (refer to Table 11). The mean serum testosterone level in Group 4 monkeys was reduced by 96% compared to respective baseline values ("Estimated final concentrations", i.e., testosterone levels for 6/10 monkeys with BLQ values are calculated as 50% of the LLOQ concentration, see Table 10). It is important to note that by Day 90, Compound IV at 100 mg/kg/day reduced serum testosterone to levels significantly lower than the positive control (LHRH agonist) ($p=0.013$).

TABLE 9

Mean serum testosterone levels (ng/mL) in intact male monkeys after daily oral administration of Compound IV; @Estimated final concentrations.

| Day | Vehicle Control | | | Compound IV 1 mg/kg | | | Compound IV 10 mg/kg | | | Compound IV 100 mg/kg | | | Positive control (LHRH agonist) | | |
|---|---|---|---|---|---|---|---|---|---|---|---|---|---|---|---|
| | Mean | SEM | N | Mean | SEM | N | Mean | SEM | N | Mean | SEM | N | Mean | SEM | N |
| 0 baseline | 6.1 | 1.2 | 10 | 7.3 | 1.0 | 6 | 4.9 | 0.6 | 6 | 4.4 | 0.6 | 10 | 4.9 | 0.9 | 7 |
| 1 | 8.0 | 1.7 | 10 | 11 | 1.6 | 6 | 7.6 | 1.1 | 6 | 8.0 | 2.2 | 10 | 7.2 | 0.8 | 7 |
| 3 | 8.2 | 2.3 | 10 | 7.4 | 1.2 | 6 | 5.1 | 1.1 | 6 | 1.8* | 0.5 | 10 | 32#$ | 3.8 | 7 |
| 7 | 5.9 | 1.2 | 10 | 6.7 | 0.8 | 6 | 7.7 | 1.9 | 6 | 2.2* | 0.7 | 9 | 4.7 | 2.6 | 7 |
| 14 | 3.4 | 0.5 | 10 | 3.8 | 0.4 | 6 | 7.1 | 1.6 | 6 | 2.6 | 0.9 | 9 | 1.6# | 0.2 | 7 |
| 28 | 3.8 | 0.6 | 10 | 4.7 | 0.9 | 6 | 9.4 | 2.1 | 6 | 0.9* | 0.2 | 10 | 1.3# | 0.2 | 7 |

TABLE 9-continued

Mean serum testosterone levels (ng/mL) in intact male monkeys after daily oral administration of Compound IV; @Estimated final concentrations.

| | Vehicle Control | | | Compound IV 1 mg/kg | | | Compound IV 10 mg/kg | | | Compound IV 100 mg/kg | | | Positive control (LHRH agonist) | | |
|---|---|---|---|---|---|---|---|---|---|---|---|---|---|---|---|
| Day | Mean | SEM | N | Mean | SEM | N | Mean | SEM | N | Mean | SEM | N | Mean | SEM | N |
| 64 | 5.1 | 1.1 | 10 | 4.3 | 0.6 | 6 | 5.4 | 1.5 | 6 | 0.3* | 0.1 | 9 | 0.8[#$] | 0.2 | 7 |
| 90 | 3.6 | 0.6 | 9 | 4.2 | 0.6 | 4 | 4.6 | 1.0 | 5 | 0.2* | 0.0 | 10 | 0.8[#$] | 0.2 | 7 |

Testosterone assay LLOQ = 0.246 ng/mL;
@BLOQ values are calculated as 0.123 ng/mL, half of the LLOQ.
*Statistically significant (p < 0.05) Compound IV 100 mg/kg vs. Vehicle Control
[#]Statistically significant (p < 0.05) Positive control (LHRH agonist) vs. Vehicle Control
[$]Statistically significant (p < 0.05) Positive control (LHRH agonist) vs. Compound IV 100 mg/kg

TABLE 10

Percentage change (%) of mean serum testosterone levels compared to baseline; @ Estimated final concentrations.

| Day | Vehicle Control | Compound IV 1 mg/kg | Compound IV 10 mg/kg | Compound IV 100 mg/kg | Positive Control |
|---|---|---|---|---|---|
| 1 | 31 | 44 | 54 | 82 | 47 |
| 3 | 35 | 1.8 | 3.5 | −60 | 547 |
| 7 | −3.2 | −8.1 | 57 | −51 | −3.6 |
| 14 | −44 | −48 | 45 | −42 | −67 |
| 28 | −38 | −35 | 92 | −79 | −73 |
| 64 | −16 | −41 | 11 | −92 | −83 |
| 90 | −42 | −42 | −5.5 | −96 | −85 |

Testosterone assay LLOQ = 0.246 ng/mL;
@ BLQ values are calculated as 0.123 ng/mL, half of the LLOQ.

TABLE 11

Mean serum testosterone levels (ng/mL) in intact male monkeys after daily oral administration Compound IV; [λ] Quantifiable concentrations only

| | Vehicle Control | | | Compound IV 1 mg/kg | | | Compound IV 10 mg/kg | | | Compound IV 100 mg/kg | | | Positive control (LHRH agonist) | | |
|---|---|---|---|---|---|---|---|---|---|---|---|---|---|---|---|
| Day | Mean | SEM | N | Mean | SEM | N | Mean | SEM | N | Mean | SEM | N | Mean | SEM | N |
| 0 baseline | 6.1 | 1.2 | 10 | 7.3 | 1.0 | 6 | 4.9 | 0.6 | 6 | 4.4 | 0.6 | 10 | 4.9 | 0.9 | 7 |
| 1 | 8.0 | 1.7 | 10 | 11 | 1.6 | 6 | 7.6 | 1.1 | 6 | 8.0 | 2.2 | 10 | 7.2 | 0.8 | 7 |
| 3 | 8.2 | 2.3 | 10 | 7.4 | 1.2 | 6 | 5.1 | 1.1 | 6 | 1.8 | 0.5 | 10 | 32 | 3.8 | 7 |
| 7 | 5.9 | 1.2 | 10 | 6.7 | 0.8 | 6 | 7.7 | 1.9 | 6 | 2.2 | 0.7 | 9 | 4.7 | 2.6 | 7 |
| 14 | 3.4 | 0.5 | 10 | 3.8 | 0.4 | 6 | 7.1 | 1.6 | 6 | 2.6 | 0.9 | 9 | 1.6 | 0.2 | 7 |
| 28 | 3.8 | 0.6 | 10 | 4.7 | 0.9 | 6 | 9.4 | 2.1 | 6 | 0.9 | 0.2 | 10 | 1.3 | 0.2 | 7 |
| 64 | 5.1 | 1.1 | 10 | 4.3 | 0.6 | 6 | 5.4 | 1.5 | 6 | 0.3 | 0.1 | 9 | 0.8 | 0.2 | 7 |
| 90 | 3.6 | 0.6 | 9 | 4.2 | 0.6 | 4 | 4.6 | 1.0 | 5 | 0.2 | 0.1 | 4 | 0.8 | 0.2 | 7 |

Testosterone assay LLOQ = 0.246 ng/mL;
[λ] BLQ values are excluded.

TABLE 12

Percentage change (%) of mean testosterone levels compared to baseline; [λ] Quantifiable concentrations only.

| Day | Vehicle Control | Compound IV 1 mg/kg | Compound IV 10 mg/kg | Compound IV 100 mg/kg | Positive Control |
|---|---|---|---|---|---|
| 1 | 31 | 44 | 54 | 82 | 47 |
| 3 | 35 | 1.8 | 3.5 | −60 | 547 |
| 7 | −3.2 | −8.1 | 57 | −51 | −3.6 |
| 14 | −44 | −48 | 45 | −42 | −67 |

TABLE 12-continued

Percentage change (%) of mean testosterone levels compared to baseline; $^\lambda$ Quantifiable concentrations only.

| Day | Vehicle Control | Compound IV 1 mg/kg | Compound IV 10 mg/kg | Compound IV 100 mg/kg | Positive Control |
|---|---|---|---|---|---|
| 28 | −38 | −35 | 92 | −79 | −73 |
| 64 | −16 | −41 | 11 | −92 | −83 |
| 90 | −42 | −42 | −5.5 | −95 | −85 |

Testosterone assay LLOQ = 0.246 ng/mL;
$^\lambda$ BLQ values are excluded.

Figure 16:
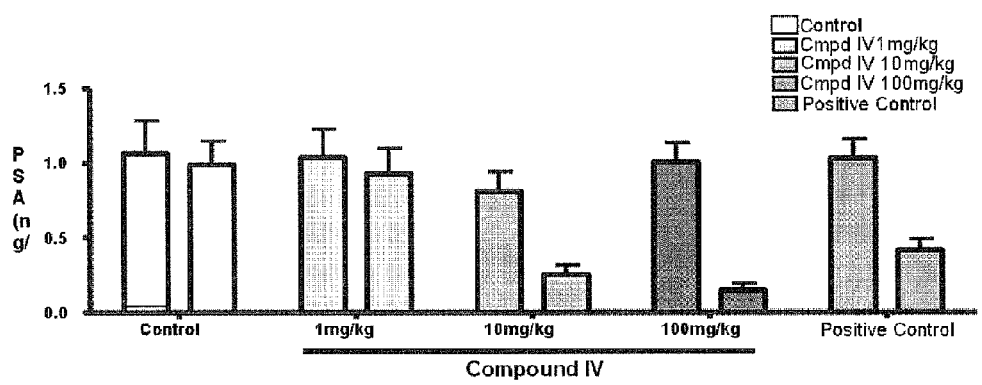
FIG. 16 depicts dose dependent prostate-specific antigen (PSA) levels (ng/mL) in monkeys by administering Compound IV at baseline and at day 28. PSA levels were significantly decreased with Compound IV treatment. (See Example 16.)

Serum PSA levels were also significantly suppressed by Compound IV within four weeks of treatment initiation. PSA reductions of 69% and 87% (in mean) were noted for monkeys receiving Compound IV at 10 mg/kg and 100 mg/kg for 4 weeks, whereas PSA levels were reduced by 60% in the positive control (LHRH agonist) group (FIG. 16 and Tables 13-16).

TABLE 13

Mean serum PSA levels (ng/mL) in intact male monkeys after daily oral administration of Compound IV; @Estimated final concentrations.

| | Vehicle Control | | | Compound IV 1 mg/kg | | | Compound IV 10 mg/kg | | | Compound IV 100 mg/kg | | | Positive control (LHRH agonist) | | |
|---|---|---|---|---|---|---|---|---|---|---|---|---|---|---|---|
| | Mean | SEM | N | Mean | SEM | N | Mean | SEM | N | Mean | SEM | N | Mean | SEM | N |
| Pre-dose | 1.1 | 0.2 | 10 | 1.0 | 0.2 | 6 | 0.8 | 0.1 | 6 | 1.0 | 0.1 | 10 | 1.0 | 0.1 | 7 |
| 4-week | 1.0 | 0.2 | 10 | 0.9 | 0.2 | 6 | 0.3* | 0.1 | 6 | 0.1$^\&$ | 0.1 | 10 | 0.4$^{\#\$}$ | 0.1 | 7 |

PSA assay LLOQ = 0.0575 ng/mL;
@BLQ values are calculated as 0.02875 ng/mL, half of the LLOQ.
*Statistically significant (p < 0.05) Compound IV 10 mg/kg vs. Vehicle Control
$^\&$Statistically significant (p < 0.05) Compound IV 100 mg/kg vs. Vehicle Control
$^\#$Statistically significant (p < 0.05) Positive control (LHRH agonist) vs. Vehicle Control
$^\$$Statistically significant (p < 0.05) Positive control (LHRH agonist) vs. Compound IV 100 mg/kg

TABLE 14

Percentage change (%) of mean PSA levels compared to baseline; @Estimated final concentrations.

| | Control | Compound IV 1 mg/kg | Compound IV 10 mg/kg | Compound IV 100 mg/kg | Positive control (LHRH agonist) |
|---|---|---|---|---|---|
| 4-week | −7.1 | −11 | −69 | −87 | −60 |

PSA assay LLOQ = 0.0575 ng/mL;
@BLQ values are calculated as 0.02875 ng/mL, half of the LLOQ.

TABLE 15

Mean serum PSA levels (ng/mL) in intact male monkeys after daily oral administration Compound IV; $^\lambda$Quantifiable concentrations only.

| | Vehicle Control | | | Compound IV 1 mg/kg | | | Compound IV 10 mg/kg | | | Compound IV 100 mg/kg | | | Positive control (LHRH agonist) | | |
|---|---|---|---|---|---|---|---|---|---|---|---|---|---|---|---|
| | Mean | SEM | N | Mean | SEM | N | Mean | SEM | N | Mean | SEM | N | Mean | SEM | N |
| Pre-dose | 1.2 | 0.2 | 9 | 1.0 | 0.2 | 6 | 0.8 | 0.1 | 6 | 1.0 | 0.1 | 10 | 1.0 | 0.1 | 7 |
| 4-week | 1.1 | 0.1 | 9 | 0.9 | 0.2 | 6 | 0.3 | 0.1 | 5 | 0.3 | 0.1 | 4 | 0.4 | 0.1 | 7 |

PSA assay LLOQ = 0.0575 ng/mL;
$^\lambda$BLQ values are excluded in this table.

TABLE 16

Percentage change (%) of mean PSA levels compared to baseline; ^Quantifiable concentrations only.

| | Control | Compound IV 1 mg/kg | Compound IV 10 mg/kg | Compound IV 100 mg/kg | Positive Control |
|---|---|---|---|---|---|
| 4-week | −7.1 | −11 | −64 | −72 | −60 |

PSA assay LLOQ = 0.0575 ng/mL;
^BLQ values are excluded in this table.

Figure 17:
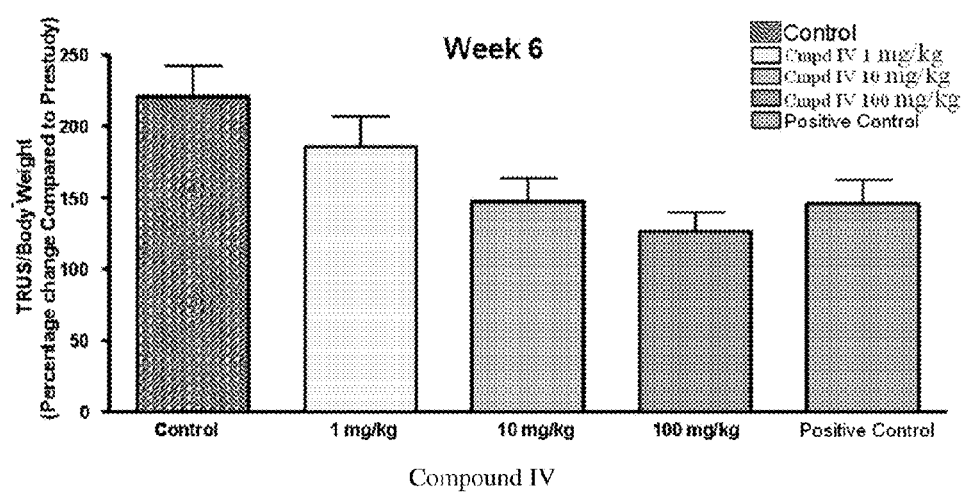
FIG. 17 depicts dose dependent prostate volume using Transrectal ultrasound (TRUS) in monkeys compared to positive control (LHRH agonist), by administering Compound IV at week 6. (See Example 16.)

Prostate volumes were measured by TRUS periodically throughout the study. Results obtained after six weeks of treatment demonstrate a potent effect of Compound IV and positive control (LHRH agonist) on monkey prostate. Compound IV significantly suppressed prostate volumes by 25% and 45% at the 10 mg/kg and 100 mg/kg dose levels, respectively, whereas prostate volumes were reduced by 28% in the positive control (LHRH agonist) group (FIG. 17 and Tables 17 and 18).

TABLE 17

Mean prostate volumes (ratio) in male monkeys after daily oral administration Compound IV.

| | Vehicle Control | | | Compound IV 1 mg/kg | | | Compound IV 10 mg/kg | | | Compound IV 100 mg/kg | | | Positive control (LHRH agonist) | | |
|---|---|---|---|---|---|---|---|---|---|---|---|---|---|---|---|
| | Mean | SEM | N | Mean | SEM | N | Mean | SEM | N | Mean | SEM | N | Mean | SEM | N |
| 6-week | 438 | 78 | 10 | 468 | 78 | 6 | 327 | 33 | 6 | 242 | 28 | 10 | 315 | 47 | 7 |

TABLE 18

Percentage change (%) of mean prostate volumes compared to baseline.

| | Control | Compound IV 1 mg/kg | Compound IV 10 mg/kg | Compound IV 100 mg/kg | Positive Control |
|---|---|---|---|---|---|
| 6-week | 0 | 6.8 | −25 | −45 | −28 |

Figure 18:
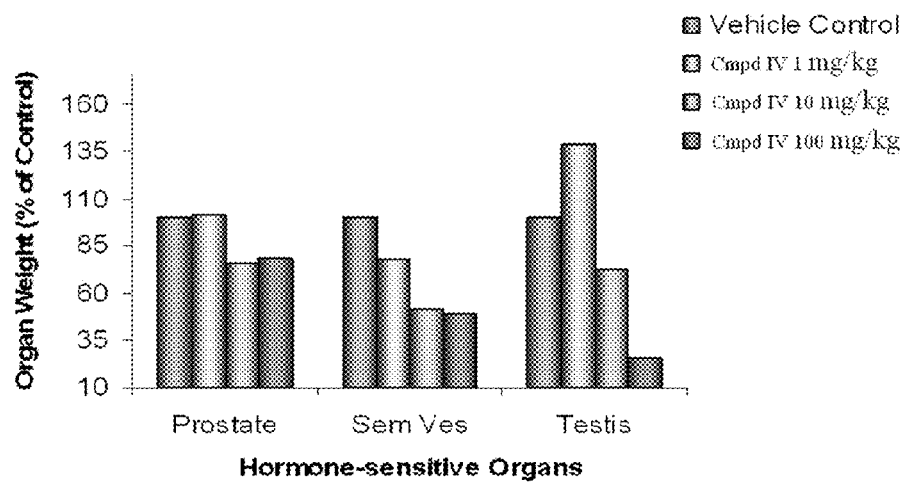
FIG. 18 depicts dose dependent organ weights (prostate, seminal vesicle and testis) as percent of control of monkeys at day 90, by administering Compound IV (FIG. 18A).*Prostate weights at 13-week necropsy in monkeys after daily oral administration of Compound IV (FIG. 18B). (See Example 16.)

The Compound IV -related reductions in prostate volume were confirmed by the evaluation of prostate weight at necropsy. After thirteen weeks of treatment, Compound IV significantly reduced mean prostate weights by 24% and 21% in animals receiving 10 and 100 mg/kg/day, respectively (FIG. 18B and Tables 19 and 20).

TABLE 19

Mean prostate weights (grams) at necropsy in monkeys with daily oral administration Compound IV.

| | Vehicle Control | | | Compound IV 1 mg/kg | | | Compound IV 10 mg/kg | | | Compound IV 100 mg/kg | | |
|---|---|---|---|---|---|---|---|---|---|---|---|---|
| | Mean | SEM | N | Mean | SEM | N | Mean | SEM | N | Mean | SEM | N |
| 13-week | 1.8 | 0.2 | 3 | 1.8 | 0.4 | 3 | 1.3 | 0.1 | 3 | 1.4 | 0.1 | 3 |

TABLE 20

Percentage change (%) of mean prostate weights compared to baseline.

|  | Control | Compound IV 1 mg/kg | Compound IV 10 mg/kg | Compound IV 100 mg/kg |
|---|---|---|---|---|
| 13-week | 0 | 1.7 | −24 | −21 |

No apparent effects on platelet aggregation, prothrombin time (PT) or activated partial thromboplastin time (APTT) were observed.

Example 17

Compound IV Studies on Humans

Figure 19:
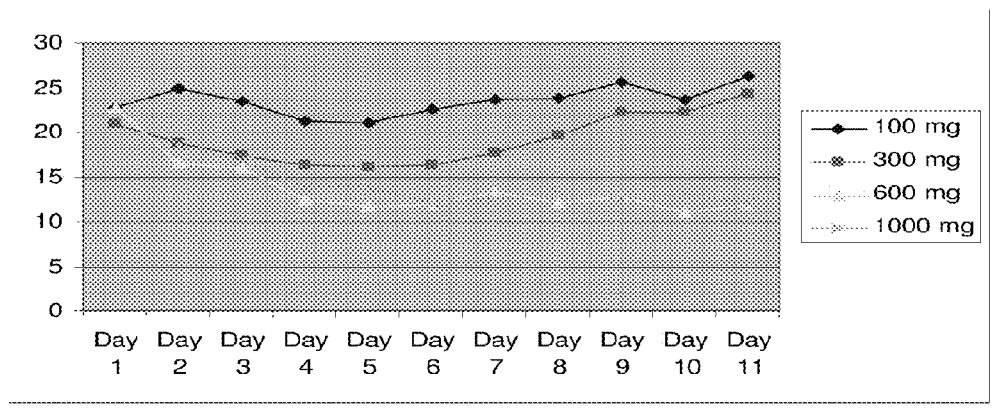
FIG. 19 depicts dose dependent mean total testosterone levels (nmol/L) in humans for a period between 1-11 days by administering compound IV (100 mg, 300 mg, 600 mg and 1000 mg). (See Example 17.)

A study was conducted to determine the effect of Compound IV on human males. 12 subjects per cohort were examined in dosages of 100, 300, 600 and 1000 mg of Compound IV. Table 21 presents mean change of LH, serum PSA, free testosterone and total testosterone levels in men by administering Compound IV at dosages of 100, 300, 600 and 1000 mg. Dose dependent mean total testosterone levels (nmol/L) in humans were measured for a period between days 1-11 (FIG. 19). Total testosterone level decreased by 51.9% and 47.9% at dosages of 600 mg and 1000 mg, respectfully.

Figure 20:
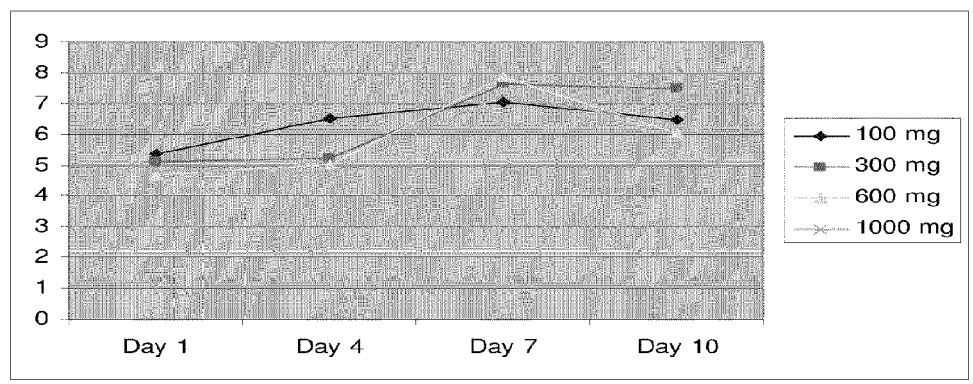
FIG. 20 depicts dose dependent mean LH levels (IU/L) in humans for a period between 1-10 days by administering compound IV (100 mg, 300 mg, 600 mg and 1000 mg. (See Example 17.)

Dose dependent mean LH levels (IU/L) in humans were measured for a period between days 1-10 (FIG. 20). The LH levels increased by 20.7%, 46.9%, 27.6% and 29.2% at dosages of 100 mg, 300 mg, 600 mg and 1000 mg, respectfully.

Figure 21:
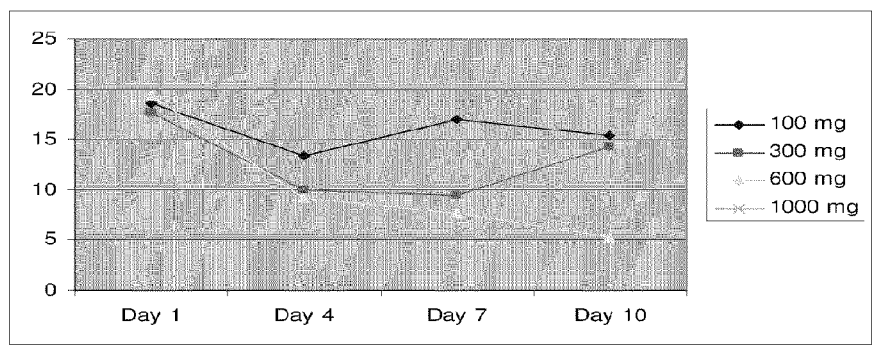
FIG. 21 depicts dose dependent mean free testosterone levels (pg/mL) in humans for a period between 1-10 days by administering compound IV (100 mg, 300 mg, 600 mg and 1000 mg. (See Example 17.)

Dose dependent mean free testosterone levels (pg/mL) in humans were measured for a period between days 1-10 (FIG. 21). The free testosterone levels decreased by 17.0%, 18.5%, 72.7% and 53.2% at dosages of 100 mg, 300 mg, 600 mg and 1000 mg, respectfully.

Figure 22:
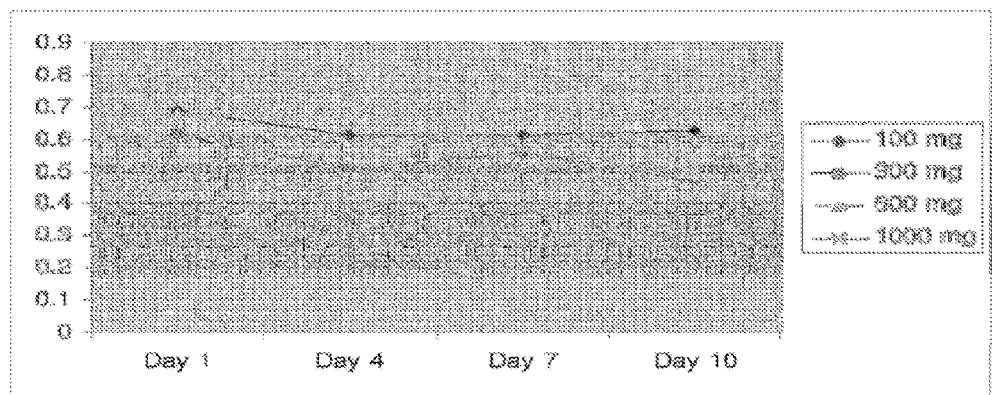
FIG. 22 depicts dose dependent mean PSA levels (μg/L) in humans for a period between 1-10 days by administering compound IV (100 mg, 300 mg, 600 mg and 1000 mg). (See Example 17.)

Dose dependent mean PSA levels (μg/L) in humans were measured for a period between days 1-10 (FIG. 22). The PSA levels decreased by 9.2%, 24.4%, 27.5% and 29.9% at dosages of 100 mg, 300 mg, 600 mg and 1000 mg, respectfully. No changes noted for 10 and 30 mg doses.

TABLE 21

Mean change from baseline.

|  | 100 mg | 300 mg | 600 mg | 1000 mg |
|---|---|---|---|---|
| Serum PSA | −9.2% | −24.4% | −27.5% | −29.9% |
| LH | 20.7% | 46.9% | 27.6% | 29.2% |
| Free Testosterone | −17.0% | −18.5% | −72.7% | −53.2% |
| Total Testosterone | 3.9% | 7.3% | −51.9% | −47.9% |

Example 18

Bioavailability of Compound IV

Compound IV was rapidly absorbed following oral dosing to rats, dogs and monkeys. The oral bioavailability of Compound IV in rats ranged from 6% to 25% depending on the formulation in which the dose was administered. Formulations using polyethylene glycol 300 (PEG300) generally produced higher exposures than microemulsions prepared in Tween 80 diluted in deionized water. In dogs, visual inspection of the plasma concentration-time profiles suggested that Compound IV undergoes enterohepatic recirculation as evidenced by a second peak in the terminal phase. Importantly, in dogs the exposure in the male 30 mg/kg PEG300 oral dose group exceeded the exposure necessary to produce the maximal effect on prostate reduction in the rat model of LH suppression. In monkeys, preliminary pharmacokinetic studies suggested that oral bioavailability in this species approximates or exceeds that in dogs, as evidenced by plasma concentrations of Compound IV and suppression of serum testosterone over a seven day period. As a whole, these data suggest that sufficient oral exposure can be achieved in two non-rodent animal species to produce the desired pharmacologic effect (based on AUC data). Further, endocrine data in rats and monkeys suggest that the pharmacologic effects of Compound IV are reversible (i.e., serum concentrations of testosterone return to baseline or normal levels when treatment with Compound IV is stopped).

Example 19

Pharmacokinetics of Compound IV

Preliminary data from in vitro (mouse, rat, dog, monkey and human) and in vivo (rat) metabolism studies suggest that conjugation of Compound IV, its hydroxylated metabolite(s) and its N-dealkylated metabolite contribute to the overall disposition of Compound IV in animals and humans. The results of the interspecies comparison, although only qualitative, show that the overall metabolite profiles of the nonclinical species adequately reflect the profile generated in human liver microsomes. Based on these results, the rat and dog are appropriate rodent and nonrodent species, respectively, for pharmacology and toxicology evaluations. In vitro studies show Compound IV does not induce relevant CYP450 isoforms (CYP1A2, CYP2B6, or CYP3A4) and does not inhibit CYP1A2, CYP2C19, CYP2D6, or CYP3A4/5 at concentrations <30 μM. CYP2C9 is inhibited by Compound IV but only at high concentrations ($K_i$=8 μM), and potential pharmacokinetic drug-drug interactions are considered remote.

Example 20

Biological Activity of Compound IV

Compound IV exerts little or no in vitro inhibitory effects ($IC_{50} \geq 300$ μM) on the hERG channel. The compound dose-dependently decreased APD50 and APD90 at concentrations of 10 and 100 μM in isolated canine Purkinje fibers in vitro. However, Compound IV did not affect hemodynamic or cardiac function (blood pressure, heart rate, electrocardiogram morphology or QT intervals) in telemetered dogs at any dose (up to 300 mg/kg). No neuropharmacological or pulmonary effects were observed. No significant effects were noted on renal function with a single oral dose of up to 30 mg/kg Compound IV. Only increased urine volume output and urinary excretion of potassium and chloride were observed at the highest dose tested (100 mg/kg). Oral administration of Compound IV at doses of 30 to 300 mg/kg in rats produced a significant increase in peristalsis, and oral administration of Compound IV at 30 mg/kg in rats produced a significant increase in gastrointestinal motility and gastric acidity (likely not due to effects on smooth muscle).

Compound IV was not mutagenic and did not induce structural or numeric chromosomal aberrations at concentrations up to 200 μM in human peripheral blood lymphocytes in vitro. Compound IV was well-tolerated by rats and dogs after single and repeated oral administration (up to 28 days). There were no pathologic changes observed in the kidney, liver, heart and other non-target-related organs. There were no serious physical signs, body weight effects, clinical pathology changes, ophthalmologic, electrocardiographic, or histopathologic changes associated with oral administration of Compound IV to male or female dogs for up to 28 days.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating androgen deprivation therapy (ADT) induced hot flashes in a subject comprising administering a therapeutically effective amount of a compound of formula I, or its optical isomer or pharmaceutical acceptable salt, or any combination thereof:

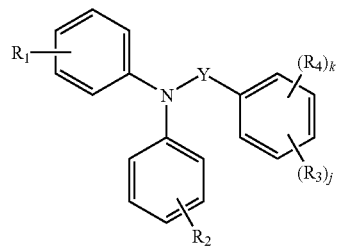

wherein

Y is C(O) or CH$_2$;

R$_1$, R$_2$ are independently hydrogen, halogen, hydroxyl, alkoxy, cyano, nitro, CF$_3$, N(R)$_2$, sulfonamide, SO$_2$R, alkyl, haloalkyl, aryl, O-Alk-NR$_5$R$_6$ or O-Alk-heterocycle in which the heterocycle is a 3-7 membered substituted or unsubstituted heterocyclic ring, optionally aromatic;

R$_3$, R$_4$ are independently hydrogen, halogen, hydroxyalkyl, hydroxyl, alkoxy, cyano, nitro, CF$_3$, NHCOR, N(R)$_2$, sulfonamide, SO$_2$R, alkyl, haloalkyl, aryl or protected hydroxyl;

R is alkyl, hydrogen, haloalkyl, dihaloalkyl, trihaloalkyl, CH$_2$F, CHF$_2$, CF$_3$, CF$_2$CF$_3$, aryl, phenyl, halogen, alkenyl, CN, NO$_2$, or OH;

R$_5$ and R$_6$ are independently hydrogen, phenyl, an alkyl group of 1 to 6 carbon atoms, a 3 to 7 membered cycloalkyl, a 3 to 7 membered heterocycle, a 5 to 7 membered aryl; or R$_5$ and R$_6$ form a 3 to 7 membered ring with the nitrogen atom;

j and k are independently 1-4;

Alk is linear alkyl of 1-7 carbons, branched alkyl of 1-7 carbons, or cyclic alkyl of 3-8 carbons.

2. The method of claim 1, wherein said compound of formula I is selected from:

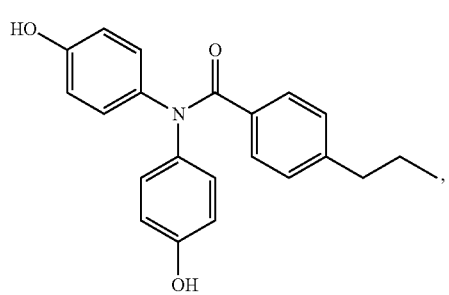

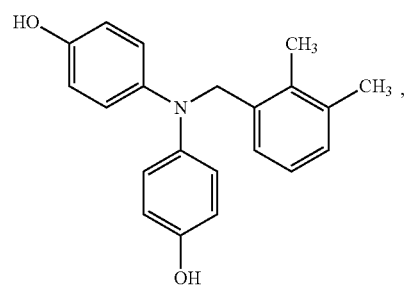

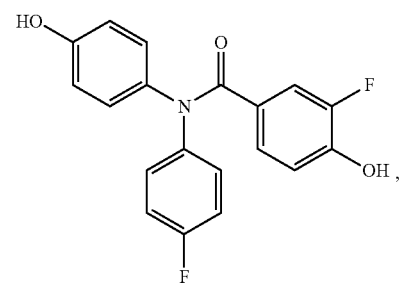

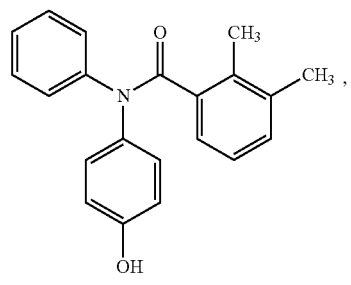

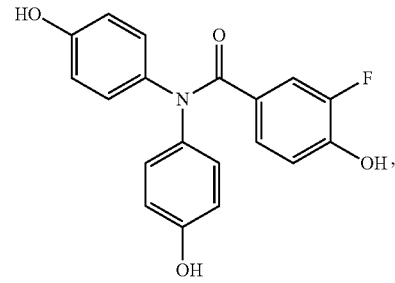

6. The method of claim 5, wherein said prostate cancer is advanced prostate cancer.

7. A method of reducing the incidence of, suppressing, or inhibiting androgen deprivation therapy (ADT) induced hot flashes in a subject comprising administering a therapeutically effective amount of a compound of formula I, or its optical isomer or pharmaceutical acceptable salt, or any combination thereof:

(I)

wherein

Y is C(O) or $CH_2$;

$R_1$, $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic;

$R_3$, $R_4$ are independently hydrogen, halogen, hydroxyalkyl, hydroxyl, alkoxy, cyano, nitro, $CF_3$, NHCOR, $N(R)_2$, sulfonamide, $SO_2R$, alkyl, haloalkyl, aryl or protected hydroxyl;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_5$ and $R_6$ are independently hydrogen, phenyl, an alkyl group of 1 to 6 carbon atoms, a 3 to 7 membered cycloalkyl, a 3 to 7 membered heterocycle, a 5 to 7 membered aryl; or $R_5$ and $R_6$ form a 3 to 7 membered ring with the nitrogen atom;

j and k are independently 1-4;

Alk is linear alkyl of 1-7 carbons, branched alkyl of 1-7 carbons, or cyclic alkyl of 3-8 carbons.

8. The method of claim 7, wherein said compound of formula I is selected from:

3. The method of claims 1, wherein said subject is human.
4. The method of claim 3, wherein said human subject is male.
5. The method of claims 1, wherein said subject has prostate cancer.

III.
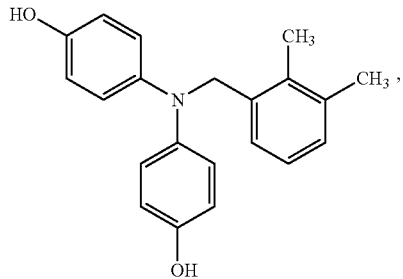

IV.
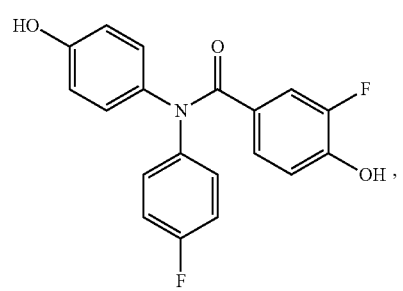

V.
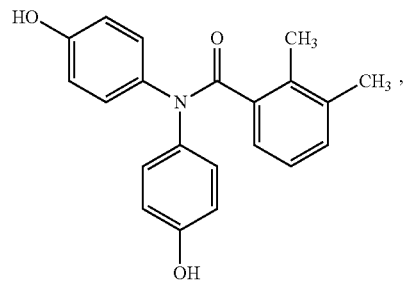

VII.
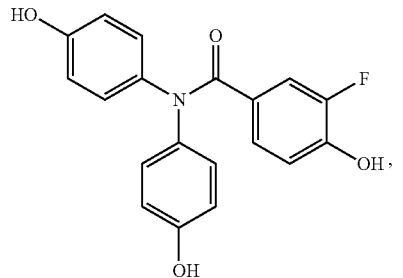

VIII.
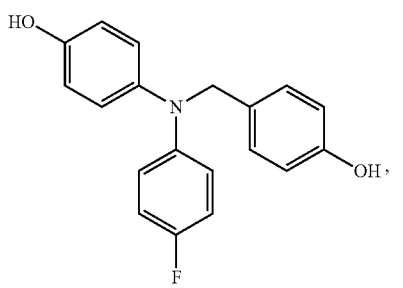

IX.
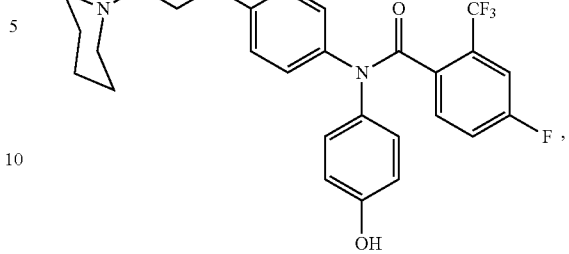

X.
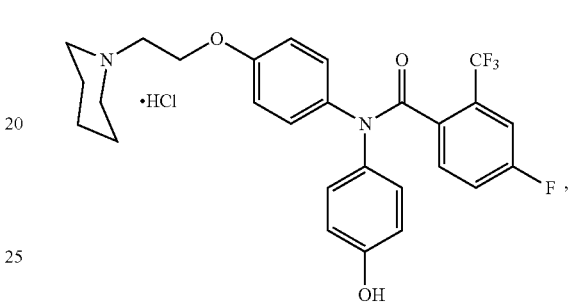

XI.
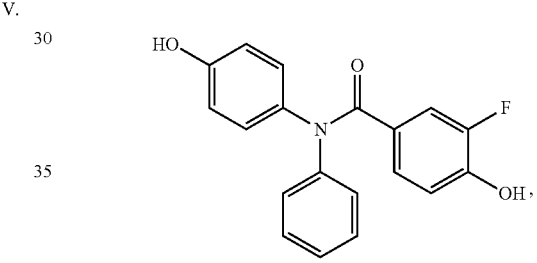

XII.
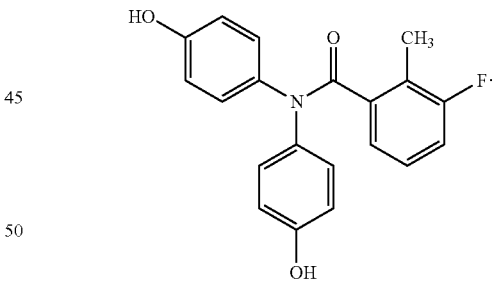

9. The method of claims 7, wherein said subject is human.

10. The method of claim 9, wherein said human subject is male.

11. The method of claims 7, wherein said subject has prostate cancer.

12. The method of claim 11, wherein said prostate cancer is advanced prostate cancer.

13. A method of treating androgen deprivation therapy (ADT) induced severe hot flashes in a subject comprising administering a therapeutically effective amount of a compound of formula I, or its optical isomer or pharmaceutical acceptable salt, or any combination thereof:

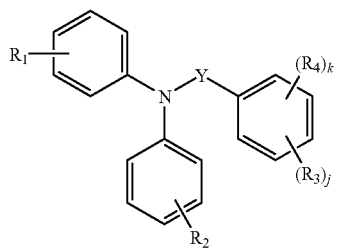

(I)

wherein

Y is C(O) or CH$_2$;

R$_1$, R$_2$ are independently hydrogen, halogen, hydroxyl, alkoxy, cyano, nitro, CF$_3$, N(R)$_2$, sulfonamide, SO$_2$R, alkyl, haloalkyl, aryl, O-Alk-NR$_5$R$_6$ or O-Alk-heterocycle in which the heterocycle is a 3-7 membered substituted or unsubstituted heterocyclic ring, optionally aromatic;

R$_3$, R$_4$ are independently hydrogen, halogen, hydroxyalkyl, hydroxyl, alkoxy, cyano, nitro, CF$_3$, NHCOR, N(R)$_2$, sulfonamide, SO$_2$R, alkyl, haloalkyl, aryl or protected hydroxyl;

R is alkyl, hydrogen, haloalkyl, dihaloalkyl, trihaloalkyl, CH$_2$F, CHF$_2$, CF$_3$, CF$_2$CF$_3$, aryl, phenyl, halogen, alkenyl, CN, NO$_2$, or OH;

R$_5$ and R$_6$ are independently hydrogen, phenyl, an alkyl group of 1 to 6 carbon atoms, a 3 to 7 membered cycloalkyl, a 3 to 7 membered heterocycle, a 5 to 7 membered aryl; or R$_5$ and R$_6$ form a 3 to 7 membered ring with the nitrogen atom;

j and k are independently 1-4;

Alk is linear alkyl of 1-7 carbons, branched alkyl of 1-7 carbons, or cyclic alkyl of 3-8 carbons.

14. The method of claim 13, wherein said compound of formula I is selected from:

II.

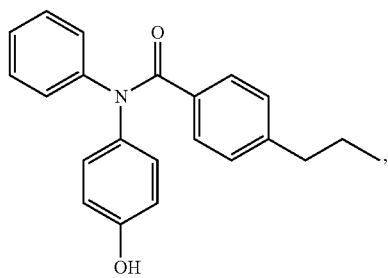

III.

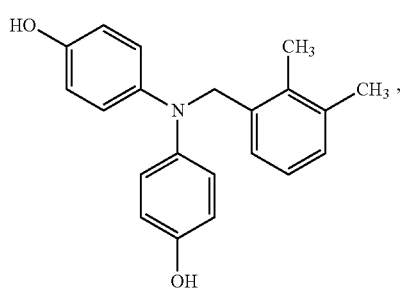

IV.

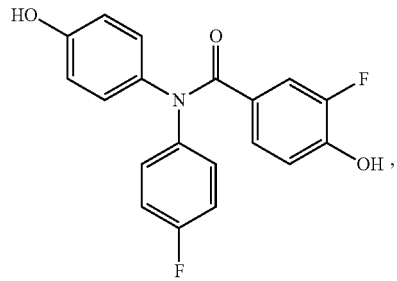

V.

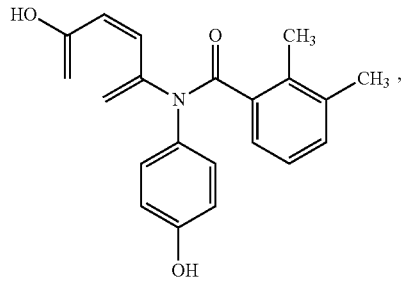

VII.

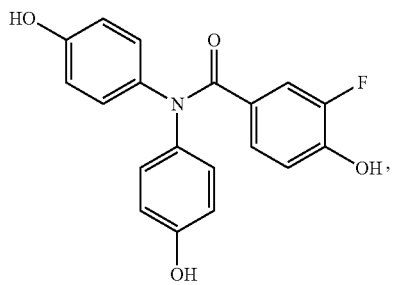

VIII.

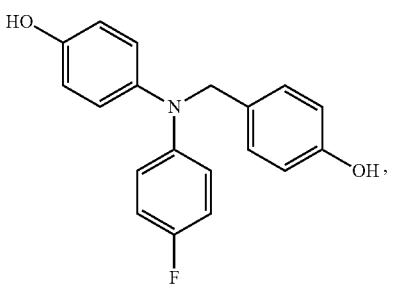

IX.

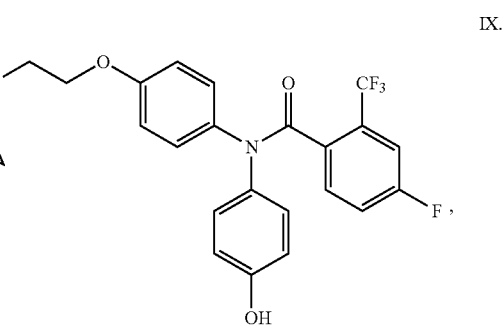

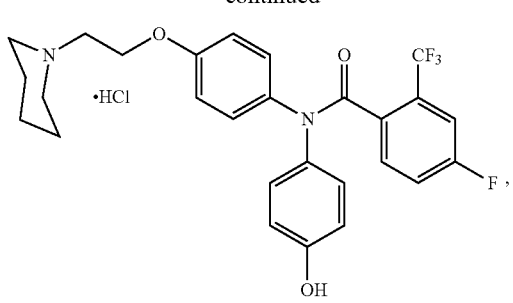
X.

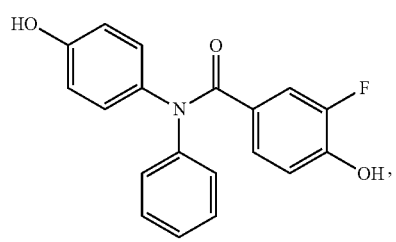
XI.

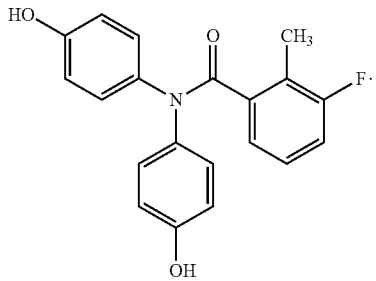
XII.

15. The method of claims 13, wherein said subject is human.

16. The method of claim 15, wherein said human subject is male.

17. The method of claims 13, wherein said subject has prostate cancer.

18. The method of claim 17, wherein said prostate cancer is advanced prostate cancer.

19. A method of reducing the incidence of, suppressing, or inhibiting androgen deprivation therapy (ADT) induced severe hot flashes in a subject comprising administering a therapeutically effective amount of a compound of formula I, or its optical isomer or pharmaceutical acceptable salt, or any combination thereof:

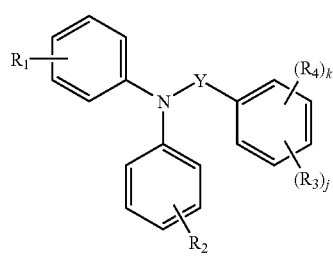
(I)

wherein
Y is C(O) or CH$_2$;
R$_1$, R$_2$ are independently hydrogen, halogen, hydroxyl, alkoxy, cyano, nitro, CF$_3$, N(R)$_2$, sulfonamide, SO$_2$R, alkyl, haloalkyl, aryl, O-Alk-NR$_5$R$_6$ or O-Alk-hetero-cycle in which the heterocycle is a 3-7 membered substituted or unsubstituted heterocyclic ring, optionally aromatic;

R$_3$, R$_4$ are independently hydrogen, halogen, hydroxyalkyl, hydroxyl, alkoxy, cyano, nitro, CF$_3$, NHCOR, N(R)$_2$, sulfonamide, SO$_2$R, alkyl, haloalkyl, aryl or protected hydroxyl;

R is alkyl, hydrogen, haloalkyl, dihaloalkyl, trihaloalkyl, CH$_2$F, CHF$_2$, CF$_3$, CF$_2$CF$_3$, aryl, phenyl, halogen, alkenyl, CN, NO$_2$, or OH;

R$_5$ and R$_6$ are independently hydrogen, phenyl, an alkyl group of 1 to 6 carbon atoms, a 3 to 7 membered cycloalkyl, a 3 to 7 membered heterocycle, a 5 to 7 membered aryl; or R$_5$ and R$_6$ form a 3 to 7 membered ring with the nitrogen atom;

j and k are independently 1-4;

Alk is linear alkyl of 1-7 carbons, branched alkyl of 1-7 carbons, or cyclic alkyl of 3-8 carbons.

20. The method of claim 19, wherein said compound of formula I is selected from:

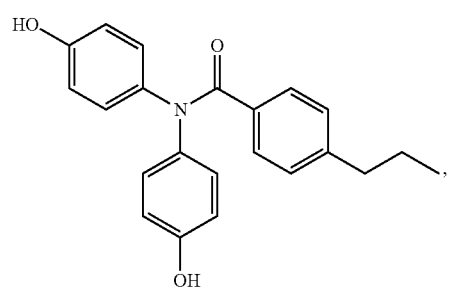
II.

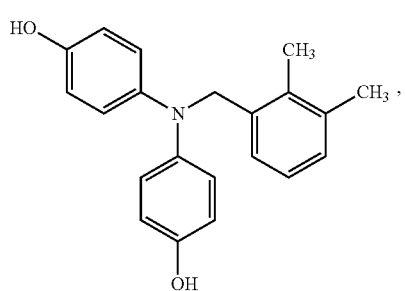
III.

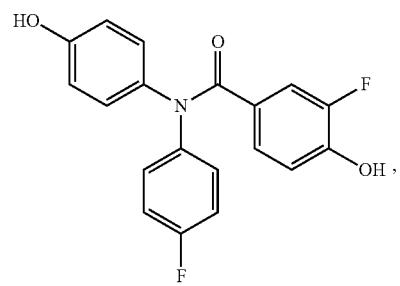
IV.

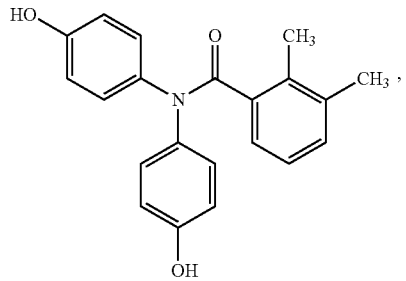
V.
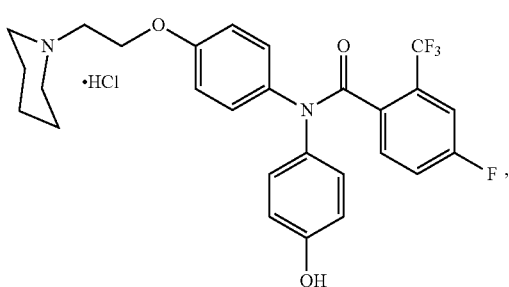
X.
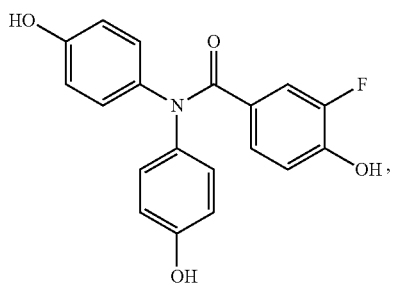
VII.
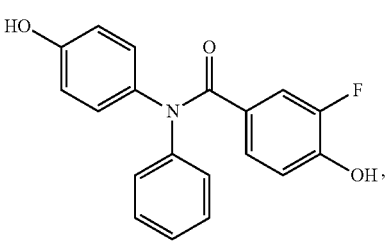
XI.
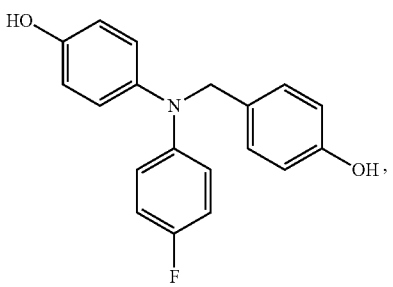
VIII.
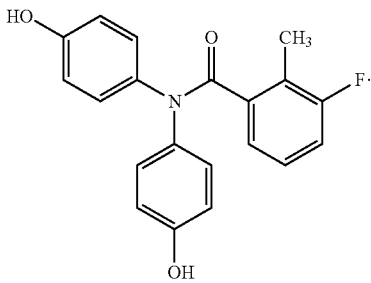
XII.
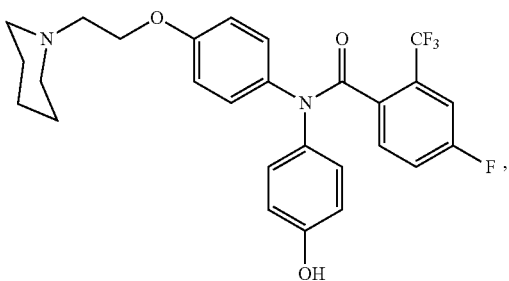
IX.
21. The method of claims 19, wherein said subject is human.
22. The method of claim 21, wherein said human subject is male.
23. The method of claims 19, wherein said subject has prostate cancer.
24. The method of claim 23, wherein said prostate cancer is advanced prostate cancer.
* * * * *